(12) United States Patent
Berme et al.

(10) Patent No.: US 10,117,602 B1
(45) Date of Patent: Nov. 6, 2018

(54) BALANCE AND/OR GAIT PERTURBATION SYSTEM AND A METHOD FOR TESTING AND/OR TRAINING A SUBJECT USING THE SAME

(71) Applicant: Bertec Corporation, Columbus, OH (US)

(72) Inventors: Necip Berme, Worthington, OH (US); Jaswandi Tushar Pitale, Hilliard, OH (US); Scott Zerkle Barnes, Thornville, OH (US); Qian Wang, Plain City, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 15/706,689

(22) Filed: Sep. 16, 2017

Related U.S. Application Data

(63) Continuation-in-part of application No. 15/488,472, filed on Apr. 15, 2017, now Pat. No. 9,763,604, (Continued)

(51) Int. Cl.
*A61B 5/11* (2006.01)
*A63B 69/00* (2006.01)
(Continued)

(52) U.S. Cl.
CPC .......... *A61B 5/112* (2013.01); *A63B 22/0242* (2013.01); *A63B 22/0292* (2015.10);
(Continued)

(58) Field of Classification Search
CPC ... A61B 5/112; A63B 69/0053; A63B 26/003; A63B 24/0087; A63B 22/0292;
(Continued)

(56) References Cited

U.S. PATENT DOCUMENTS 6,038,488 A    3/2000 Barnes et al.
6,113,237 A    9/2000 Ober et al.
(Continued)

OTHER PUBLICATIONS

First office action on the merits (Non-Final Rejection) in U.S. Appl. No. 15/095,040, dated Jul. 18, 2016.
(Continued)

*Primary Examiner* — Sundhara Ganesan
(74) *Attorney, Agent, or Firm* — The Law Office of Patrick F. O'Reilly III, LLC

(57) ABSTRACT

A balance and/or gait perturbation system is disclosed herein. The balance and/or gait perturbation system includes a balance and/or gait perturbation device, at least one visual display device having an output screen, and one or more data processing devices. The one or more data processing devices are operatively coupled to the balance and/or gait perturbation device and the at least one visual display device, the one or more data processing devices are configured to generate a stochastic signal for controlling a display parameter of one or more scenes on the output screen of the at least one visual display device, and the one or more data processing devices are further configured to display the one or more scenes on the output screen of the at least one visual display device using the stochastic signal such that the one or more scenes perturb a balance and/or gait of the person.

19 Claims, 29 Drawing Sheets

Related U.S. Application Data which is a continuation-in-part of application No. 15/095,040, filed on Apr. 9, 2016, now Pat. No. 9,622,686.

(51) Int. Cl.
  *A63B 26/00* (2006.01)
  *A63B 24/00* (2006.01)
  *A63B 22/02* (2006.01)
  *A63B 71/06* (2006.01)

(52) U.S. Cl.
  CPC ........ *A63B 24/0087* (2013.01); *A63B 26/003* (2013.01); *A63B 69/0053* (2013.01); *A63B 2024/0093* (2013.01); *A63B 2071/0658* (2013.01); *A63B 2220/10* (2013.01); *A63B 2220/30* (2013.01); *A63B 2220/40* (2013.01); *A63B 2220/51* (2013.01); *A63B 2220/833* (2013.01); *A63B 2220/836* (2013.01)

(58) Field of Classification Search
  CPC ........ A63B 22/0242; A63B 2024/0093; A63B 2220/833; A63B 2220/51; A63B 2220/40; A63B 2220/30; A63B 2220/10; A63B 2220/836; A63B 2071/0658
  See application file for complete search history.

(56) References Cited

U.S. PATENT DOCUMENTS

| | | | |
|---|---|---|---|
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,622,747 B2 | 1/2014 | Chu et al. | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 2003/0110148 A1 | 6/2003 | Ulyanov et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2011/0312473 A1 | 12/2011 | Chu et al. | |
| 2012/0021873 A1* | 1/2012 | Brunner | A63B 22/0235 482/9 |
| 2012/0266648 A1 | 10/2012 | Berme et al. | |
| 2012/0271565 A1 | 10/2012 | Berme et al. | |
| 2013/0132031 A1 | 5/2013 | Gilg et al. | |
| 2015/0096387 A1 | 4/2015 | Berme et al. | |
| 2016/0245711 A1 | 8/2016 | Berme et al. | |
| 2016/0334288 A1 | 11/2016 | Berme et al. | |

OTHER PUBLICATIONS

Notice of Allowance in U.S. Appl. No. 15/095,040, dated Dec. 12, 2016.

Notice of Allowance in U.S. Appl. No. 15/488,472, dated May 18, 2017.

* cited by examiner

BALANCE AND/OR GAIT PERTURBATION SYSTEM AND A METHOD FOR TESTING AND/OR TRAINING A SUBJECT USING THE SAME

CROSS-REFERENCE TO RELATED APPLICATIONS

This is a continuation-in-part of U.S. Nonprovisional patent application Ser. No. 15/488,472, entitled "Gait Perturbation System and a Method For Testing and/or Training a Subject Using the Same", filed on Apr. 15, 2017, which is a continuation-in-part of U.S. Nonprovisional patent application Ser. No. 15/095,040, entitled "Gait Perturbation System and a Method For Testing and/or Training a Subject Using the Same", filed on Apr. 9, 2016, now U.S. Pat. No. 9,622,686, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a balance and/or gait perturbation system. More particularly, the invention relates to a balance and/or gait perturbation system that is capable of perturbing a balance and/or gait of a person.

2. Background and Description of Related Art

In order to study human motion, subjects are often tested in gait labs which are provided with special equipment disposed therein for measuring body movements, body mechanics, and/or the activity of the muscles (e.g., gait labs with force plates, etc.). The gait analysis performed in the gait lab is typically used to assess, plan, and/or treat subjects with medical conditions affecting their ability to walk. Also, the gait analysis is often used in sports biomechanics to improve athletic performance, and to help identify and/or treat injuries that deleteriously affect athletic performance.

However, the artificial nature of a typical environment for testing and/or training the balance and/or gait of a subject (e.g., a typical gait lab or clinician's office) makes it difficult to simulate the real-life conditions that are encountered by the subject. Also, these artificial environments for balance and gait testing and/or training are unable to effectively simulate the uncertain nature of the stimuli encountered by subjects in real-life scenarios. As such, these artificial balance gait testing and/or training environments are limited in their overall ability to effectively test and/or train subjects for the scenarios that are actually experienced by subjects in the their everyday lives.

Therefore, what is needed is a balance and/or gait perturbation system that is capable of simulating real-life conditions by subjecting the person being tested to static and/or dynamic instability. Moreover, a balance and/or gait perturbation system is needed that is capable of generating random stimuli in order to emulate real-life conditions encountered by the person undergoing testing. Furthermore, what is needed is a balance and/or gait perturbation system that is capable of more effectively training a person with a balance and/or gait disorder by delivering random stimuli to the person so that he or she is able to more effectively react to unpredictable disturbances that are encountered in real-life scenarios.

BRIEF SUMMARY OF EMBODIMENTS OF THE INVENTION

Accordingly, the present invention is directed to a balance and/or gait perturbation system and a method for testing and/or training a subject using the same that substantially obviates one or more problems resulting from the limitations and deficiencies of the related art.

In accordance with one or more embodiments of the present invention, there is provided a balance and/or gait perturbation system comprising a balance and/or gait perturbation device, at least one visual display device, and one or more data processing devices. The balance and/or gait perturbation device is configured to receive a person thereon, and the balance and/or gait perturbation device includes a surface for receiving at least one portion of the body of the person; and at least one force transducer, the at least one force transducer configured to sense one or more measured quantities and output one or more measurement signals that are representative of forces and/or moments being applied to the surface of the balance and/or gait perturbation device. The at least one visual display device has an output screen, and the at least one visual display device is configured to display one or more scenes on the output screen so that the scenes are viewable by the person. The one or more data processing devices are operatively coupled to the balance and/or gait perturbation device and the at least one visual display device, the one or more data processing devices are configured to receive the one or more measurement signals that are representative of the forces and/or moments being applied to the surface of the force measurement assembly by the person, and to convert the one or more measurement signals into output forces and/or moments, the one or more data processing devices are further configured to generate a stochastic signal for controlling a display parameter of the one or more scenes on the output screen of the at least one visual display device, and the one or more data processing devices are additionally configured to display the one or more scenes on the output screen of the at least one visual display device using the stochastic signal such that the one or more scenes perturb a balance and/or gait of the person.

In a further embodiment of the present invention, the gait perturbation device comprises a displaceable force measurement assembly, the displaceable force measurement assembly including a displaceable force plate subassembly and one or more actuators coupled to the displaceable force plate subassembly, the one or more actuators configured to adjust a displacement position of the displaceable force plate subassembly; and the one or more data processing devices are further configured to control the displacement position of the displaceable force plate subassembly using the stochastic signal.

In yet a further embodiment, the display parameter of the one or more scenes on the output screen of the at least one visual display device comprises a displacement of the one or more scenes on the output screen of the at least one visual display device; and the one or more data processing devices are further configured to displace the one or more scenes on the output screen of the at least one visual display device in synchrony with the displacement of the displaceable force plate subassembly.

In still a further embodiment, the gait perturbation device comprises a treadmill, the treadmill including one or more treadmill displaceable elements and one or more speed adjustment mechanisms coupled to the one or more treadmill displaceable elements, the one or more speed adjustment mechanisms configured to adjust the speed set point at which the one or more treadmill displaceable elements are displaced; and the one or more data processing devices are further configured to control the speed set point of the one or more treadmill displaceable elements using the stochastic signal.

In yet a further embodiment, the display parameter of the one or more scenes on the output screen of the at least one visual display device comprises a displacement of the one or more scenes on the output screen of the at least one visual display device; and the one or more data processing devices are further configured to displace the one or more scenes on the output screen of the at least one visual display device in synchrony with the displacement of the one or more treadmill displaceable elements.

In still a further embodiment, the display parameter of the one or more scenes on the output screen of the at least one visual display device comprises a displacement of the one or more scenes on the output screen of the at least one visual display device; and the one or more data processing devices are configured to displace the one or more scenes on the output screen of the at least one visual display device using the stochastic signal by rotating and/or translating the one or more scenes on the output screen of the at least one visual display device.

In yet a further embodiment, the display parameter of the one or more scenes on the output screen of the at least one visual display device is selected from the group consisting of a focal distance parameter, a smoothness parameter, a focal size parameter, a blur spread parameter, a velocity scale blur parameter, a minimum velocity blur parameter, a maximum velocity blur parameter, a velocity downsample parameter, a jitter strength parameter, a grain intensity multiplier parameter, a color noise parameter, a low light noise parameter, a high light noise parameter, a mid-grey level parameter, a color weight parameter, a noise softness parameter, a texture offset parameter, a texture tiling parameter, an image rotational displacement, an image rotational velocity, an image translational displacement, and an image translational velocity.

In still a further embodiment, the balance and/or gait perturbation system further comprises at least one input device, the at least one input device configured to enable a user to input a perturbation level corresponding to at least of: (i) an amplitude of the stochastic signal, and (ii) a frequency of the stochastic signal; and the data processing device is configured to generate the stochastic signal based upon at least one of: (i) the amplitude of the stochastic signal, and (ii) the frequency of the stochastic signal.

In yet a further embodiment, the stochastic signal comprises a uniform stochastic signal, the data processing device configured to compute the uniform stochastic signal as a function of a randomly generated uniform signal and the perturbation level input by the user.

In still a further embodiment, the stochastic signal comprises a normal stochastic signal, the data processing device configured to compute the normal stochastic signal as a function of a normalized randomly generated uniform signal and the perturbation level input by the user.

In yet a further embodiment, the balance and/or gait perturbation system further comprises at least one input device, the at least one input device configured to enable a user to manually input at least one of: (i) an amplitude of the stochastic signal, (ii) a frequency of the stochastic signal, and (iii) a signal type of the stochastic signal, the signal type of the stochastic signal being selected from the group consisting of a uniform signal and a random signal.

In accordance with one or more other embodiments of the present invention, there is provided a balance and/or gait perturbation system comprising a balance and/or gait perturbation device, at least one visual display device, and a data processing device. The balance and/or gait perturbation device is configured to receive a person thereon, and the balance and/or gait perturbation device includes one or more displaceable components configured to be displaced to a plurality of different positions, the one or more displaceable components having one or more surfaces for receiving one or more respective limbs of the person; and one or more first actuators coupled to the one or more displaceable components, the one or more first actuators configured to adjust the displacement position of the one or more displaceable components, the one or more first actuators being primary means for displacing the one or more displaceable components. The at least one visual display device has an output screen, and the at least one visual display device is configured to display one or more scenes on the output screen so that the scenes are viewable by the person. The data processing device is operatively coupled to the one or more first actuators and the at least one visual display device, the data processing device is configured to generate a stochastic signal for controlling a display parameter of the one or more scenes on the output screen of the at least one visual display device, and the data processing device is additionally configured to display the one or more scenes on the output screen of the at least one visual display device using the stochastic signal such that the one or more scenes perturb a balance and/or gait of the person.

In a further embodiment of the present invention, the balance and/or gait perturbation device comprises a force measurement assembly, and the one or more displaceable components comprise a displaceable force plate subassembly of the force measurement assembly; and the one or more first actuators are configured to adjust the displacement position of the displaceable force plate subassembly.

In yet a further embodiment, the displaceable force plate subassembly includes at least one force transducer, the at least one force transducer configured to sense one or more measured quantities and output one or more measurement signals that are representative of one or more loads being applied to the one or more surfaces of the displaceable force plate subassembly by the person.

In still a further embodiment, the balance and/or gait perturbation device further comprises a base assembly having a stationary portion and a displaceable portion, the displaceable force plate subassembly forming a part of the displaceable portion of the base assembly.

In yet a further embodiment, the display parameter of the one or more scenes on the output screen of the at least one visual display device comprises a rotational displacement of the one or more scenes on the output screen of the at least one visual display device about an imaginary horizontal rotational axis disposed transversely across a width of the at least one visual display device; and the one or more first actuators are configured to rotate the displaceable force plate subassembly relative to the stationary portion of the base assembly using the stochastic signal such that the rotation of the displaceable force plate subassembly is synchronized with the rotational displacement of the one or more scenes on the output screen of the at least one visual display device.

In still a further embodiment, the display parameter of the one or more scenes on the output screen of the at least one visual display device comprises a translational displacement of the one or more scenes on the output screen of the at least one visual display device towards the person on the force plate subassembly and away from the person on the force plate subassembly; and the balance and/or gait perturbation device further comprises one or more second actuators coupled to the displaceable force plate subassembly, the one or more second actuators configured to translate the displaceable force plate subassembly relative to the stationary portion of the base assembly using the stochastic signal such that the translation of the displaceable force plate subassembly is synchronized with the translational displacement of the one or more scenes on the output screen of the at least one visual display device.

In accordance with yet one or more other embodiments of the present invention, there is provided a method for testing and/or training a person using a balance and/or gait perturbation system. The method comprising the steps of: (i) providing a balance and/or gait perturbation device configured to receive a person thereon, the balance and/or gait perturbation device including a surface for receiving at least one portion of the body of the person; and at least one force transducer, the at least one force transducer configured to sense one or more measured quantities and output one or more measurement signals that are representative of forces and/or moments being applied to the surface of the balance and/or gait perturbation device; (ii) providing at least one visual display device having an output screen, the at least one visual display device configured to display one or more scenes on the output screen so that the scenes are viewable by the person; (iii) providing one or more data processing devices operatively coupled to the balance and/or gait perturbation device and the at least one visual display device, the one or more data processing devices configured to receive the one or more measurement signals that are representative of the forces and/or moments being applied to the surface of the force measurement assembly by the person, and to convert the one or more measurement signals into output forces and/or moments, the one or more data processing devices further configured to generate a stochastic signal for controlling a display parameter of the one or more scenes on the output screen of the at least one visual display device, and the one or more data processing devices additionally configured to display the one or more scenes on the output screen of the at least one visual display device using the stochastic signal such that the one or more scenes perturb a balance and/or gait of the person; (iv) positioning the person on the surface of the balance and/or gait perturbation device; (v) sensing, by utilizing the at least one force transducer, one or more measured quantities that are representative of forces and/or moments being applied to the surface of the balance and/or gait perturbation device by the person and outputting one or more measurement signals representative thereof; (vi) converting, by using the one or more data processing devices, the one or more measurement signals that are representative of the forces and/or moments being applied to the surface of the force measurement assembly by the person into output forces and/or moments; (vii) generating, by using the one or more data processing devices, a stochastic signal for controlling a display parameter of the one or more scenes on the output screen of the at least one visual display device, and (viii) displaying, by using the one or more data processing devices, the one or more scenes on the output screen of the at least one visual display device using the stochastic signal such that the one or more scenes perturb a balance and/or gait of the person.

In a further embodiment of the present invention, the method further comprises the steps of: (ix) providing at least one input device operatively coupled to the data processing device, the at least one input device configured to enable a user to input a perturbation level corresponding to at least of: (a) an amplitude of the stochastic signal, and (b) a frequency of the stochastic signal; and (x) generating, by using the data processing device, the stochastic signal based upon at least one of: (a) the amplitude of the stochastic signal, and (b) the frequency of the stochastic signal.

In yet a further embodiment, the stochastic signal comprises one of: (i) a uniform stochastic signal and (ii) a normal stochastic signal.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
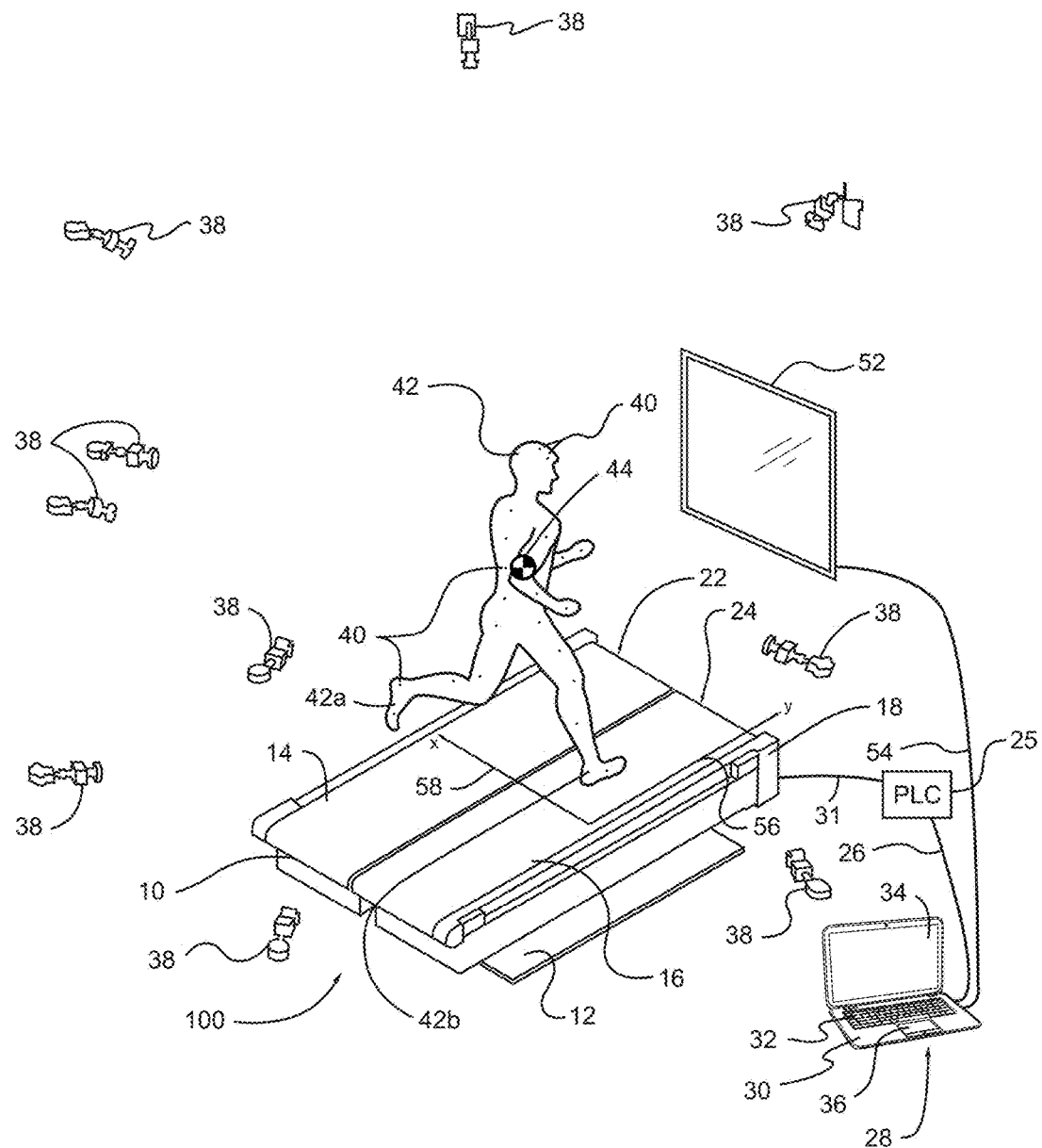
FIG. 1 is a perspective view of a gait perturbation system with a gait perturbation device in the form of an instrumented treadmill, according to a first embodiment of the invention.

An illustrative embodiment of a gait perturbation system is seen generally at 100 in FIG. 1. In the first illustrative embodiment of FIG. 1, the gait perturbation system 100 generally comprises a gait perturbation device 10 in the form of an instrumented treadmill that is operatively coupled to a data acquisition/data processing device 28 (i.e., a data acquisition and processing device or computing device that is capable of collecting, storing, and processing data), which in turn, is operatively coupled to a subject visual display device 52 for displaying images or scenes to the subject 42 disposed on the treadmill 10. The instrumented treadmill 10 is configured to receive a subject 42 thereon. As best illustrated in FIG. 1, the instrumented treadmill 10 is attached to the top of a base plate 12, which in turn, may be secured to a support surface (e.g., a building floor). The instrumented treadmill 10 has a plurality of top surfaces (i.e., left and right rotating belts 14, 16) that are each configured to receive a portion of a body of a subject 42 (e.g., the left belt 14 of the instrumented treadmill 10 is configured to receive a left leg of a subject 42, whereas the right belt 16 of the instrumented treadmill 10 is configured to receive a right leg of the subject 42).

In one or more embodiments, a subject walks or runs in an upright position atop the treadmill 10 with the feet 42a, 42b of the subject 42 contacting the respective top surfaces 22, 24 of the treadmill belts 14, 16. The belts 14, 16 of the treadmill 10 are rotated by independent electric actuator assemblies with one or more speed adjustment mechanisms (e.g., actuator control drive 27 in FIG. 6). In the illustrated embodiment, each electric actuator assembly comprises an electric motor operatively coupled to the actuator control drive 27. Under the control of the actuator control drive 27, each electric actuator assembly is capable of rotating its respective treadmill belt 14, 16 at a plurality of different speeds. The actuator control drive 27 (i.e., speed adjustment mechanism) adjusts the speed(s) at which each of the treadmill belts 14, 16 are rotated. The actuator control drive 27 (i.e., speed adjustment mechanism) of the instrumented treadmill 10 is operatively coupled to a programmable logic controller (PLC) 25 (see FIG. 6). The programmable logic controller 25 of the instrumented treadmill 10 is operatively connected to the data acquisition/data processing device 28 by an electrical cable 26, while the programmable logic controller 25 is operatively connected to the control portion 18 of the instrumented treadmill 10 (e.g., containing the actuator control drive 27) via an electrical cable 31 (see FIG. 1). While they are not readily visible in the perspective view of FIG. 1 due to their location, the instrumented treadmill 10 includes a plurality of force transducers (e.g., four (4) pylon-type force transducers 20—see e.g., FIGS. 2-4) disposed below each rotating belt 14, 16 of the treadmill 10 so that the loads being applied to the top surfaces 22, 24 of the belts 14, 16 can be measured. Advantageously, the separated belts 14, 16 of the instrumented treadmill 10 enable the forces and/or moments applied by the left and right legs of the subject 42 to be independently determined. As will be described in more detail hereinafter, the pylon-type force transducers 20 of the instrumented treadmill 10 are also operatively coupled to the treadmill programmable logic controller 25. In turn, the treadmill programmable logic controller 25 is operatively coupled to the data acquisition/ data processing device 28 so that the force and moment output data of the pylon-type force transducers 20 is capable of being analyzed and processed by the data acquisition/data processing device 28.

Figure 2:
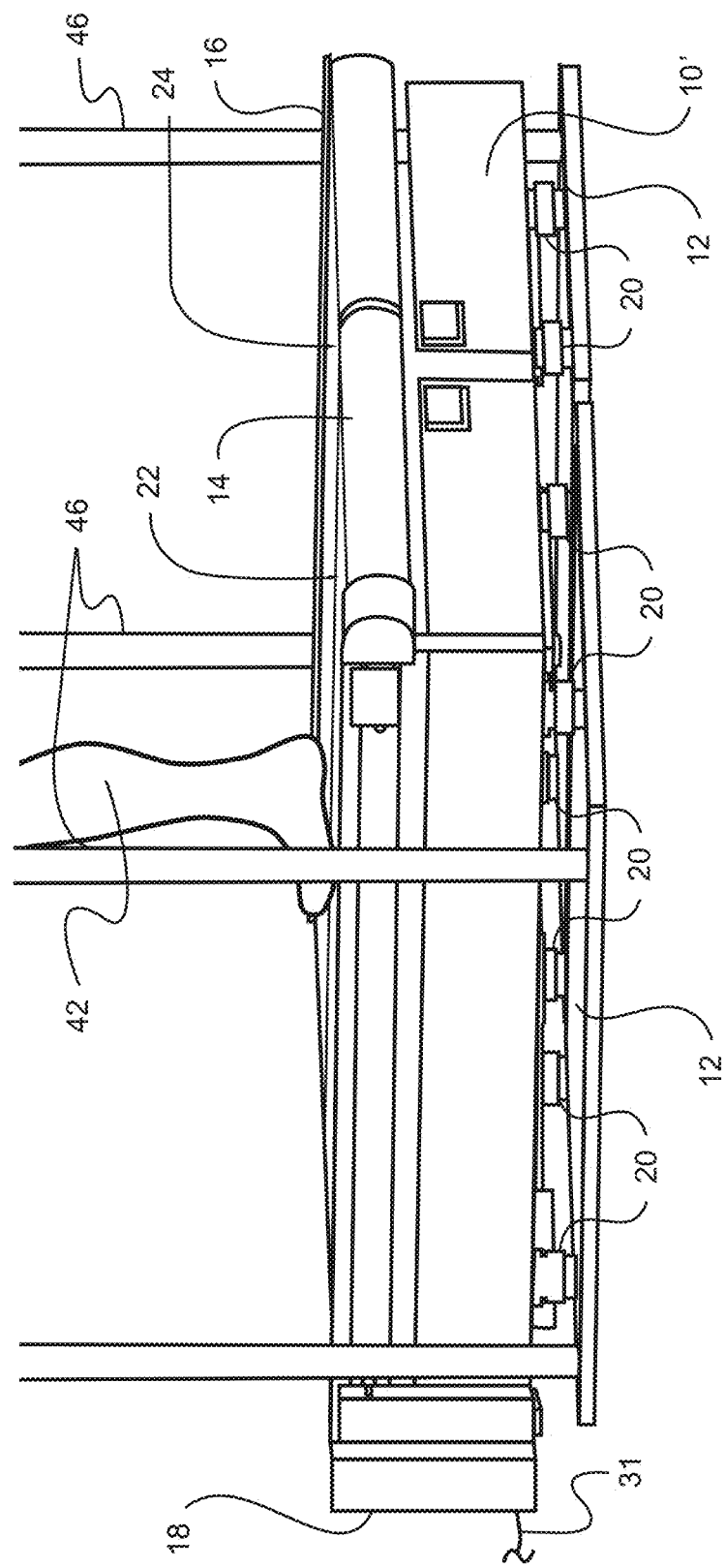
FIG. 2 is an end-side perspective view illustrating the pylon-type force transducers of the instrumented treadmill of FIG. 1, wherein, in this figure, handrails have been added to the instrumented treadmill of FIG. 1.
Figure 3:
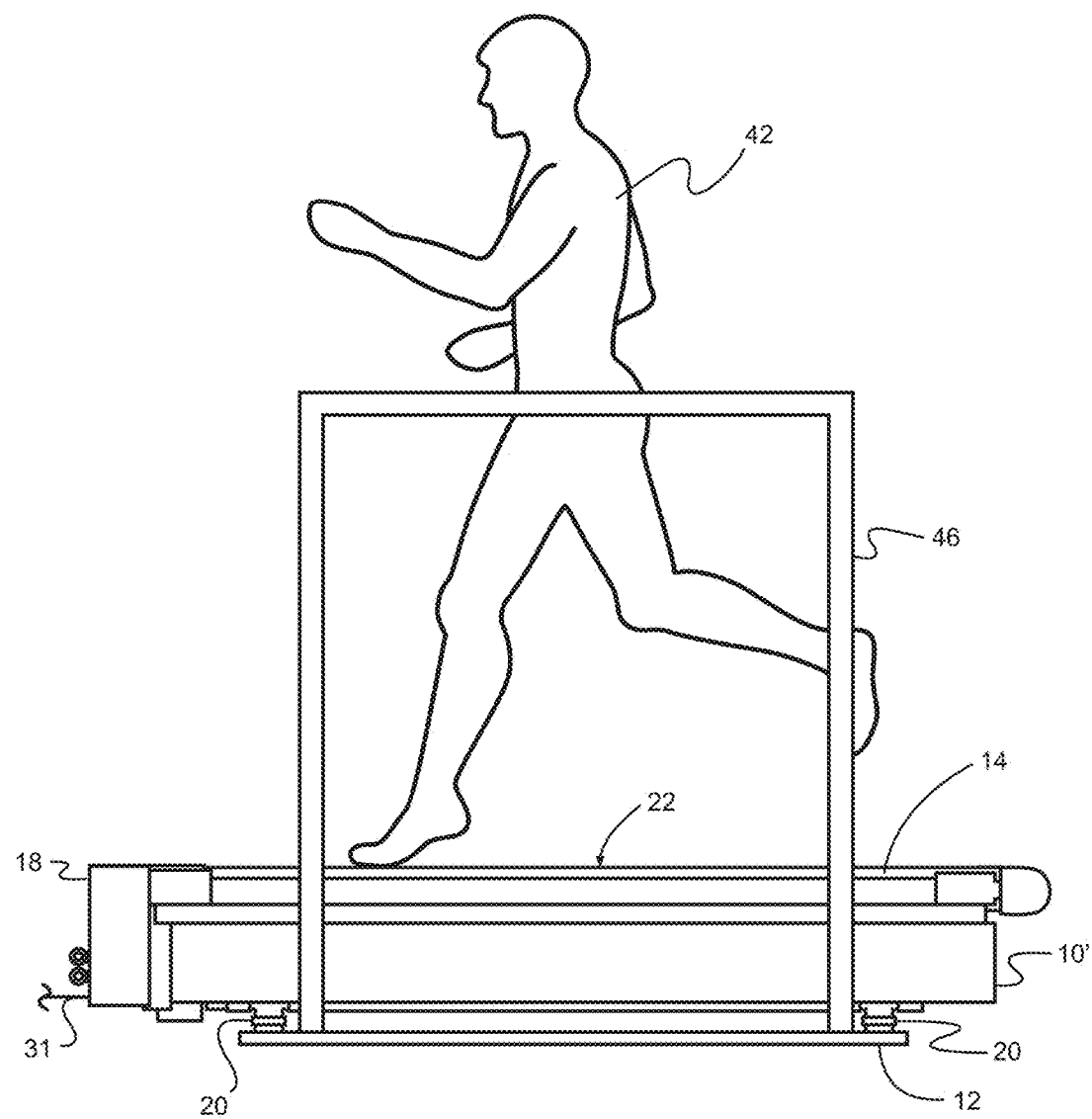
FIG. 3 is a side view illustrating the instrumented treadmill of FIG. 2.
Figure 4:
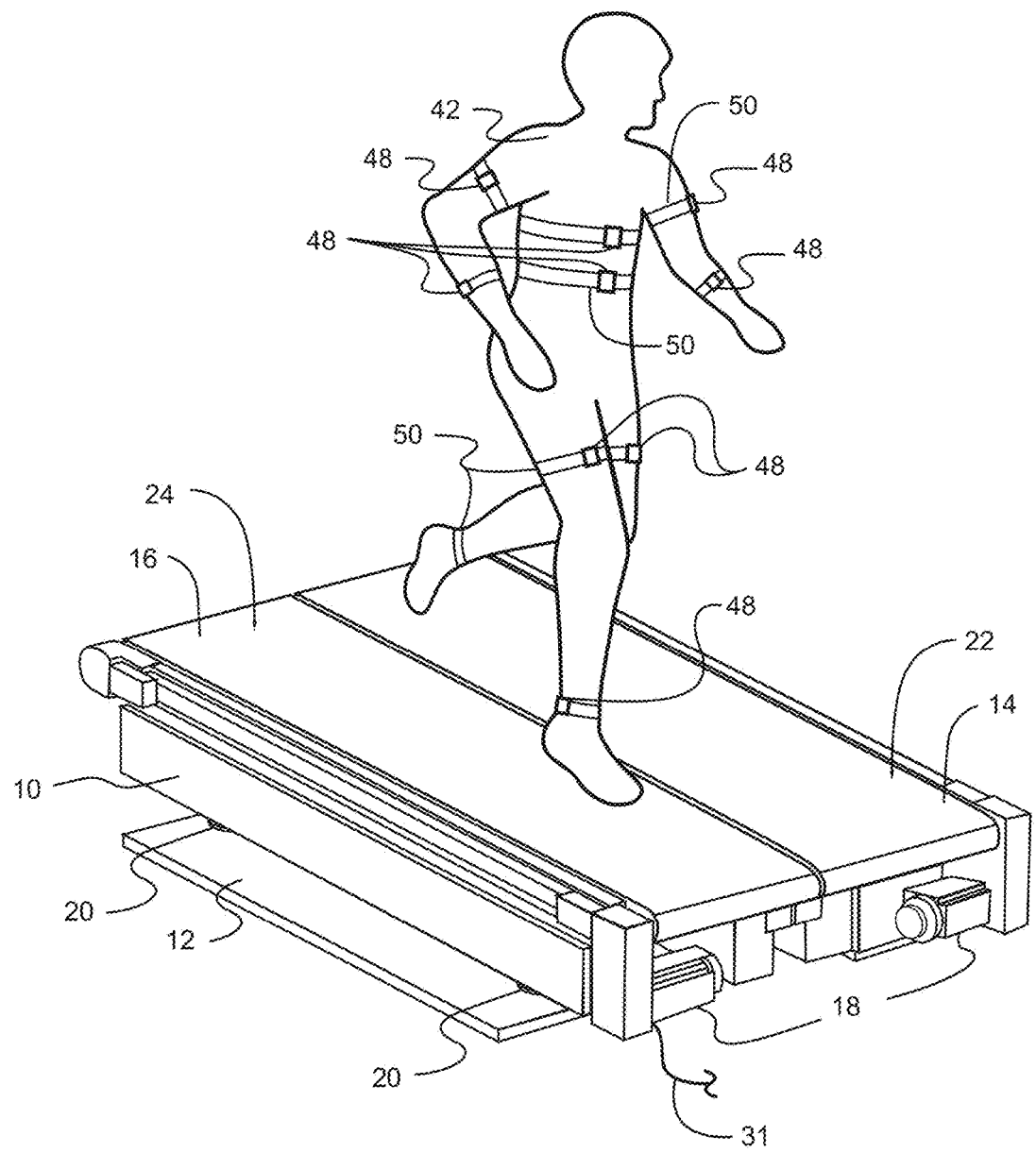
FIG. 4 is another perspective view of a subject disposed on the instrumented treadmill of FIG. 1, wherein the subject is outfitted with a plurality of inertial measurement units (IMUs) thereon.

As mentioned above, each of the treadmill belts 14, 16 is supported atop four (4) pylon-type force transducers 20 (or pylon-type load cells) that are disposed underneath, and near each of the four corners (4) of the left rotating belt 14 of the treadmill 10 and each of the four corners (4) of the right rotating belt 16 (see e.g., FIGS. 2-4). Each of the eight (8) pylon-type force transducers 20 has a plurality of strain gages adhered to the outer periphery of a cylindrically-shaped force transducer sensing element for detecting the mechanical strain of the force transducer sensing element imparted thereon by the force(s) applied to the belt surfaces 22, 24 of the instrumented treadmill 10. In the illustrative embodiment, each of the four (4) sets of pylon-type force transducers 20 are mounted atop the base plate 12.

In an alternative embodiment, rather than using four (4) pylon-type force transducers 20 on each treadmill belt assembly 14, 16, force transducers in the form of transducer beams could be provided under each treadmill belt assembly 14, 16. In this alternative embodiment, the left treadmill belt assembly 14 could comprise two transducer beams that are disposed underneath, and on generally opposite sides of the treadmill belt assembly 14. Similarly, in this embodiment, the right treadmill belt assembly 16 could comprise two transducer beams that are disposed underneath, and on generally opposite sides of the right treadmill belt assembly 16. Similar to the pylon-type force transducers 20, the force transducer beams could have a plurality of strain gages attached to one or more surfaces thereof for sensing the mechanical strain imparted on the beam by the force(s) applied to the surfaces 22, 24 of the instrumented treadmill 10.

Rather, than using four (4) force transducer pylons under each treadmill belt assembly 14, 16, or two spaced-apart force transducer beams under each treadmill belt assembly 14, 16, it is to be understood that the instrumented treadmill 10 can also utilize the force transducer technology described in U.S. Pat. No. 8,544,347, the entire disclosure of which is incorporated herein by reference.

In the illustrated embodiment, the electrical cable 26 mentioned above is used for the transmission of data between the programmable logic controller 25 and the data acquisition/data processing device 28, while the electrical cable 31 is used for the transmission of data between the instrumented treadmill 10 and the programmable logic controller 25. A separate power cable is used to provide power to the instrumented treadmill 10 (e.g., a power cable connected directly to the electrical power system of the building in which the treadmill 10 is disposed). While a hardwired data connection is provided between the programmable logic controller 25 and the data acquisition/data processing device 28 in the illustrative embodiment, it is to be understood that the programmable logic controller 25 can be operatively coupled to the data acquisition/data processing device 28 using other signal transmission means, such as a wireless data transmission system.

Figure 5:
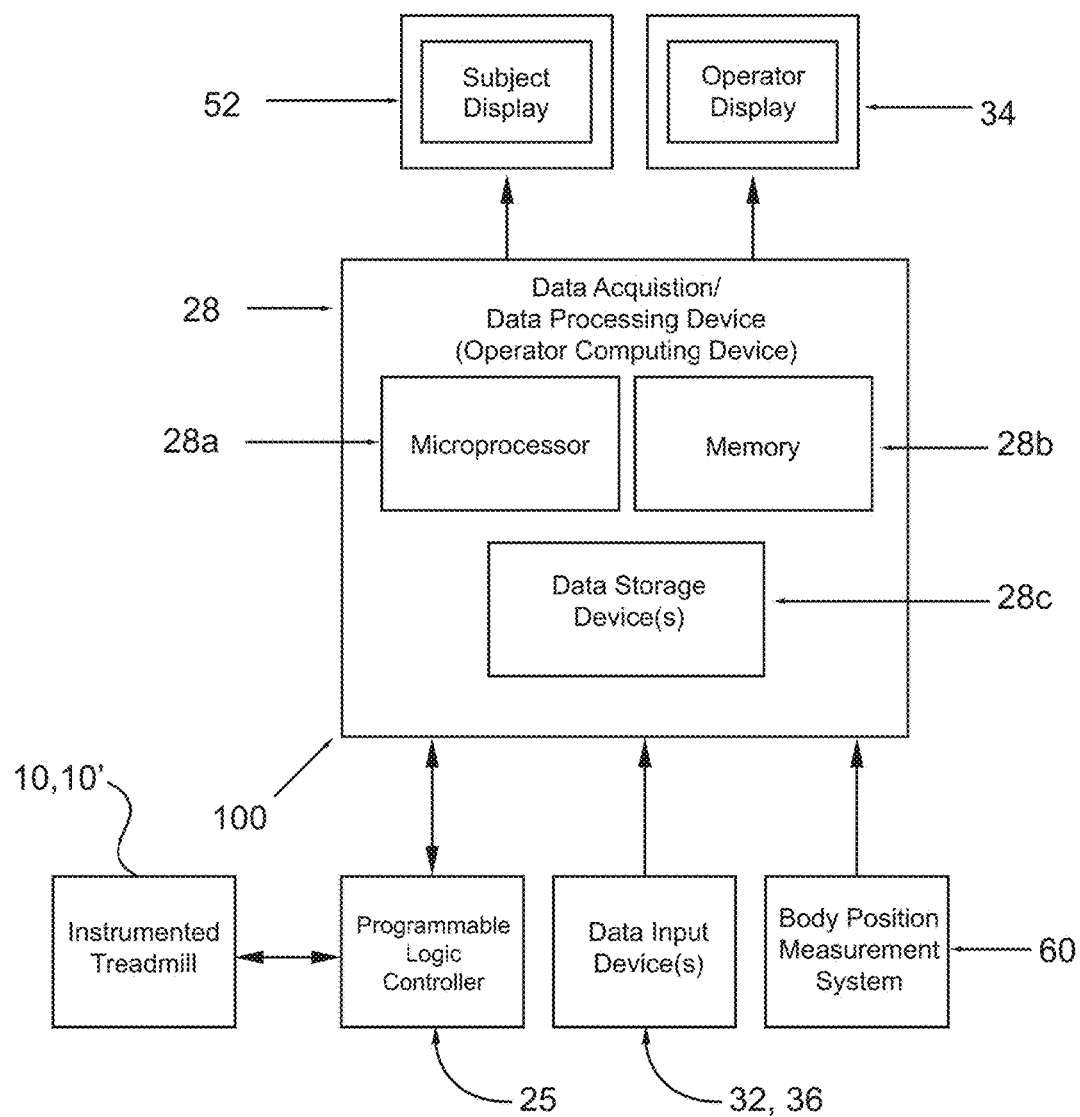
FIG. 5 is a block diagram of constituent components of the gait perturbation system with the instrumented treadmill of FIG. 1, according to an embodiment of the invention.

Now, turning to FIG. 5, it can be seen that the illustrated data acquisition/data processing device 28 (i.e., the operator computing device) of the gait perturbation system 100 includes a microprocessor 28a for processing data, memory 28b (e.g., random access memory or RAM) for storing data during the processing thereof, and data storage device(s) 28c, such as one or more hard drives, compact disk drives, floppy disk drives, flash drives, or any combination thereof. As shown in FIG. 1, the programmable logic controller (PLC) 25 of the instrumented treadmill 10, and the subject visual display device 52 are operatively coupled to the data acquisition/data processing device 28 such that data is capable of being transferred between these devices 25, 28, and 52. In FIG. 1, it can be seen that the programmable logic controller (PLC) 25 of the instrumented treadmill 10 is operatively coupled to the data acquisition/data processing device 28 by the electrical cable 26, while the subject visual display device 52 is operatively coupled to the data acquisition/data processing device 28 by the electrical cable 54. Also, as shown in FIG. 1, the data acquisition/data processing device 28 (e.g., in the form of a laptop digital computer) generally includes a base portion 30 with the microprocessor 28a disposed therein for collecting and processing the data that is received from the instrumented treadmill 10, and a plurality of devices 32-36 operatively coupled to the microprocessor 28a in the base portion 30. Preferably, the devices that are operatively coupled to the microprocessor 28a of the data acquisition/data processing device 28 comprise user input devices 32, 36 in the form of a keyboard 32 and a touchpad 36, as well as a graphical user interface in the form of a laptop LCD screen 34. While a laptop type computing system is depicted in FIG. 1, one of ordinary skill in the art will appreciate that another type of data acquisition/data processing device 28 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse). In addition, rather than providing a data acquisition/data processing device 28, it is to be understood that, in other embodiments, only a data acquisition device could be provided without departing from the spirit and the scope of the claimed invention.

Advantageously, the programmable logic controller 25 (see e.g., FIG. 6, which is a type of data processing device) provides real-time control of the treadmill actuators (i.e., motors) that control the rotation of the left and right treadmill belts 14, 16. The real-time control provided by the programmable logic controller 25 ensures that the software regulating the control of the left and right treadmill belts 14, 16 operates at the design clock rate, thereby providing fail-safe operation for subject safety. As such, user software applications that are being executed on the data acquisition/data processing device 28 do not interfere with the control of the left and right treadmill belts 14, 16. In one embodiment, the programmable logic controller 25 comprises both the treadmill control software and the input/output management software, which controls the functionality of the input/output (I/O) module of the programmable logic controller 25. In one embodiment, the programmable logic controller 25 utilizes EtherCAT protocol for enhanced speed capabilities and real-time control.

In one or more embodiments, the input/output (I/O) module of the programmable logic controller 25 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 25. As another example, a head movement tracking system, which is instrumented with one or more accelerometers, could be operatively connected to the input/output (I/O) module.

Figure 6:
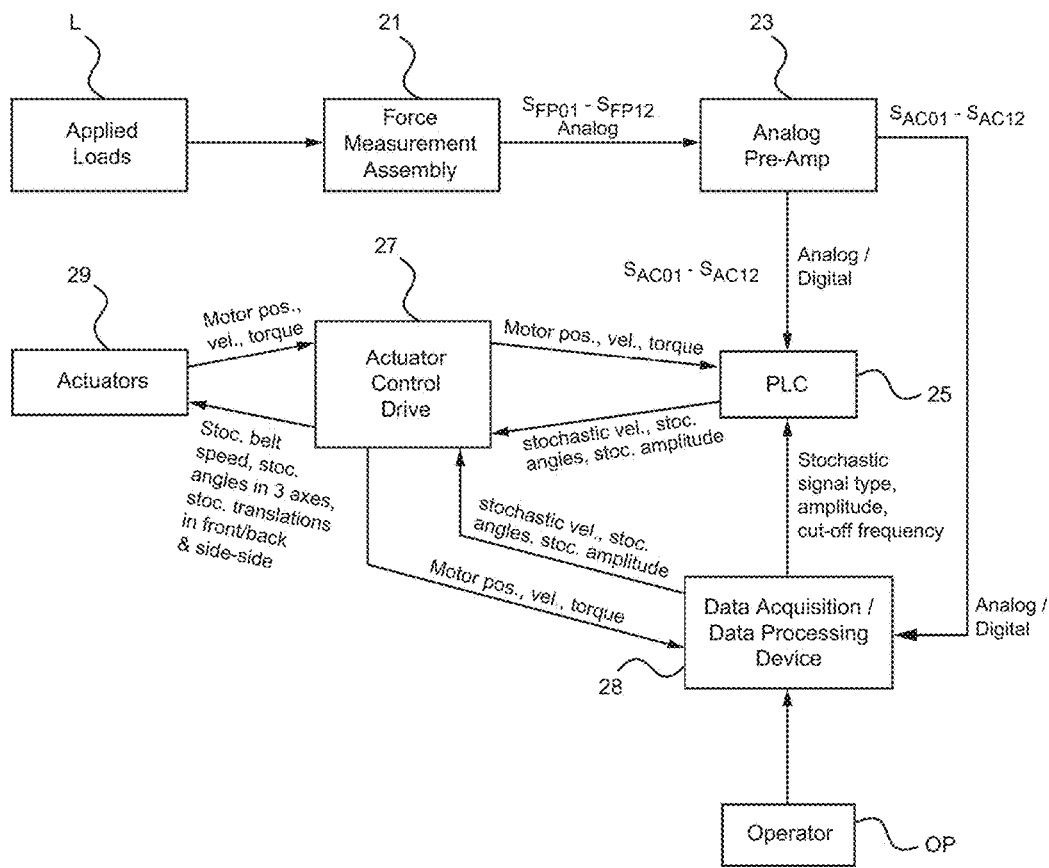
FIG. 6 is a block diagram illustrating the electronic actuator components of the instrumented treadmill of FIG. 1, and the data manipulation operations and motion control operations carried out by the gait perturbation system, according to an embodiment of the invention.

FIG. 6 graphically illustrates the acquisition and processing of the load data and the control of the actuators 29 carried out by the exemplary gait perturbation system 100. Initially, as shown in FIG. 6, a load L is applied to the treadmill force measurement assembly 21 by a subject disposed thereon. In the illustrative embodiment, the force measurement assembly 21 of the gait perturbation system 100 comprises the pylon-type force transducers 20 disposed underneath the treadmill belts 14, 16 described above. The load is transmitted from the treadmill belt assemblies 14, 16 to its respective set of pylon-type force transducers 20 (or force transducer beams). As described above, in the illustrated embodiment, each treadmill belt assembly 14, 16 comprises four (4) pylon-type force transducers 20 disposed thereunder. Preferably, these pylon-type force transducers 20 are disposed near respective corners of each treadmill belt assembly 14, 16. In a preferred embodiment, each of the pylon-type force transducers 20 includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 14, 16. For each plurality of strain gages disposed on the pylon-type force transducers 20, the change in the electrical resistance of the strain gages brings about a consequential change in the output voltage of the Wheatstone bridge (i.e., a quantity representative of the load being applied to the measurement surface). In one embodiment, the four (4) pylon-type force transducers 20 disposed under the treadmill belt assemblies 14, 16 output a total of twelve (12) output voltages (signals) in either analog or digital form. In some embodiments, if the output voltages (signals) are in analog form, the twelve (12) output voltages (signals) from the treadmill belt assemblies 14, 16 are then transmitted to a preamplifier board 23 for preconditioning. The preamplifier board 23 is used to increase the magnitudes of the transducer analog voltages. After which, in one or more embodiments, the analog output signals $S_{ACO1}$-$S_{AC12}$ are transmitted from the analog preamplifier 23 to the treadmill programmable logic controller (PLC) 25. In the treadmill programmable logic controller 25, the analog output signals $S_{ACO1}$-$S_{AC12}$ may be converted into forces, moments, centers of pressure (COP), subject center of gravity (COG), and/or sway angle for the subject. Then, the forces, moments, centers of pressure (COP), subject center of gravity (COG) 44 (see FIG. 1), and/or sway angle for the subject 42 computed by the programmable logic controller 25 are transmitted to the data acquisition/data processing device 28 (operator computing device 28) so that they can be utilized for analyzing the movement of the subject 42 and/or for reports displayed to an operator or clinician. Also, in yet another embodiment, the preamplifier board additionally could be used to convert the analog voltage signals into digital voltage signals (i.e., the preamplifier board could be provided with an analog-to-digital converter). In this embodiment, digital voltage signals would be transmitted to the treadmill programmable logic controller 25 rather than analog voltage signals.

In one or more embodiments, as shown in FIG. 6, when the programmable logic controller 25 receives the voltage signals $S_{AC01}$-$S_{AC12}$, it initially transforms the signals into output forces and/or moments by multiplying the voltage signals $S_{AC01}$-$S_{AC12}$ by a calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 22 of the left treadmill belt assembly 14 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 24 of the right treadmill belt assembly 16 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the programmable logic controller 25, and then transmitted to the data acquisition/data processing device 28.

In one or more alternative embodiments, as also shown in FIG. 6, the voltage signals $S_{AC01}$-$S_{AC12}$ may be transmitted to the data acquisition/data processing device 28, rather than to the programmable logic controller 25. In these one or more alternative embodiments, when the data acquisition/data processing device 28 receives the signals $S_{AC01}$-$S_{AC12}$, it initially transforms the signals $S_{AC01}$-$S_{AC12}$ into output forces and/or moments by multiplying the voltage signals $S_{AC01}$-$S_{AC12}$ by the calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 22 of the left treadmill belt assembly 14 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 24 of the right treadmill belt assembly 16 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the data acquisition/data processing device 28.

Also, in one or more embodiments, as shown in the perspective view of FIG. 1, the overall center of pressure ($x_P$, $y_P$) may also be determined for the subject 42 in accordance with the overall x-coordinate axis 58 and overall y-coordinate axis 56 disposed on the surface of the instrumented treadmill 10.

In the illustrated embodiment, the programmable logic controller 25 converts the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the programmable logic controller 25 also computes a sway angle for the subject using a corrected center of gravity (COG') value, wherein the center of gravity (COG) value is corrected to accommodate for the offset position of the subject relative to the origin of the coordinate axes (56, 58) of the treadmill force measurement assembly 21. For example, the programmable logic controller 25 computes the sway angle for the subject in the following manner:

$$\theta = \sin^{-1}\left(\frac{COG'}{0.55h}\right) - 2.3° \quad (1)$$

where:
θ: sway angle of the subject;
COG': corrected center of gravity of the subject; and
h: height of the center of gravity of the subject.

Now, referring again to the block diagram of FIG. 6, the manner in which the perturbations of the instrumented treadmill 10 are controlled will be explained. Initially, an operator OP inputs one or more motion commands (e.g., start/stop of treadmill belts 14, 16) and/or stochastic signal parameters (e.g., stochastic signal type, amplitude, and cut-off frequency) at the operator computing device 28 (data acquisition/data processing device 28) by utilizing one of the user input devices 32, 36. Once, the one or more motion commands and/or stochastic signal parameters are received at the operator computing device 28, the one or more motion commands and/or stochastic signal parameters are transmitted to the programmable logic controller 25. Then, after further processing by the programmable logic controller 25, the motion command signals (e.g., the one or more base velocity and stochastic signals including the stochastic velocity, stochastic angles, and stochastic amplitude) are transmitted to the actuator control drive 27. Alternatively, when the data acquisition/data processing device 28 generates the stochastic signal rather than the programmable logic controller 25, the motion command signals (e.g., the one or more base velocity and stochastic signals including the stochastic velocity, stochastic angles, and stochastic amplitude) are transmitted from the data acquisition/data processing device 28 directly to the actuator control drive 27, rather than to the programmable logic controller 25. Finally, the actuator control drive 27 transmits the direct-current (DC) motion command signals to the actuators 29 so that the treadmill belts 14, 16, and the subject 42 disposed thereon, can be displaced in the desired manner. The actuator control drive 27 controls the position, velocity, and torque of each actuator motor. Also, as shown in FIG. 6, the motion command signals sent from the actuator control drive 27 to the treadmill actuators 29 may include any one or all of the following: (i) the stochastic belt speed(s), (ii) stochastic angles in three (3) axes, and (iii) stochastic translations in front-to-back and side-to-side directions. In the illustrative embodiment, each of the treadmill belts 14, 16 may be provided with a dedicated rotational actuator 29 for the controlling the belt speeds thereof. In addition, the instrumented treadmill 10 may be provided with three (3) or more actuators 29 for rotating the instrumented treadmill 10 about the x, y, and z-coordinate axes, one or more translational actuators 29 for displacing the instrumented treadmill 10 in a front-to-back direction, and one or more translational actuators 29 for displacing the instrumented treadmill 10 in a side-to-side direction (i.e., secondary means for displacing the one or more displaceable components of the gait perturbation device in a side-to-side direction different from the primary front-to-back direction of the displacement of the belts 14, 16). Referring again to FIG. 6, in the alternative embodiment, it can be seen that the stochastic velocity, stochastic angles, and the stochastic amplitude may be transmitted directly from the operator computing device 28 to the actuator control drive 27 for controlling the actuators 29. The actuators 29 for rotating the instrumented treadmill 10 about the x, y, and z-coordinate axes, and for translating the treadmill 10, may be incorporated in a motion base disposed underneath the instrumented treadmill 10, such as that illustrated and described in commonly owned U.S. Pat. No. 9,081,436, the entire disclosure of which is incorporated herein by reference.

In order to accurately control the motion of the instrumented treadmill 10, a closed-loop feedback control routine may be utilized by the gait perturbation system 100. As shown in FIG. 6, the actuator control drive 27 receives the position, velocity, and torque of each actuator motor from the encoders provided as part of each actuator assembly 29. Then, from the actuator control drive 27, the position, velocity, and torque of each actuator motor is transmitted to the programmable logic controller 25, wherein the feedback control of the actuator assemblies 29 is carried out. In addition, the position, velocity, and torque of each actuator motor may also be transmitted from the actuator control drive 27 to the operator computing device 28 so that it is capable of being used to characterize the movement of the subject 42 on the instrumented treadmill 10 (e.g., the motor positional data and/or torque can be used to compute the sway of the subject).

In one or more embodiments, an emergency stop switch may be operatively coupled to the programmable logic controller 25 in order to quasi-instantaneously stop the rotation of the treadmill belts 14, 16 and/or the displacement of the instrumented treadmill 10 by the actuators 29. As such, the emergency stop switch is a safety mechanism that protects a subject disposed on the instrumented treadmill 10 from potential injury. In an exemplary embodiment, the emergency stop switch may be in the form of a red pushbutton that can be easily pressed by a user of the gait perturbation system 100 in order to stop the rotation of the treadmill belts 14, 16.

Turning to FIGS. 2 and 3, it can be seen that the instrumented treadmill 10' is similar in all respects to the instrumented treadmill 10 of FIGS. 1 and 4, except that the instrumented treadmill 10' in FIGS. 2 and 3 further includes handrails 46 attached to the base plate 12. While the subject 42 is walking or running on the instrumented treadmill 10', the handrails 46 can be grasped by the subject 42 in the event that the subject 42 loses his or her balance on the treadmill. Also, the subject 42 may grasp the handrails 46 when he or she first begins walking or running on the treadmill 10'. In addition, subjects who have balance and mobility problems may use the handrails 46 to stabilize themselves while walking or running on the treadmill 10'.

In one or more further embodiments, the gait perturbation system 100 that includes the instrumented treadmill 10 and the data acquisition/data processing device 28 further includes a body position measurement system 60 (refer to diagrammatic representation of the system in FIG. 5). The body position measurement system 60 is configured to detect the position of an upper body portion of the subject and output one or more position data signals that are representative of the position of the upper body portion of the subject. In one or more embodiments, the upper body portion of the subject is disposed above the feet of the subject. In particular, with reference to FIG. 1, the body position measurement system 60 may comprise a motion capture system having a plurality of cameras 38. In another embodiment, as shown in FIG. 4, the body position measurement system 60 may comprises a plurality of inertial measurement units (IMUs) 48 configured to be coupled to the upper body portion of the subject (e.g., as described below with regard to FIG. 4). It is to be understood that the system 100 may comprise any number or all of these body position measurement systems 38, 48 depending on the type(s) of measurements that need to be performed by the system 100.

As shown in the illustrative embodiment of FIG. 1, when the body position measurement system 60 of the gait perturbation system 100 is in the form of a motion capture system, a plurality of cameras 38 are disposed around the instrumented treadmill 10 so that the cameras 38 at least partially surround the subject 42 disposed on the treadmill 10. In the illustrative embodiment, the cameras 38 are used to track positions of a plurality of markers 40 disposed on the subject 42 as the subject moves his or her torso and limbs in 3-dimensional space. The markers on the subject 42 are used to record the position of the torso and limbs of the subject 42 in 3-dimensional space. While ten (10) cameras 38 are depicted in FIG. 1, one of ordinary skill in the art will appreciate that more or less cameras can be utilized, provided that the motion of the subject 42 is capable of being captured from substantially all angles. In the illustrative embodiment of the invention, the subject 42 has a plurality of single markers 40 applied to anatomical landmarks (e.g., the iliac spines of the pelvis, the malleoli of the ankle, and the condyles of the knee), and/or clusters of markers applied to the middle of body segments. As the subject 42 executes particular movements on the instrumented treadmill 10, the data acquisition/data processing device 28 is specially programmed to calculate the trajectory of each marker 40 in three (3) dimensions. Then, once the positional data is obtained using the motion capture system of FIG. 1, inverse kinematics may be employed in order to further determine the joint angles of the subject 42. That is, the motion capture system of FIG. 1 generates motion capture data that is representative of the captured motion of the body portions of the subject, and the data acquisition/data processing device 28 is specially programmed to determine the position of the body of the subject (i.e., limbs, torso, head, etc.) and the joint angles of the subject from the motion capture data generated by the motion capture system.

While the motion capture system of FIG. 1 described above employs a plurality of markers 40, it is to be understood that the invention is not so limited. Rather, in another embodiment of the invention, a markerless motion detection/motion capture system is utilized. The markerless motion capture system uses a plurality of high speed video cameras to record the motion of a subject without requiring any markers to be placed on the subject. Both of the aforementioned marker and markerless motion detection/motion capture systems are optical-based systems. In one embodiment, the optical motion capture system utilizes visible light, while in another alternative embodiment, the optical motion capture system employs infrared light (e.g., the system could utilize an infrared (IR) emitter to project a plurality of dots onto objects in a particular space as part of a markerless motion capture system). For example, in one or more embodiments, the optical motion capture system may comprise a motion capture device with one or more cameras, one or more infrared (IR) depth sensors, and one or more microphones, which may be used to provide full-body three-dimensional (3D) motion capture, facial recognition, and voice recognition capabilities. It is also to be understood that, rather than using an optical motion detection/capture system, a suitable magnetic or electro-mechanical motion detection/capture system may also be employed to determine the position of the subject 42 on the instrumented treadmill 10.

In the illustrative embodiment, the cameras 38 depicted in FIG. 1 may be in the form of infrared-type (IR) or near infrared-type (NIR) cameras having an angular field of view range between approximately 40 degrees and approximately 80 degrees (or between 40 degrees and 80 degrees). More particularly, in one or more embodiments, the angular field of view range of the cameras 38 may be between approximately 50 degrees and approximately 70 degrees (or between 50 degrees and 70 degrees). Also, in one or more exemplary embodiments, the cameras 38 depicted in FIG. 1 may have a resolution of approximately 1.0 Megapixels, a maximum frame rate of approximately 250 feet per second (fps), and a 4 millimeter to 12 millimeter (4-12 mm) zoom lens. The cameras 38 are positioned in the gait perturbation system 100 of FIG. 1 so that each marker disposed on a subject 42 standing on the instrumented treadmill 10 is captured by at least two (2) of the cameras 38, and preferably, three (3) of the cameras 38.

Now, referring to FIG. 4, another manner in which the data acquisition/data processing device 28 may determine a position of a body portion (e.g., torso, pelvis, or head) of the subject 42 will be described. In particular, the data acquisition/data processing device 28 may also determine the position of the body portion of the subject 42 by utilizing the inertial measurement units (IMUs) 48 illustrated in FIG. 4. As shown in this figure, a subject 42 may be outfitted with a plurality of different inertial measurement units 48 for detecting motion. In the illustrative embodiment, the subject 42 is provided with two (2) inertial measurement units 48 on each of his legs (e.g., on the side or front of his legs). The subject 42 is also provided with two (2) inertial measurement units 48 on each of his arms (e.g., on the side of his arms). In addition, the subject 42 of FIG. 4 is provided with an inertial measurement unit 48 above his waist, and another inertial measurement unit 48 around his or her chest (e.g., near his sternum). In the illustrated embodiment, each of the inertial measurement units 48 is operatively coupled to the data acquisition/data processing device 28 by wireless means, such as Bluetooth, or another suitable type of personal area network wireless means.

In the illustrated embodiment of FIG. 4, each of the inertial measurement units 48 is coupled to the respective body portion of the subject 42 by a band 50. As shown in FIG. 4, each of the inertial measurement units 48 comprises an IMU housing attached to an elastic band 50. The band 50 is resilient so that it is capable of being stretched while being placed on the subject 42 (e.g., to accommodate the hand or the foot of the subject 42 before it is fitted in place on the arm or the leg of the subject 42). The band 50 can be formed from any suitable stretchable fabric, such as neoprene, spandex, and elastane. Alternatively, the band 50 could be formed from a generally non-stretchable fabric, and be provided with latching means or clasp means for allowing the band 50 to be split into two portions (e.g., the band 50 could be provided with a snap-type latching device).

In other embodiments, it is possible to attach the inertial measurement units 48 to the body portions of the subject 42 using other suitable attachment means. For example, the inertial measurement units 48 may be attached to a surface (e.g., the skin or clothing item) of the subject 42 using adhesive backing means. The adhesive backing means may comprise a removable backing member that is removed just prior to the inertial measurement unit 48 being attached to a subject 42 or object. Also, in some embodiments, the adhesive backing means may comprise a form of double-sided bonding tape that is capable of securely attaching the inertial measurement unit 48 to the subject 42 or another object.

In one or more embodiments, each inertial measurement unit 48 may comprise a triaxial (three-axis) accelerometer sensing linear acceleration $\vec{a}'$, a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer. In addition, each inertial measurement unit 48 may comprise a wireless data interface for electrically coupling the inertial measurement unit 48 to the data acquisition/data processing device 28.

Next, an illustrative manner in which the data acquisition/data processing device 28 of the gait perturbation system 100 performs the inertial measurement unit (IMU) calculations will be explained in detail. In particular, this calculation procedure will describe the manner in which the orientation and position of one or more body portions (e.g., torso or limbs) of the subject 42 could be determined using the signals from the plurality of inertial measurement units (IMUs) 48 of the motion detection system of FIG. 4. As explained above, in one or more embodiments, each inertial measurement unit 48 includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector $\vec{n}'$. Each inertial measurement unit 48 senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement units (IMUs) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\omega}(t)dt \quad (2)$$

$$\vec{\theta}(t) = \vec{\theta}_0 + \int_0^t \vec{\Theta}(t)\vec{\omega}'(t)dt \quad (3)$$

where $\vec{\Theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\} dt \quad (4)$$

$$\vec{v}(t) = \vec{v}_0 + \int_0^t \{\vec{\Theta}(t)[\vec{a}'(t) + 2\vec{\omega}' \times \vec{v}'(t)] - \vec{g}\} dt \quad (5)$$

where $2\vec{\omega} \times \vec{v}'(t)$ is the Coriolis term, and where the local linear velocity is given by the following equation:

$$\vec{v}'(t) = \vec{\Theta}^{-1}(t)\vec{v}(t) \quad (6)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t) dt \quad (7)$$

At the initial position, the IMU's local-to-global rotation's matrix has an initial value $\vec{\Theta}(0) = \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\vec{\Theta}_0(\vec{n}', \vec{n})$ that are unconstrained in one component of rotation. The $\vec{\Theta}_0(\vec{g}', \vec{n}', \vec{g}, \vec{n})$ has many implementations, with the common one being the Kabsch algorithm. As such, using the calculation procedure described above, the data acquisition/data processing device 28 of the gait perturbation system 100 may determine the orientation $\vec{\theta}(t)$ and position $\vec{R}(t)$ of one or more body portions of the subject 42. For example, the orientation of a limb of the subject 42 (e.g., the right arm of the subject 42 in FIG. 4) may be determined by computing the orientation $\vec{\theta}(t)$ and position $\vec{R}(t)$ of two points on the limb of the subject 42 (i.e., at the respective locations of two inertial measurement units (IMUs) 48 disposed on the limb of the subject 42).

As explained above, the inertial measurement units (IMUs) 48 of FIG. 4 sense measured quantities (i.e., acceleration, angular velocity) that are representative of the position of the body portion of the subject 42 and output a plurality of position data signals that are representative of the position of the body portion of the subject 42. The data acquisition/data processing device 28 is specially programmed to determine the position of the body portion of the subject 42 using the plurality of position data signals that are output by the plurality of inertial measurement units 48 (e.g., the plurality of position data signals from the inertial measurement units 48 may be used to determine the position of the subject 42 relative to the center of the treadmill belts 14, 16 or to approximate the subject's center-of-gravity along the y-axis).

Now, the manner in which the programmable logic controller 25 and data acquisition/data processing device 28 of the gait perturbation system 100 are specially programmed to perturb the gait of the subject 42 disposed on the instrumented treadmill 10 will be described. As explained above, the data acquisition/data processing device 28 is operatively coupled to the programmable logic controller 25 of the instrumented treadmill 10. In one illustrative embodiment, the programmable logic controller 25 (i.e., a data processing device) is specially programmed to generate a first base velocity signal for controlling the speed of the treadmill belts 14, 16 of the instrumented treadmill 10 and a second velocity signal for introducing a perturbation to the treadmill belts 14, 16. Also, in the illustrative embodiment, programmable logic controller 25 is specially programmed to combine the first base velocity signal with the second velocity signal to form a composite velocity signal, and to control the speed set points of the treadmill belts 14, 16 using the composite velocity signal such that the treadmill belts 14, 16 perturb a gait of the person. As described in detail hereinafter, in order to create perturbations, the frequency and the amplitude of the treadmill belt speed can be varied. In an alternative illustrative embodiment, the data acquisition/data processing device 28, rather than the programmable logic controller 25, may be specially programmed to generate the first base velocity signal for controlling the speed of the treadmill belts 14, 16 of the instrumented treadmill 10, to generate the second velocity signal for introducing a perturbation to the treadmill belts 14, 16, and to combine the first base velocity signal and the second velocity signal to form the composite velocity signal.

Figure 7:
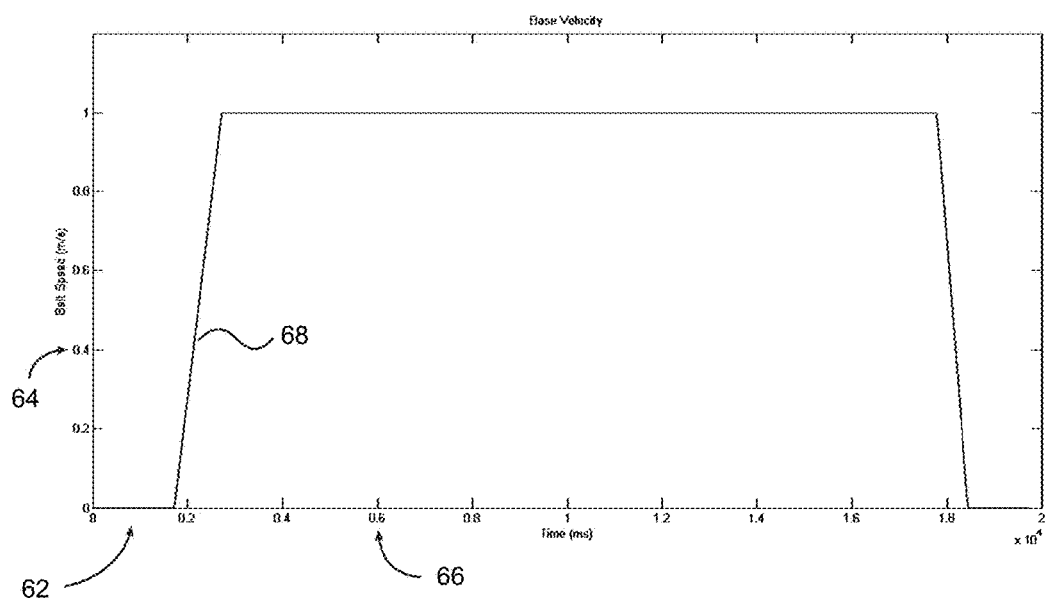
FIG. 7 is a graph illustrating a base velocity signal with no perturbations for controlling the speed set point of the one or more treadmill belts of the instrumented treadmill of FIG. 1.

An exemplary base velocity signal generated by the programmable logic controller 25 or the data acquisition/data processing device 28 for controlling the speed of the treadmill belts 14, 16 of the instrumented treadmill 10 is illustrated in the graph 62 of FIG. 7. As shown in this figure, the y-axis 64 of the graph 62 is the treadmill belt speed in meters per second (m/s), while the x-axis 66 of the graph 62 is the time in milliseconds (ms). In the graph 62 of FIG. 7, it can be seen that the base velocity curve 68 ramps up to 1.0 meters per second at approximately 2,000 milliseconds and then ramps back down to zero at approximately 18,000 milliseconds. In FIG. 7, no perturbations have been applied to the treadmill belts 14, 16.

In the illustrative embodiment, the second velocity signal for introducing a perturbation to the treadmill belts 14, 16 comprises a stochastic signal, and the programmable logic controller 25 or the data acquisition/data processing device 28 is specially programmed to add the stochastic signal to the base velocity signal so as to make the treadmill belts 14, 16 oscillate while the subject 42 is disposed thereon. As will be described hereinafter, the stochastic signal may be of uniform or normal distribution. As such, the stochastic signal is capable of simulating uneven terrain or slips and falls while the subject 42 is walking or running on the instrumented treadmill 10.

Figure 8:
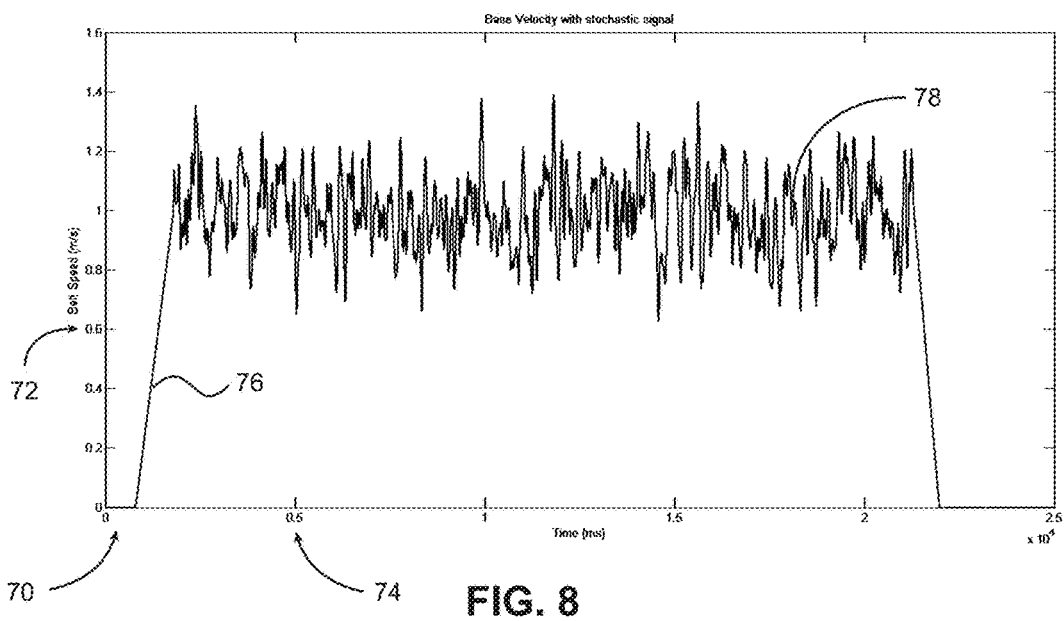
FIG. 8 is a graph illustrating a combined base velocity and stochastic signal for controlling the speed set point of the one or more treadmill belts of the instrumented treadmill of FIG. 1.

An exemplary combined base velocity and stochastic signal generated by the programmable logic controller 25 or the data acquisition/data processing device 28 for controlling the speed of the treadmill belts 14, 16 of the instrumented treadmill 10 is illustrated in the graph 70 of FIG. 8. As shown in this figure, the y-axis 72 of the graph 70 is the treadmill belt speed in meters per second (m/s), while the x-axis 74 of the graph 70 is the time in milliseconds (ms).

In the graph 70 of FIG. 8, it can be seen that the combined base velocity/stochastic signal curve comprises a base velocity curve portion 76 and stochastic signal curve portion 78. The base velocity curve portion 76 ramps up to 1.0 meters per second at approximately 2,000 milliseconds and then ramps down back to zero at approximately 22,000 milliseconds. In FIG. 8, the stochastic signal is added to the base velocity signal of 1.0 meters per second. As shown in FIG. 8, the combined base velocity and stochastic signal generated by the programmable logic controller 25 or the data acquisition/data processing device 28 is never negative, so the belts 14, 16 of the instrumented treadmill do not undergo a change in their rotational directions over time (i.e., because the velocity is always a positive value, the direction of the belts 14, 16 is not reversed in the exemplary signal of FIG. 8). As shown in FIG. 8, the amplitude of the stochastic signal curve portion 78 is randomly changing over time (i.e., the amplitude consistently changes over time in a random manner). Similarly, the frequency of the stochastic signal curve portion 78 is randomly changing over time (i.e., the frequency consistently changes over time in a random manner). Thus, advantageously, the programmable logic controller 25 or the data acquisition/data processing device 28 generates a stochastic signal with both a randomly varying amplitude and frequency that results in a random perturbation being delivered to the subject 42 on the instrumented treadmill 10. The manner of delivery of the perturbation to the subject 42 on the treadmill 10 is not just random, but rather the stochastic signal itself controlling the perturbation has both random amplitude and frequency content. Advantageously, the belt speed of the instrumented treadmill 10 does not have a constant slope that can be learned by the subject 42 over time. The stochastic signal generated by the programmable logic controller 25 or the data acquisition/data processing device 28 significantly changes the functionality of the instrumented treadmill 10 by enabling the instrumented treadmill 10 to simulate unexpected, real-life scenarios that could be encountered by the subject 42, such as slip and fall events. As such, controlling the treadmill 10 using the stochastic signal enables the instrumented treadmill 10 to model real-life conditions encountered by the subject 42 so that the testing and/or training of the subject 42 using the treadmill 10 may be greatly enhanced.

In the illustrative embodiment, the generation of the combined base velocity and stochastic signal by the programmable logic controller 25 or the data acquisition/data processing device 28 comprises a plurality of different steps. Initially, by utilizing the input devices 32, 36 of the data acquisition/data processing device 28 (e.g., the keyboard 32 and/or touchpad 36), a user enters the following input values: (i) the stochastic signal base amplitude, (ii) a frequency of the stochastic signal (i.e., the cut-off frequency of the stochastic signal), and (iii) a signal type of the stochastic signal (i.e., uniform or random). Then, the programmable logic controller 25 or the data acquisition/data processing device 28 generates the random or uniform stochastic signal based upon the amplitude and frequency values entered by the user. The amplitude value entered by the user determines the upper and lower bounds of the stochastic signal generated by the programmable logic controller 25 or the data acquisition/data processing device 28, while the cut-off frequency value entered by the user determines the upper frequency limit of the stochastic signal generated by the programmable logic controller 25 or the data acquisition/data processing device 28. Finally, the programmable logic controller 25 updates belt speed set point(s) of the treadmill belts 14, 16 of the instrumented treadmill 10. Each of these steps will be described in further detail hereinafter. Referring to FIG. 6, when the programmable logic controller 25 generates the stochastic signal, the base amplitude, the cut-off frequency, and the signal type of the stochastic signal are transmitted from the data acquisition/data processing device 28 to the programmable logic controller 25 so that the stochastic signal is able to be generated by the programmable logic controller 25.

In the illustrative embodiment, the user may be permitted to enter a stochastic amplitude value in the range between zero and approximately 2.0 meters, inclusive (or between zero and 2.0 meters, inclusive). If the user enters different amplitude values for each of the treadmill belts 14, 16, the difference in the two amplitude values may not exceed 1.0 meter in the illustrative embodiment. Similarly, in the illustrative embodiment, the user may be permitted to enter a cut-off frequency value in the range between zero and approximately 10 Hertz, inclusive (or between zero and 10 Hertz, inclusive). If the user enters different cut-off frequency values for each of the treadmill belts 14, 16, the difference in the cut-off frequency values may not exceed 5 Hertz in the illustrative embodiment. Also, in the illustrative embodiment, the amplitude has to be less than the base velocity (e.g., if the base velocity is 2.0 meters per second, then the amplitude needs to be less than 2.0 meters). In general, a low amplitude would simulate vibrations, while a high amplitude would imitate a slip condition.

In addition to entering the amplitude, cut-off frequency, and signal type of the stochastic signal, the user is also able to selectively regulate the beginning and end of the stochastic signal by pressing a graphical start button on the operator display 34 to initiate the stochastic signal, and then by subsequently pressing a graphical stop button on the operator display 34 to end the stochastic signal (i.e., when the display is a touchscreen).

Figure 9:
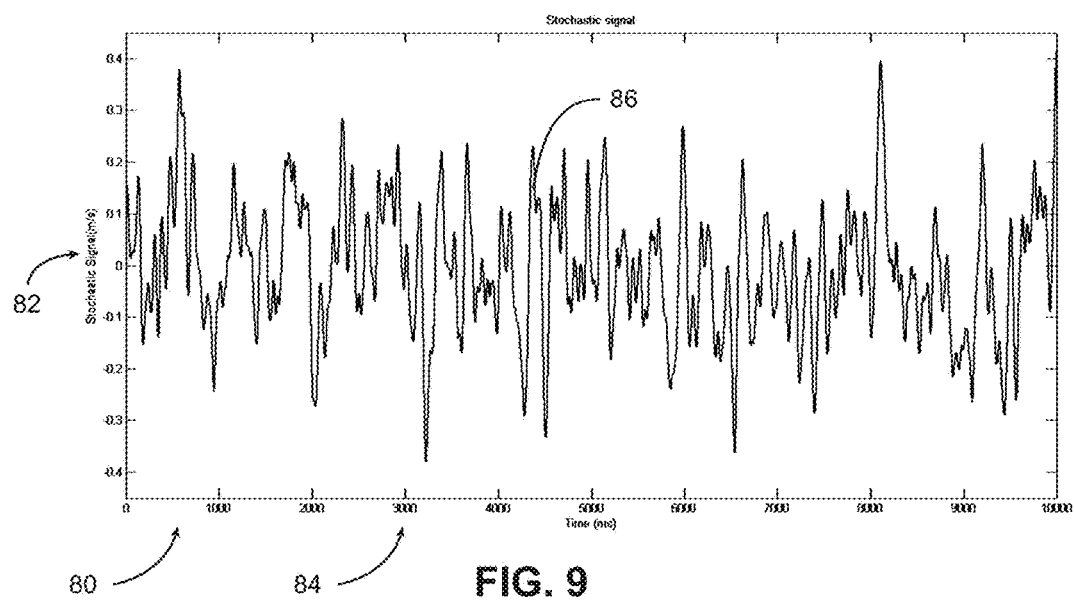
FIG. 9 is a graph illustrating a uniform stochastic signal with a base amplitude of 0.9 meters and a cutoff frequency of 5 Hertz.

In the illustrative embodiment, the belt speed of each belt 14, 16 of the instrumented dual belt treadmill 10 is capable of being updated independently. In the initial step of the process, as explained above, the user is allowed to input the amplitude of the stochastic signal, the frequency of the stochastic signal, and the stochastic signal type (i.e., either uniform or normal). The base amplitude that is input for the signal determines the range of the stochastic signal that is generated by the programmable logic controller 25 or the data acquisition/data processing device 28. For example, a first exemplary uniform stochastic signal generated by the programmable logic controller 25 or the data acquisition/data processing device 28 is illustrated in the graph 80 of FIG. 9. As shown in this figure, the y-axis 82 of the graph 80 is speed in meters per second (m/s), while the x-axis 84 of the graph 80 is the time in milliseconds (ms). The uniform stochastic signal curve 86 in FIG. 9 has a base amplitude of 0.9 meters and a cut-off frequency of 5 Hertz. In the graph 80 of FIG. 9, it can be seen that the uniform stochastic signal curve 86 oscillates between a minimum lower limit of approximately −0.40 meters per second and a maximum upper limit of approximately 0.40 meters per second over a time duration of approximately 10,000 milliseconds. As another example, a second exemplary uniform stochastic signal generated by the programmable logic controller 25 or the data acquisition/data processing device 28 is illustrated in the graph 88 of FIG. 10. As shown in this figure, the y-axis 90 of the graph 88 is speed in meters per second (m/s), while the x-axis 92 of the graph 88 is the time in milliseconds (ms). The uniform stochastic signal curve 94 in FIG. 10 has a base amplitude of 0.5 meters and a cut-off frequency of 5 Hertz.

Figure 10:
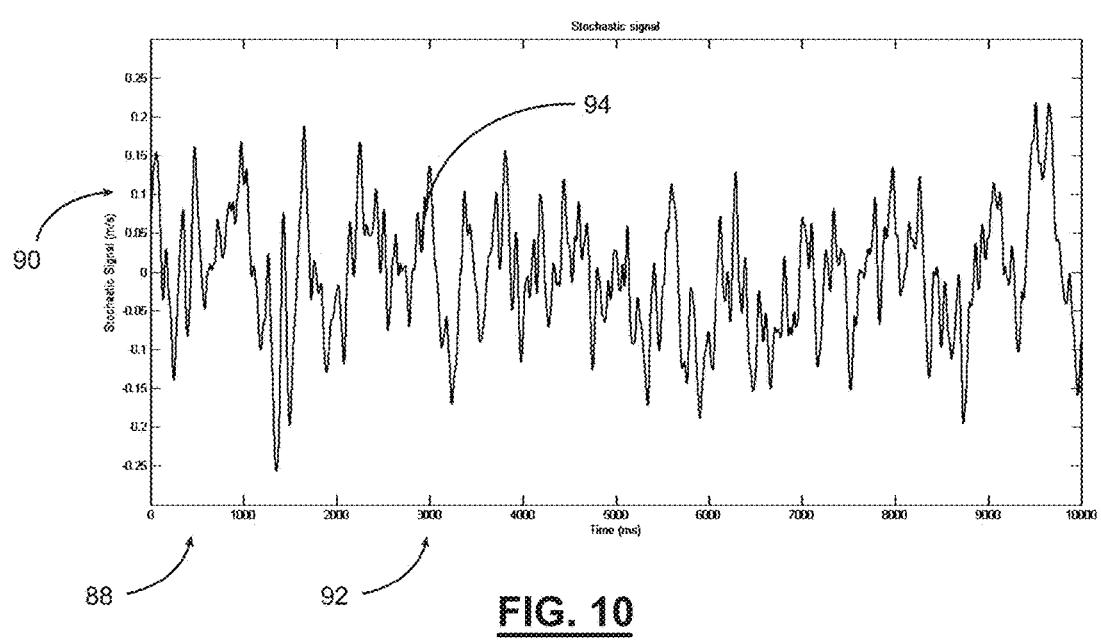
FIG. 10 is a graph illustrating a uniform stochastic signal with a base amplitude of 0.5 meters and a cutoff frequency of 5 Hertz.

In the graph 88 of FIG. 10, it can be seen that the uniform stochastic signal curve 94 oscillates between a minimum lower limit of approximately −0.25 meters per second and a maximum upper limit of approximately 0.225 meters per second over a time duration of approximately 10,000 milliseconds.

Figure 11:
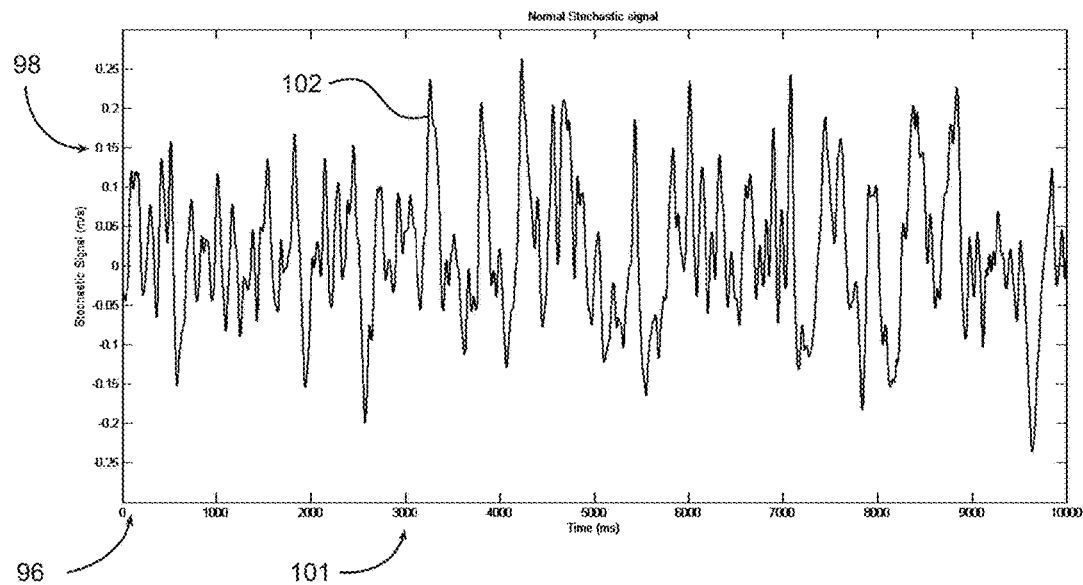
FIG. 11 is a graph illustrating a normal stochastic signal with a base amplitude of 0.9 meters and a cutoff frequency of 5 Hertz.
Figure 12:
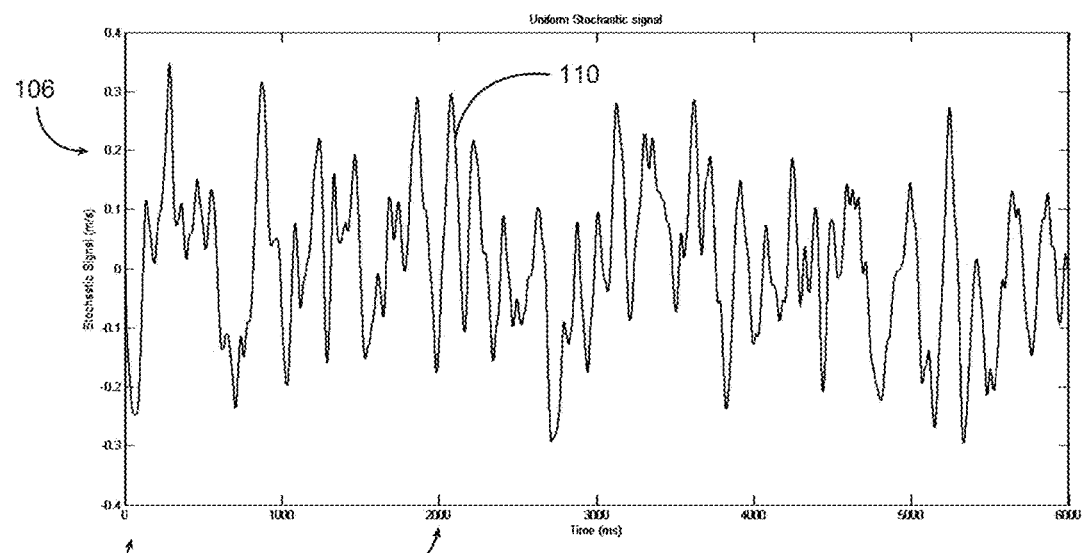
FIG. 12 is a graph illustrating a uniform stochastic signal with a base amplitude of 0.9 meters and a cutoff frequency of 10 Hertz.

As yet another example of a perturbation input signal, an exemplary normal stochastic signal generated by the programmable logic controller 25 or the data acquisition/data processing device 28 is illustrated in the graph 96 of FIG. 11. As shown in this figure, the y-axis 98 of the graph 96 is speed in meters per second (m/s), while the x-axis 101 of the graph 96 is the time in milliseconds (ms). The normal stochastic signal curve 102 in FIG. 11 has a base amplitude of 0.9 meters and a cut-off frequency of 5 Hertz. In the graph 96 of FIG. 11, it can be seen that the normal stochastic signal curve 102 oscillates between a minimum lower limit of approximately −0.25 meters per second and a maximum upper limit of approximately 0.25 meters per second over a time duration of approximately 10,000 milliseconds. As still another example, a third exemplary uniform stochastic signal generated by the programmable logic controller 25 or the data acquisition/data processing device 28 is illustrated in the graph 104 of FIG. 12. As shown in this figure, the y-axis 106 of the graph 104 is speed in meters per second (m/s), while the x-axis 108 of the graph 104 is the time in milliseconds (ms). The uniform stochastic signal curve 110 in FIG. 12 has a base amplitude of 0.9 meters and a cut-off frequency of 10 Hertz. In the graph 104 of FIG. 12, it can be seen that the uniform stochastic signal curve 110 oscillates between a minimum lower limit of approximately −0.30 meters per second and a maximum upper limit of approximately 0.36 meters per second over a time duration of approximately 6,000 milliseconds.

In the second step of the process, where a random uniform or normal random signal is generated by the programmable logic controller 25 or the data acquisition/data processing device 28 at the selected cut-off frequency, a random number function or subroutine may be used to generate the uniform signal random numbers (e.g., the DRAND function block in a TwinCAT software package). In the illustrative embodiment, the random number function utilized by the programmable logic controller 25 or the data acquisition/data processing device 28 requires an initial value input for the specification of the random number series. The output returns a pseudo-random number in the range −1.0 to 1.0 with double accuracy. That is, the random number function generates the same sequence of random numbers each time that the same seed is utilized. As such, in an exemplary embodiment, the seed value that is used for the random number function is acquired for each trial from the low DW of the system time, which gives a sufficiently random seed for each trial. That way, the programmable logic controller 25 or the data acquisition/data processing device 28 does not generate the same random number sequence or produce any other perturbation trends from trial to trial. In one or more embodiments, the operating system time stamp is a 64-bit integer value, with a precision of 100 nanoseconds (ns), which is updated with every call of the programmable logic controller (PLC) 25. In one or more embodiments, the low DW (timeLoDW) is the low-value 4 bytes of the time stamp and it changes very rapidly at rate of 0.01 milliseconds (ms). The random signal has a varying frequency. The randomness of the stochastic signal is highly advantageous because the subjects being tested on the instrumented treadmill 10 are not able to as easily learn how to overcome a slip-and-fall perturbation during a testing or training routine. If the perturbation employed was always the same, then eventually subjects would learn how to adapt to the perturbation, and the training would become less effective.

Figure 13:
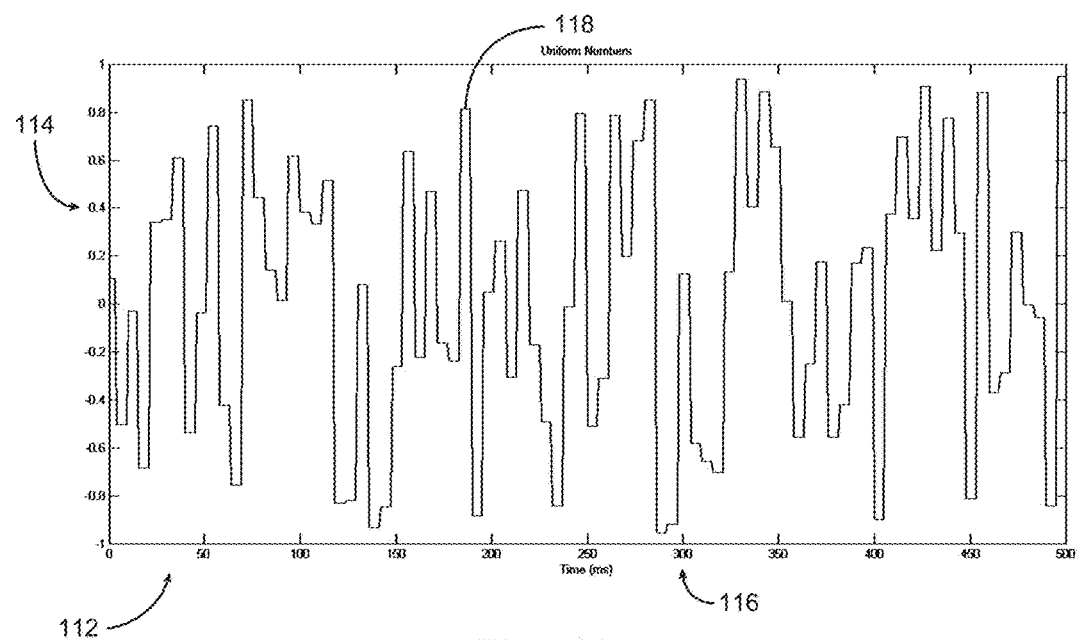
FIG. 13 is a graph illustrating a uniform random numbers curve generated by the data processing device of the gait perturbation system.

An exemplary uniform random numbers curve generated by the programmable logic controller 25 or data acquisition/data processing device 28 using a random number function or subroutine (e.g., DRAND function block) is illustrated in the graph 112 of FIG. 13. As shown in this figure, the y-axis 114 of the graph 112 is the random number value (dimensionless), while the x-axis 116 of the graph 112 is the time in milliseconds (ms). In the graph 112 of FIG. 13, it can be seen that the uniform random numbers curve 118 comprises a plurality of random number values between a lower limit value of approximately −0.95 and an upper limit value of approximately 0.90.

When the user selects a uniform-type stochastic signal, a uniform random numbers curve, such as that depicted in FIG. 13, is used for controlling the speed set points of the belts 14, 16 of the instrumented dual belt treadmill 10. However, if the user alternatively selects a normal-type stochastic signal, two (2) uniform signals U1 and U2 generated using the random number function are converted into normal signal N using the following Box-Muller transform equation:

$$N = \sqrt{-2\ln U1}\cos(2\pi U2) \tag{8}$$

Figure 14:
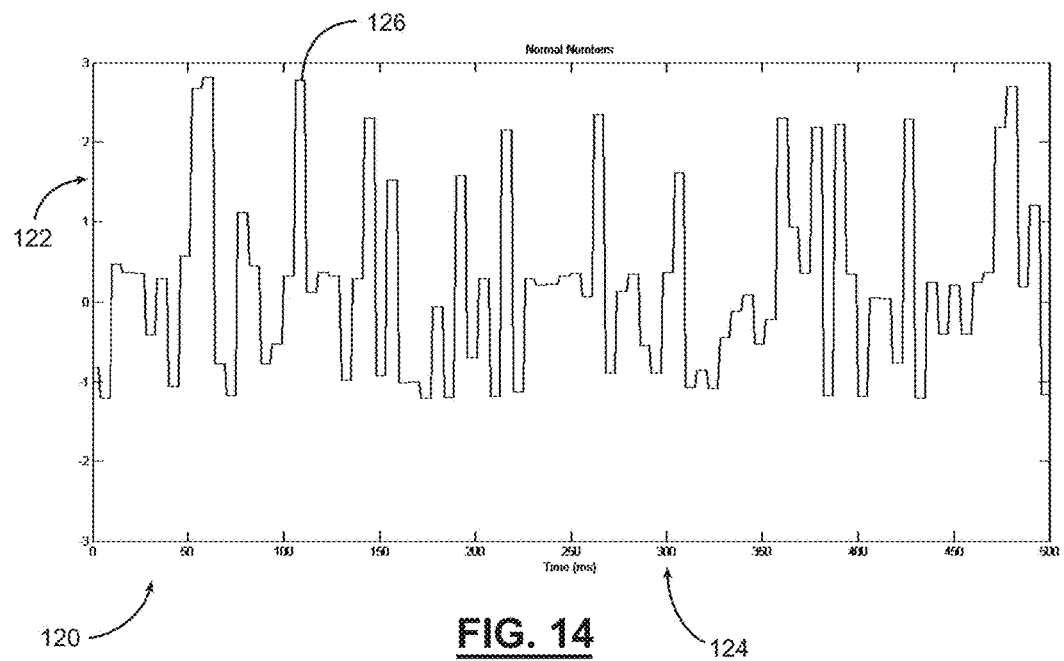
FIG. 14 is a graph illustrating a normal random numbers curve generated by the data processing device of the gait perturbation system.

An exemplary normal random numbers curve generated by the programmable logic controller 25 or the data acquisition/data processing device 28 using equation (8) to perform a Box-Muller transformation is illustrated in the graph 120 of FIG. 14. As shown in this figure, the y-axis 122 of the graph 120 is the random number value (dimensionless), while the x-axis 124 of the graph 120 is the time in milliseconds (ms). In the graph 120 of FIG. 14, it can be seen that the normal random numbers curve 126 comprises a plurality of random number values between a lower limit value of approximately −1.2 and an upper limit value of approximately 2.8. The random variables illustrated in FIG. 14 are generated in the interval [3, −3].

Figure 15:
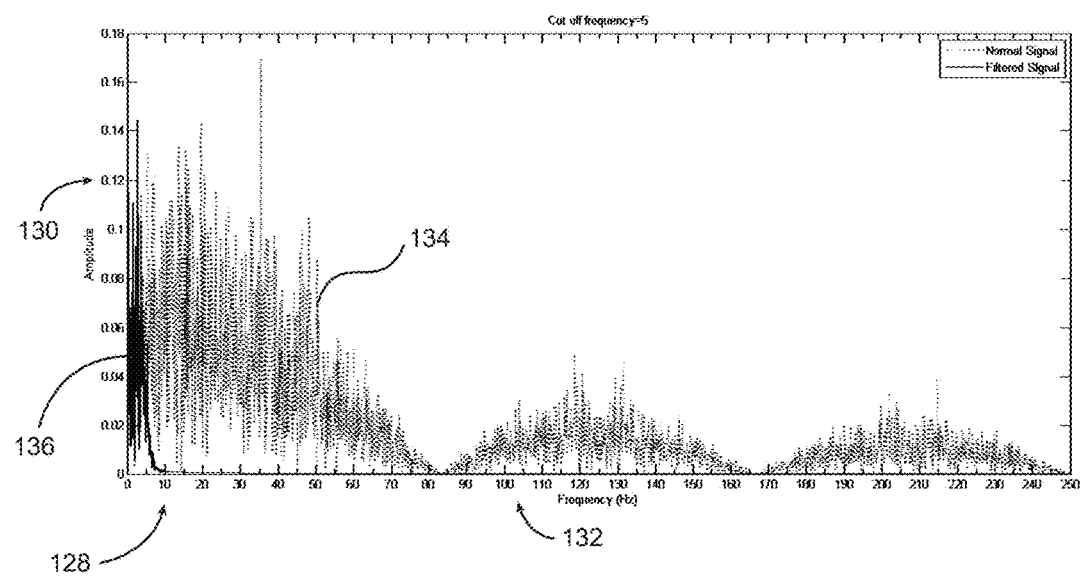
FIG. 15 is a graph illustrating a normal signal curve and filtered data curve at a cut-off frequency of 5 Hertz.
Figure 16:
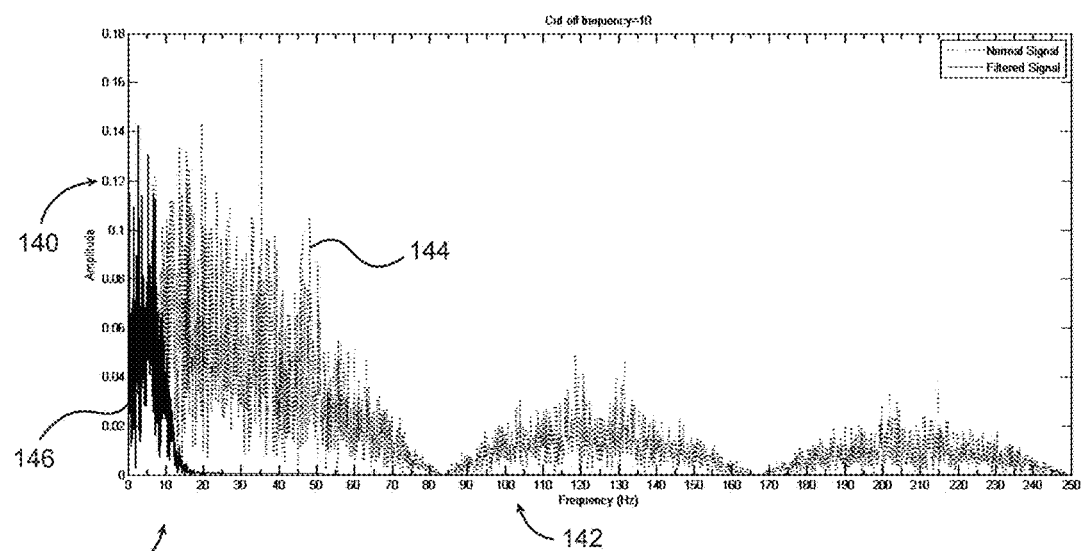
FIG. 16 is a graph illustrating a normal signal curve and filtered data curve at a cut-off frequency of 10 Hertz.

In the illustrative embodiment, the uniform or normal signal is then passed through a fourth order low pass Butterworth filter to limit the frequency component of the signal at a user specified value (i.e., at the frequency entered by the user). For example, a first exemplary filtered signal generated by the programmable logic controller 25 or the data acquisition/data processing device 28 is illustrated in the graph 128 of FIG. 15. As shown in this figure, the y-axis 130 of the graph 128 is the amplitude value of the signal (dimensionless), while the x-axis 132 of the graph 128 is the frequency of the signal in Hertz (Hz). In the graph 128 of FIG. 15, the unfiltered normal signal curve 134 is indicated using a dashed line, while the filtered normal signal curve 136 is indicated using a solid line. In FIG. 15, a cut-off frequency of 5 Hertz is used in order to generally filter out the frequency content of the normal signal curve 134 which has a frequency of greater than 5 Hertz. As such, the frequency content of the normal signal curve used for controlling the perturbation of the instrumented treadmill 10 is generally limited to the user-specified frequency of 5 Hertz in FIG. 15. As another example, a second exemplary filtered signal generated by the programmable logic controller 25 or the data acquisition/data processing device 28 is illustrated in the graph 138 of FIG. 16. As shown in this figure, the y-axis 140 of the graph 138 is the amplitude value of the signal (dimensionless), while the x-axis 142 of the graph 138 is the frequency of the signal in Hertz (Hz). In the graph 138 of FIG. 16, the unfiltered normal signal curve 144 is indicated using a dashed line, while the filtered normal signal curve 146 is indicated using a solid line. In FIG. 16, a cut-off frequency of 10 Hertz is used in order to generally filter out the frequency content of the normal signal curve 144 which has a frequency of greater than 10 Hertz. As such, the frequency content of the normal signal curve used for controlling the perturbation of the instrumented treadmill 10 is generally limited to the user-specified frequency of 10 Hertz in FIG. 16.

Figure 17:
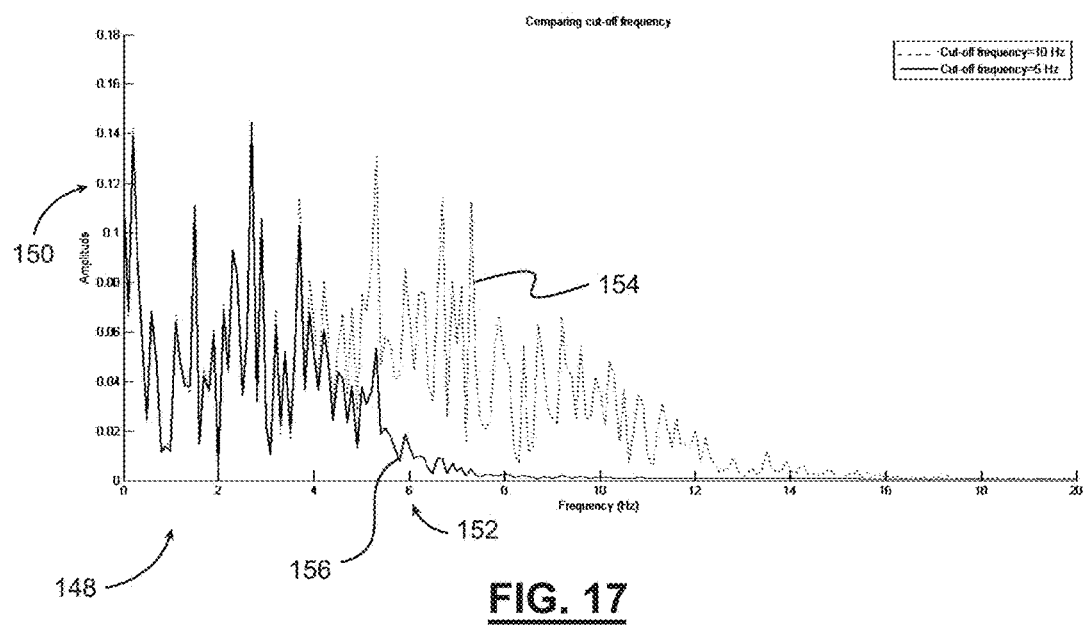
FIG. 17 is a graph comparing filtered data curves with cut-off frequencies of 5 Hertz and 10 Hertz.

Turning to FIG. 17, it can be seen that a graph 148 comparing the filtered data with cut-off frequencies of 5 Hertz and 10 Hertz is illustrated therein. Similar to FIGS. 15 and 16 described above, the y-axis 150 of the graph 148 depicted in FIG. 17 is the amplitude value of the signal (dimensionless), while the x-axis 152 of the graph 148 is the frequency of the signal in Hertz (Hz). In the graph 148 of FIG. 17, the filtered data curve 156 with a cut-off frequency of 5 Hertz is indicated using a solid line, while the filtered data curve 154 with a cut-off frequency of 10 Hertz is indicated using a dashed line.

In the illustrative embodiment, prior to the third step of the process, where the programmable logic controller 25 or the data acquisition/data processing device 28 updates belt speed set point(s) of the treadmill belts 14, 16 of the instrumented treadmill 10, the filtered signal is multiplied by the user-specified amplitude value so as to generate the stochastic signal for updating the belt speed set point(s). When the uniform-type stochastic signal is selected by the user, the uniform stochastic signal for updating the belt speed set point(s) is determined by the programmable logic controller 25 or the data acquisition/data processing device 28 in accordance with the following equation:

$$\text{Uniform stochastic signal} = \text{filtered uniform signal} * \text{Amplitude} \qquad (9)$$

Thus, in accordance with equation (9) above, the uniform stochastic signal is a function of the filtered, randomly-generated uniform signal and the user-specified amplitude value. More specifically, the programmable logic controller 25 or the data acquisition/data processing device 28 determines the uniform stochastic signal by computing the multiplicative product between the filtered uniform signal and the user-specified amplitude value. Alternatively, when the normal-type stochastic signal is selected by the user, the normal stochastic signal for updating the belt speed set point(s) is determined by the programmable logic controller 25 or the data acquisition/data processing device 28 in accordance with the following equation:

$$\text{Normal stochastic signal} = \text{filtered normal signal} * \text{Amplitude}/3 \qquad (10)$$

Thus, in accordance with equation (10) above, the normal stochastic signal is a function of the filtered, normalized randomly-generated uniform signal and the user-specified amplitude value. More specifically, the programmable logic controller 25 or the data acquisition/data processing device 28 determines the normal stochastic signal by computing the multiplicative product between the filtered normal signal and one-third of the user-specified amplitude value.

In one or more embodiments, the aforedescribed belt speed calculations are specially programmed on an embedded computer (e.g., the programmable logic controller 25 or the data acquisition/data processing device 28) that provides a deterministic program cycle time of 1 milliseconds (ms). In other words, the belt speed update rate of 1 kilohertz (kHz) is guaranteed by either the hardware architecture of the embedded computer or a real-time operating system (e.g., firmware) that runs on it. In these one or more embodiments, the updated belt speed set points are sent to a servo controller (i.e., actuator control drive 27), which controls the belt motor speed with a closed-loop rate of 4 kilohertz (kHz). In these one or more embodiments, the firmware of the instrumented treadmill 10 controls the treadmill belt perturbations.

In the illustrative embodiment, the programmable logic controller 25 or the data acquisition/data processing device 28 may be specially programmed so as to enable the belts 14, 16 of the instrumented treadmill 10 to be controlled in two different modes: (i) a dual stochastic mode, and (ii) independent left/right stochastic mode. In the dual stochastic mode, the programmable logic controller 25 or the data acquisition/data processing device 28 controls the speed set point of each of the treadmill belts 14, 16 using the same combined base velocity and stochastic signal so that the belts 14, 16 rotate together in unison. In the independent left/right stochastic mode, the programmable logic controller 25 or the data acquisition/data processing device 28 controls the speed set point of each of the treadmill belts 14, 16 using different combined base velocity and stochastic signals so that the belts 14, 16 do not rotate together (i.e., the belt speed set point of the left belt 14 is controlled independently from the belt speed set point of the right belt 16).

In a further embodiment, the programmable logic controller 25 or the data acquisition/data processing device 28 may be specially programmed to additionally control the belts 14, 16 of the instrumented treadmill 10 in a pulsed mode of operation. In the pulsed operation mode, the belts 14, 16 of the instrumented treadmill 10 are displaced from an initial stationary position (i.e., the belts 14, 16 undergo pure translation from a standstill position). In the pulsed mode of operation, the maximum pulse distance may be approximately 1.25 meters (or 1.25 m), the maximum pulse velocity may be approximately 6.5 meters per second (or 6.5 m/s), the maximum pulse acceleration may be approximately 10.0 meters per second squared (or 10 m/s$^2$), the maximum pulse deceleration may be approximately 10.0 meters per second squared (or 10 m/s$^2$), the maximum difference in the pulse distance between the treadmill belts 14, 16 may be approximately 1.0 meter (or 1 m), the maximum difference in the pulse velocity between the treadmill belts 14, 16 may be approximately 5.5 meters per second (or 5.5 m/s), the maximum difference in the pulse acceleration between the treadmill belts 14, 16 may be approximately 9.0 meters per second squared (or 9.0 m/s$^2$), and the maximum difference in the pulse deceleration between the treadmill belts 14, 16 may be approximately 9.0 meters per second squared (or 9.0 m/s$^2$).

Figure 18:
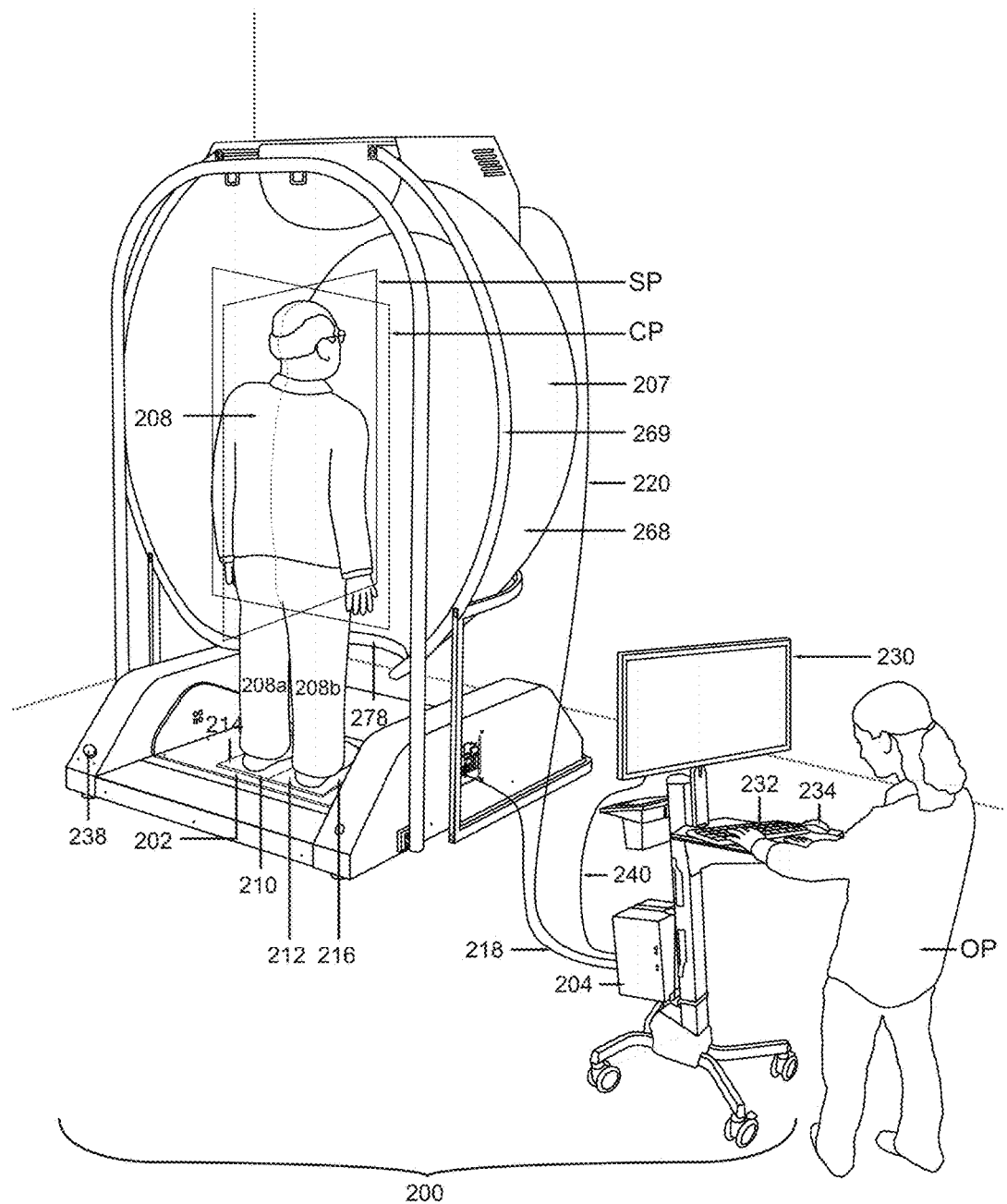
FIG. 18 is a perspective view of a balance perturbation system with a balance perturbation device in the form of a displaceable force measurement assembly, according to a second embodiment of the invention.

An illustrative embodiment of a balance perturbation system is seen generally at 200 in FIG. 18. In the second illustrative embodiment, the balance perturbation system 200 generally comprises a force measurement assembly 202 that is operatively coupled to a data acquisition/data processing device 204 (i.e., a data acquisition and processing device or computing device that is capable of collecting, storing, and processing data), which in turn, is operatively coupled to a subject visual display device 207 and an operator visual display device 230. As illustrated in FIG. 18, the force measurement assembly 202 is configured to receive a subject 208 thereon, and is capable of measuring the forces and/or moments applied to its substantially planar measurement surfaces 214, 216 by the subject 208.

As shown in FIG. 18, the data acquisition/data processing device 204 includes a plurality of user input devices 232, 234 connected thereto. Preferably, the user input devices 232, 234 comprise a keyboard 232 and a mouse 234. In addition, the operator visual display device 230 may also serve as a user input device if it is provided with touch screen capabilities. While a desktop-type computing system is depicted in FIG. 18, one of ordinary of skill in the art will appreciate that another type of data acquisition/data processing device 204 can be substituted for the desktop computing system such as, but not limited to, a laptop or a palmtop computing device (i.e., a PDA).

Referring again to FIG. 18, it can be seen that the force measurement assembly 202 of the second illustrated embodiment is in the form of a displaceable, dual force plate assembly. The displaceable, dual force plate assembly includes a first plate component 210, a second plate component 212, at least one force measurement device (e.g., a force transducer) associated with the first plate component 210, and at least one force measurement device (e.g., a force transducer) associated with the second plate component 212. In the illustrated embodiment, a subject 208 stands in an upright position on the force measurement assembly 202 and each foot of the subject 208 is placed on the top surfaces 214, 216 of a respective plate component 210, 212 (i.e., one foot on the top surface 214 of the first plate component 210 and the other foot on the top surface 216 of the second plate component 212). The at least one force transducer associated with the first plate component 210 is configured to sense one or more measured quantities and output one or more first signals that are representative of forces and/or moments being applied to its measurement surface 214 by the left foot/leg 208a of the subject 208, whereas the at least one force transducer associated with the second plate component 212 is configured to sense one or more measured quantities and output one or more second signals that are representative of forces and/or moments being applied to its measurement surface 216 by the right foot/leg 208b of subject 208. In one or more embodiments, when the subject is displaced on the force measurement assembly 202, the subject 208 generally does not move relative to the displaceable force measurement assembly 202 (i.e., the subject 208 and the force measurement assembly 202 generally move together in synchrony). Also, in one or more embodiments, the top surfaces 214, 216 of the respective plate components 210, 212 are not rotated underneath the feet of the subject 208, but rather remain stationary relative to the feet of the subject 208 (i.e., the top surfaces 214, 216 are displaced in generally the same manner as the feet of the subject).

In one non-limiting, exemplary embodiment, the force plate assembly 202 has a load capacity of up to approximately 500 lbs. (up to approximately 2,224 N) or up to 500 lbs. (up to 2,224 N). Advantageously, this high load capacity enables the force plate assembly 202 to be used with almost any subject requiring testing on the force plate assembly 202. Also, in one non-limiting, exemplary embodiment, the force plate assembly 202 has a footprint of approximately eighteen (18) inches by twenty (20) inches. However, one of ordinary skill in the art will realize that other suitable dimensions for the force plate assembly 202 may also be used.

Figure 19:
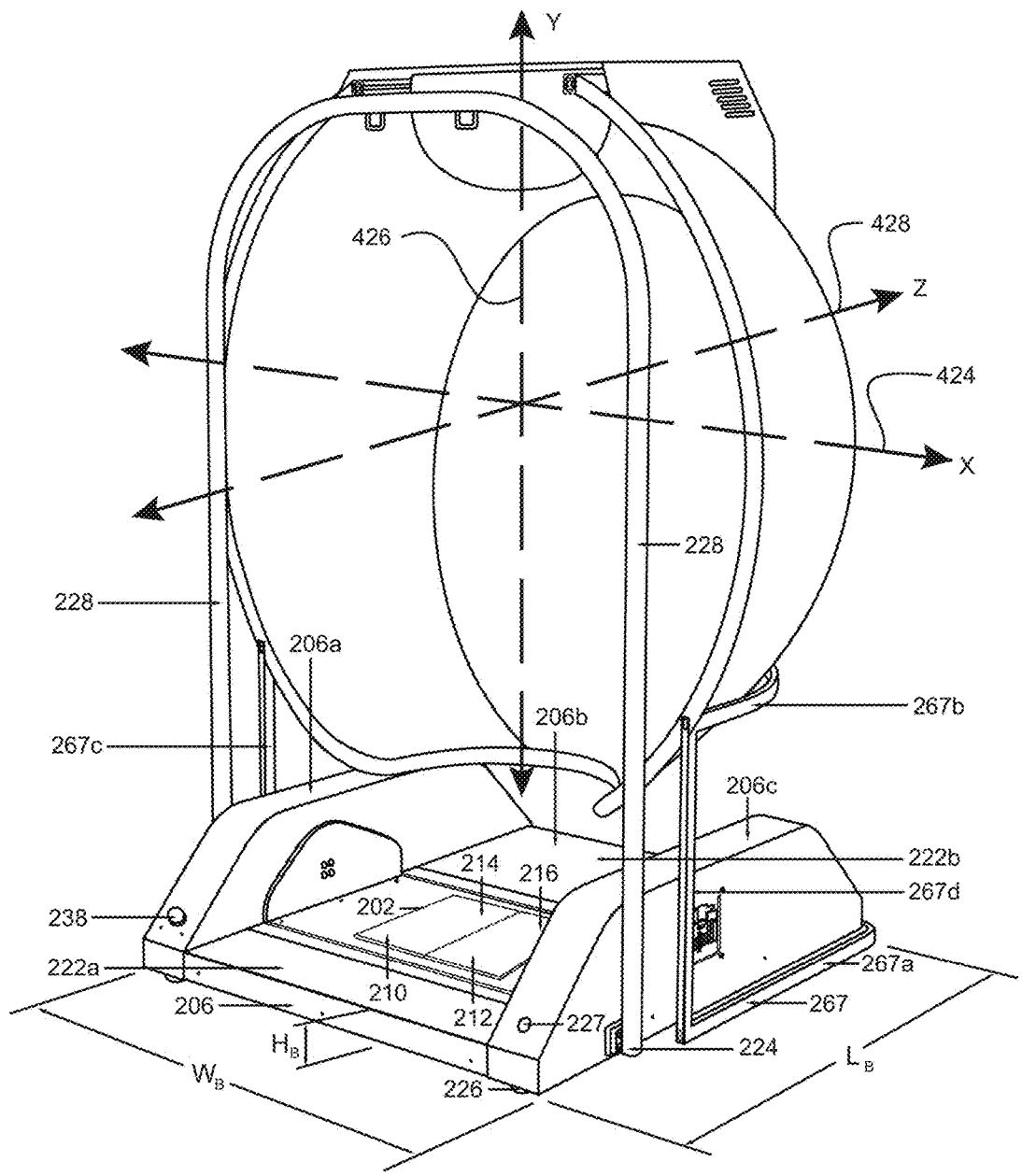
FIG. 19 is a perspective view of an immersive subject visual display device, a base assembly, and displaceable force measurement assembly of the balance perturbation system of FIG. 18.

Now, with reference to FIG. 19, it can be seen that the displaceable force measurement assembly 202 is movably coupled to a base assembly 206. The base assembly 206 generally comprises a substantially planar center portion 206b with two spaced-apart side enclosures 206a, 206c that are disposed on opposed sides of the center portion 206b. As shown in FIG. 19, the displaceable force measurement assembly 202 is recessed-mounted into the top surface of the center portion 206b of the base assembly 206 (i.e., it is recess-mounted into the top surface of the translatable sled assembly 256 which is part of the center portion 206b of the base assembly 206) so that its upper surface lies substantially flush with the adjacent stationary top surfaces 222a, 222b of the center portion 206b of the base assembly 206. The upper surface of the displaceable force measurement assembly 202 also lies substantially flush with the top surface of the translatable sled assembly 256. Moreover, in the illustrated embodiment, it can be seen that the base assembly 206 further includes a pair of mounting brackets 224 disposed on the outward-facing side surfaces of each side enclosure 206a, 206c. Each mounting bracket 224 accommodates a respective support rail 228. The support rails 228 can be used for various purposes related to the balance perturbation system 200. For example, the support rails 228 can be used for supporting a safety harness system, which is worn by the subject during testing so as to prevent injury.

Referring again to FIG. 19, each side enclosure 206a, 206c houses a plurality of electronic components that generate a significant amount of waste heat that requires venting. Because the bottom of each side enclosure 206a, 206c is substantially open, the waste heat is vented through the bottom thereof. In FIG. 19, it can be seen that the side enclosure 206a comprises an emergency stop switch 238 (E-stop) provided in the rear, diagonal panel thereof. In one embodiment, the emergency stop switch 238 is in the form of a red pushbutton that can be easily pressed by a user of the balance perturbation system 200 in order to quasi-instantaneously stop the displacement of the force measurement assembly 202. As such, the emergency stop switch 238 is a safety mechanism that protects a subject disposed on the displaceable force measurement assembly 202 from potential injury.

Figure 20:
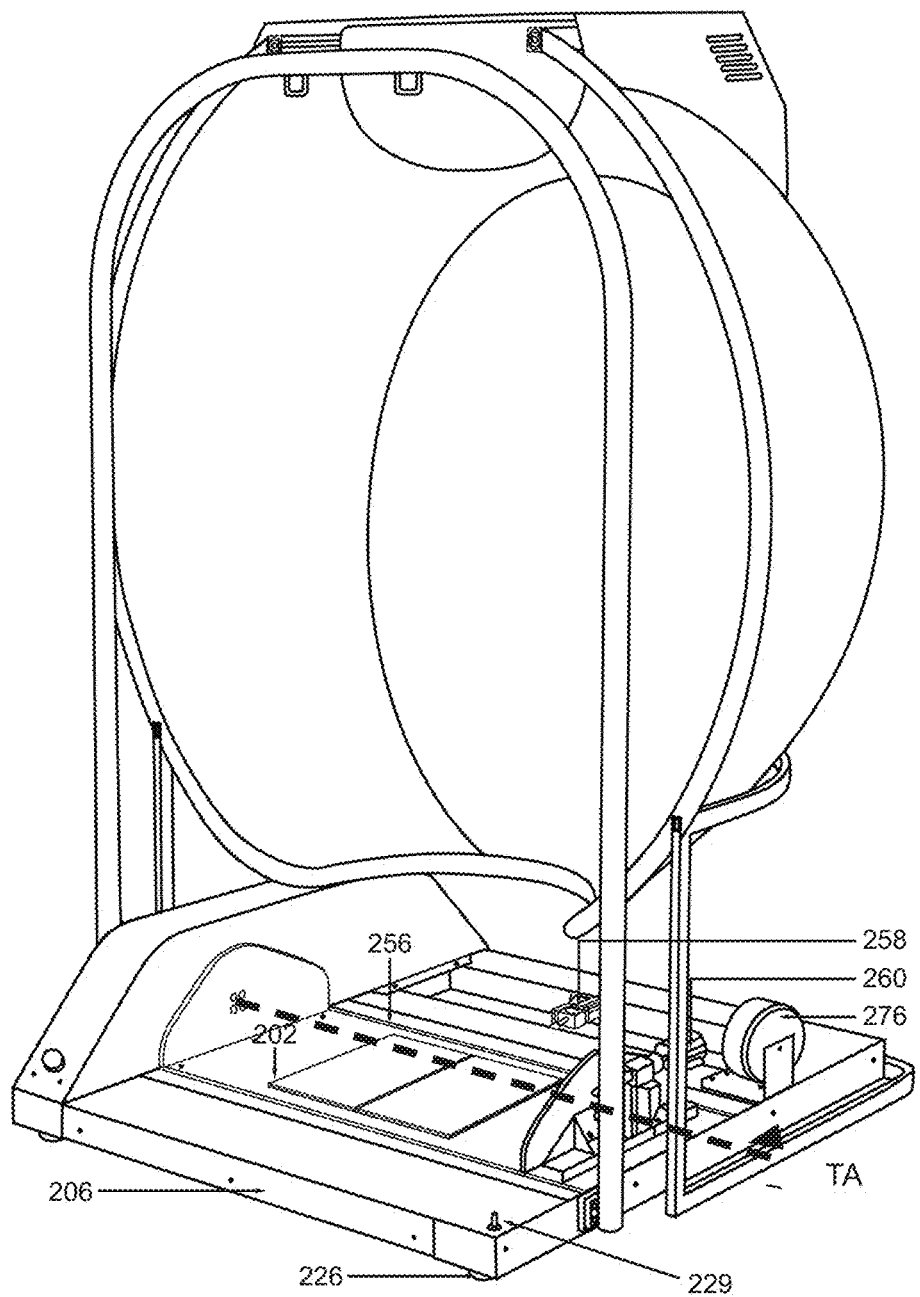
FIG. 20 is a perspective view of an immersive subject visual display device and a cutaway perspective view of a base assembly and displaceable force measurement assembly of the balance perturbation system of FIG. 18, wherein several covers of the base assembly are removed.

Next, turning to FIG. 20, the drive components of the base assembly 206 will be described in detail. Initially, the actuator system for producing the translation of the force measurement assembly 202 will be explained. In FIG. 20, the front top cover of the center portion 206b of the base assembly 206 has been removed to reveal the translation drive components. As shown in this figure, the force measurement assembly 202 is rotatably mounted to a translatable sled assembly 256. The translatable sled assembly 256 is displaced forward and backward (i.e., in directions generally parallel to the sagittal plane SP of the subject (see e.g., FIG. 18) disposed on the force measurement assembly 202) by means of a first actuator assembly 258. That is, the first actuator assembly 258 moves the translatable sled assembly 256 backwards and forwards, without any substantial rotation or angular displacement (i.e., the first actuator assembly 258 produces generally pure translational movement). In the illustrated embodiment, the first actuator assembly 258 is in the form of ball screw actuator, and includes an electric motor that drives a rotatable screw shaft which, in turn, is threadingly coupled to a nut fixedly secured to the translatable sled assembly 256. As such, when the screw shaft of the first actuator assembly 258 is rotated by the electric motor, the translatable sled assembly is displaced forward and backward along a substantially linear path. The electric motor of the first actuator assembly 258 is operatively coupled to a gear box (e.g., a 4:1 gear box) which, in turn, drives the rotatable screw shaft. Advantageously, because the nut of the ball screw actuator runs on ball bearings, friction is minimized and the actuator assembly 258 is highly efficient. However, an undesirable consequence of the highly efficient ball screw actuator design is its back-driveability. This poses a potential safety hazard to a subject disposed on the displaceable force measurement assembly 202 because the force plate could inadvertently move when a subject's weight is applied thereto. In order to prevent the force measurement assembly 202 from inadvertently being translated, the first actuator assembly 258 is additionally provided with a brake assembly disposed adjacent to the electric motor thereof. The brake assembly of the first actuator assembly 258 prevents any unintentional translation of the force measurement assembly 202.

Figure 21:
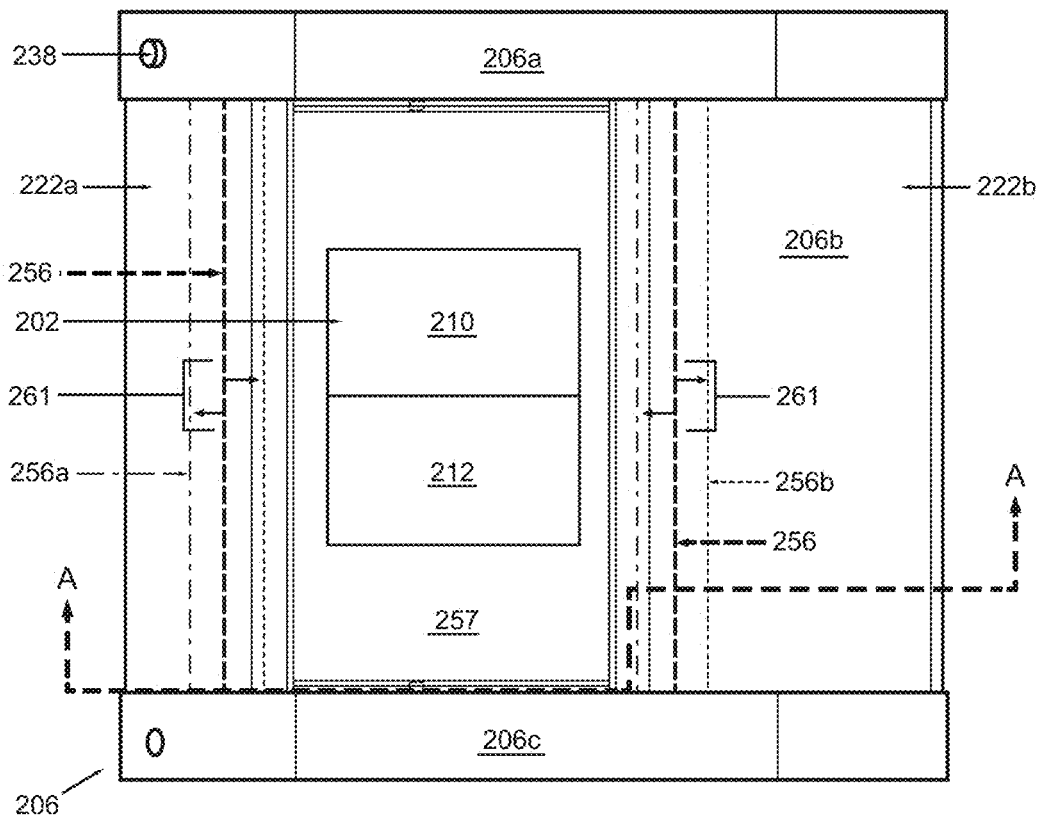
FIG. 21 is a top view of the base assembly illustrated in FIGS. 19 and 20, according to the second embodiment of the invention.
Figure 22:
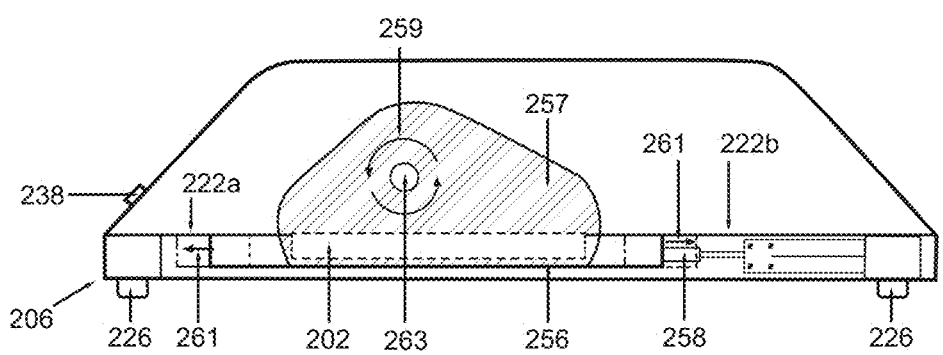
FIG. 22 is a longitudinal section cut through the base assembly illustrated in FIG. 21, wherein the section is cut along the cutting plane line A-A in FIG. 21, according to the second embodiment of the invention.

In FIG. 21, a top view of the base assembly 206 is illustrated, while in FIG. 22, a longitudinal cross-sectional view of the base assembly 206 is illustrated. As shown in FIGS. 21 and 22, the force measurement assembly 202 is mounted on a rotatable carriage assembly 257 (i.e., a swivel frame 257). The rotatable carriage assembly 257 is mounted to, and rotates relative to, the translatable sled assembly 256 (i.e., the translatable frame 256). The rotatable carriage assembly 257 is rotated by a second actuator assembly 260 (see FIG. 20) about a rotational shaft 263 (see FIG. 22—the rotatable carriage assembly 257 is provided with diagonal hatching thereon). As indicated by the curved arrows 259 in FIG. 22, the rotatable carriage assembly 257 is capable of either clockwise or counter-clockwise rotation about the transverse rotational axis TA in FIG. 20 (i.e., generally single degree-of-freedom rotation about the transverse axis TA). In contrast, as indicated by the straight arrows 261 in FIGS. 21 and 22, the translatable sled assembly 256 is capable of forward and backward translational movement by virtue of being linearly displaced by first actuator assembly 258. In FIGS. 21 and 22, a rearwardly displaced position 256a of the translatable sled assembly 256 is indicated using center lines, while a forwardly displaced position 256b of the translatable sled assembly 256 is indicated using dashed lines with small dashes.

Again, referring to FIG. 20, the actuator system for producing the rotation of the force measurement assembly 202 will now be described. In FIG. 20, the top cover of the side enclosure 206c of the base assembly 206 has been removed to reveal the rotational drive components. The force measurement assembly 202 is rotated within the translatable sled assembly 256 by the second actuator assembly 260. Like the first actuator assembly 258, the second actuator assembly 260 is also in the form of ball screw actuator, and includes an electric motor with a gear box (e.g., a 4:1 gear box) that drives a rotatable screw shaft which, in turn, is threadingly coupled to a nut that runs on ball bearings. Although, unlike the first actuator assembly 258, the second actuator assembly 260 further includes a swing arm which is operatively coupled to the nut of the ball screw actuator. When the nut undergoes displacement along the screw shaft, the swing arm, which is attached to the rotatable carriage assembly 257 with the force measurement assembly 202, is rotated. As such, when the swing arm is rotated, the rotatable carriage assembly 257 with the force measurement assembly 202 is also rotated about a transverse rotational axis TA (see FIG. 20). That is, the force measurement assembly 202 undergoes generally single degree-of-freedom rotation about the transverse rotational axis TA. In one embodiment, the imaginary transverse rotational axis TA approximately passes through the center of the ankle joints of the subject 208 when he or she is disposed on the force measurement assembly 202. Because the second actuator assembly 260 is also in the form of a highly efficient ball screw actuator, it includes a brake assembly disposed adjacent to the electric motor to prevent it from being back-driven, similar to that of the first actuator assembly 258. The brake assembly of the second actuator assembly 260 prevents the force measurement assembly 202 from being inadvertently rotated so as to protect a subject disposed thereon from its inadvertent movement. When the translatable sled assembly 256 is translated by the first actuator assembly 258, the second actuator assembly 260 is translated with the sled assembly 256 and the force plate. In particular, when the translatable sled assembly 256 is translated backwards and forwards by the first actuator assembly 258, the second actuator assembly 260 is displaced along a rail or rod of the base assembly 206.

In a preferred embodiment of the invention, both the first actuator assembly 258 and the second actuator assembly 260 are provided with two (2) electrical cables operatively coupled thereto. The first cable connected to each actuator assembly 258, 260 is a power cable for the electric motor and brake of each actuator, while the second cable transmits positional information from the respective actuator encoder that is utilized in the feedback control of each actuator assembly 258, 260.

Referring back to FIG. 18, it can be seen that the base assembly 206 is operatively coupled to the data acquisition/data processing device 204 by virtue of an electrical cable 218. The electrical cable 218 is used for transmitting data between the programmable logic controller (PLC) of the base assembly 206 and the data acquisition/data processing device 204 (i.e., the operator computing device 204). Various types of data transmission cables can be used for cable 218. For example, the cable 218 can be a Universal Serial Bus (USB) cable or an Ethernet cable. Preferably, the electrical cable 218 contains a plurality of electrical wires bundled together that are utilized for transmitting data. However, it is to be understood that the base assembly 206 can be operatively coupled to the data acquisition/data processing device 204 using other signal transmission means, such as a wireless data transmission system.

Figure 23:
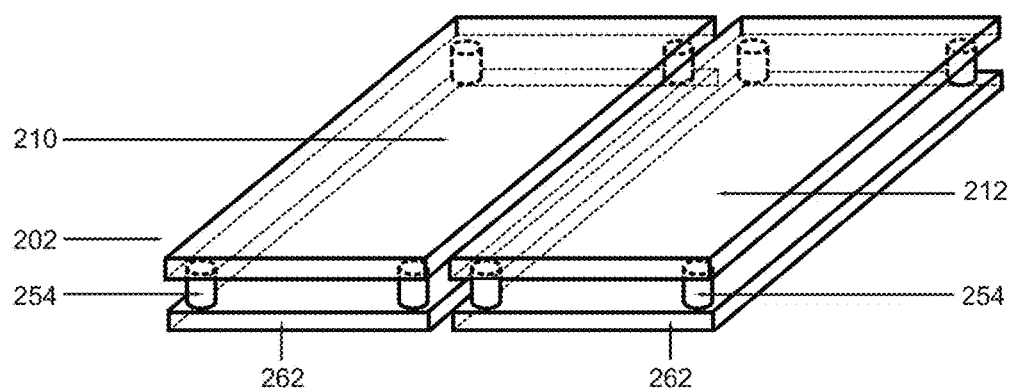
FIG. 23 is a diagrammatic perspective view of an exemplary force measurement assembly used in the balance perturbation system of FIG. 18, wherein the force measurement assembly is in the form of a dual force plate.

In the illustrated embodiment, the at least one force transducer associated with the first and second plate components 210, 212 comprises four (4) pylon-type force transducers 254 (or pylon-type load cells) that are disposed underneath, and near each of the four corners (4) of the first plate component 210 and the second plate component 212 (see FIG. 23). Each of the eight (8) illustrated pylon-type force transducers has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 202. As shown in FIG. 23, a respective base plate 262 can be provided underneath the transducers 254 of each plate component 210, 212 for facilitating the mounting of the force plate assembly to the rotatable carriage assembly 257 of the translatable sled assembly 256 of the base assembly 206. Alternatively, a plurality of structural frame members (e.g., formed from steel) could be used in lieu of the base plates 262 for attaching the dual force plate assembly to the rotatable carriage assembly 257 of the translatable sled assembly 256 of the base assembly 206. Also, in one or more other embodiments, the force measurement assembly 202 may comprise a single force plate in lieu of the dual force plate of FIGS. 23 and 24.

In an alternative embodiment, rather than using four (4) pylon-type force transducers 254 on each plate component 210, 212, force transducers in the form of transducer beams could be provided under each plate component 210, 212. In this alternative embodiment, the first plate component 210 could comprise two transducer beams that are disposed underneath, and on generally opposite sides of the first plate component 210. Similarly, in this embodiment, the second plate component 212 could comprise two transducer beams that are disposed underneath, and on generally opposite sides of the second plate component 212. Similar to the pylon-type force transducers 254, the force transducer beams could have a plurality of strain gages attached to one or more surfaces thereof for sensing the mechanical strain imparted on the beam by the force(s) applied to the surfaces of the force measurement assembly 202.

Rather, than using four (4) force transducer pylons under each plate, or two spaced apart force transducer beams under each plate, it is to be understood that the force measurement assembly 202 can also utilize the force transducer technology described in U.S. Pat. No. 8,544,347, the entire disclosure of which is incorporated herein by reference.

Referring to FIGS. 19 and 20, the base assembly 206 is preferably provided with a plurality of support feet 226 disposed thereunder. Preferably, each of the four (4) corners of the base assembly 206 is provided with a support foot 226. In one embodiment, each support foot 226 is attached to a bottom surface of base assembly 206. In one preferred embodiment, at least one of the support feet 226 is adjustable so as to facilitate the leveling of the base assembly 206 on an uneven floor surface (e.g., see FIG. 20, the support foot can be provided with a threaded shaft 229 that permits the height thereof to be adjusted). For example, referring to FIG. 19, the right corner of the base assembly 206 may be provided with a removable cover plate 227 for gaining access to an adjustable support foot 226 with threaded shaft 229.

In one exemplary embodiment, with reference to FIG. 19, the base assembly 206 has a length $L_B$ of approximately five feet (5'-0"), a width $W_B$ of approximately five feet (5'-0"), and a step height $H_B$ of approximately four (4) inches. In other words, the base assembly has an approximately 5'-0" by 5'-0" footprint with step height of approximately four (4) inches. In other exemplary embodiments, the base assembly 206 has a width $W_B$ of slightly less than five feet (5'-0"), for example, a width $W_B$ lying in the range between approximately fifty-two (52) inches and approximately fifty-nine (59) inches (or between fifty-two (52) inches and fifty-nine (59) inches). Also, in other exemplary embodiments, the base assembly 206 has a step height lying in the range between approximately four (4) inches and approximately four and one-half (4½) inches (or between four (4) inches and four and one-half (4½) inches). Advantageously, the design of the base assembly 206 is such that its step height is minimized. For example, the placement of the second actuator assembly 260 above the top surface of the base assembly 206 facilitates a reduction in the step height of the base assembly 206. It is highly desirable for the base assembly 206 to have as low a profile as possible. A reduced step height especially makes it easier for subjects having balance disorders to step on and off the base assembly 206. This reduced step height is particularly advantageous for elderly subjects or patients being tested on the balance perturbation system 200 because it is typically more difficult for elderly subjects to step up and down from elevated surfaces.

Now, with reference to FIGS. 18-20, the subject visual display device 207 of the balance perturbation system 200 will be described in more detail. In one exemplary embodiment, the subject visual display device 207 may comprise a projector, a generally spherical mirror (i.e., a convexly curved mirror that has the shape of a piece cut out of a spherical surface), and a generally hemispherical concave projection screen 268 with a variable radius (i.e., the radius of the hemispherical projection screen 268 becomes increasingly larger from its center to its periphery). As shown in FIG. 18, the hemispherical projection screen 268 may be provided with a peripheral flange 269 therearound. In one exemplary embodiment, the lens of the projector projects an image onto the generally spherical mirror which, in turn, projects the image onto the generally hemispherical projection screen 268. Advantageously, the generally hemispherical projection screen 268 is a continuous curved surface that does not contain any lines or points resulting from the intersection of adjoining planar or curved surfaces. Thus, the projection screen 268 is capable of creating a completely immersive visual environment for a subject being tested on the force measurement assembly 202 because the subject is unable to focus on any particular reference point or line on the screen 268. As such, the subject becomes completely immersed in the virtual reality scene(s) being projected on the generally hemispherical projection screen 268, and thus, his or her visual perception can be effectively altered during a test being performed using the balance perturbation system 200 (e.g., a balance test). In order to permit a subject to be substantially circumscribed by the generally hemispherical projection screen 268 on three sides, the bottom of the screen 268 is provided with a semi-circular cutout 278 in the illustrative embodiment. While the generally hemispherical projection screen 268 thoroughly immerses the subject 208 in the virtual reality scene(s), it advantageously does not totally enclose the subject 208. Totally enclosing the subject 208 could cause him or her to become extremely claustrophobic. Also, the clinician would be unable to observe the subject or patient in a totally enclosed environment. As such, the illustrated embodiment of the balance perturbation system 200 does not utilize a totally enclosed environment, such as a closed, rotating shell, etc. Also, as shown in FIGS. 18-20, the subject visual display device 207 is not attached to the subject 208, and it is spaced apart from the force measurement assembly 202 disposed in the base assembly 206.

In one embodiment of the invention, the generally hemispherical projection screen 268 is formed from a suitable material (e.g., an acrylic, fiberglass, fabric, aluminum, etc.) having a matte gray color. A matte gray color is preferable to a white color because it minimizes the unwanted reflections that can result from the use of a projection screen having a concave shape. Also, in an exemplary embodiment, the projection screen 268 has a diameter of approximately 69 inches and a depth of approximately 40 inches. In other exemplary embodiments, the projection screen 268 has a width lying in the range between approximately sixty-eight (68) inches and approximately ninety-two (92) inches (or between sixty-eight (68) inches and ninety-two (92) inches). For example, including the flange 269, the projection screen 268 could have a width of approximately seventy-three (73) inches. In some embodiments, the target distance between the subject and the front surface of the projection screen 268 can lie within the range between approximately 25 inches and approximately 40 inches (or between 25 inches and 40 inches). Although, those of ordinary skill in the art will readily appreciate that other suitable dimensions and circumscribing geometries may be utilized for the projection screen 268, provided that the selected dimensions and circumscribing geometries for the screen 268 are capable of creating an immersive environment for a subject disposed on the force measurement assembly 202 (i.e., the screen 268 of the subject visual display device engages enough of the subject's peripheral vision such that the subject becomes, and remains immersed in the virtual reality scenario). In one or more embodiments, the projection screen 268 fully encompasses the peripheral vision of the subject 208 (e.g., by the coronal plane CP of the subject being approximately aligned with the flange 269 of the projection screen 268 or by the coronal plane CP being disposed inwardly from the flange 269 within the hemispherical confines of the screen 268). In other words, the output screen 268 of the at least one visual display 207 at least partially circumscribes three sides of a subject 208 (e.g., see FIG. 18). As shown in FIGS. 18-20, a top cover is preferably provided over the projector, the mirror, and cutout in the output screen 268 so as to protect these components, and to give the visual display device 207 a more finished appearance.

In a preferred embodiment, the data acquisition/data processing device 204 is configured to convert a two-dimensional (2-D) image, which is configured for display on a conventional two-dimensional screen, into a three-dimensional (3-D) image that is capable of being displayed on the hemispherical output screen 268 without excessive distortion. That is, the data acquisition/data processing device 204 executes a software program that utilizes a projection mapping algorithm to "warp" a flat 2-D rendered projection screen image into a distorted 3-D projection image that approximately matches the curvature of the final projection surface (i.e., the curvature of the hemispherical output screen 268), which takes into account both the distortion of the lens of the projector and any optical surfaces that are used to facilitate the projection (e.g., generally spherical mirror). In particular, the projection mapping algorithm utilizes a plurality of virtual cameras and projection surfaces (which are modeled based upon the actual projection surfaces) in order to transform the two-dimensional (2-D) images into the requisite three-dimensional (3-D) images. Thus, the projector lens information, the spherical mirror dimensional data, and the hemispherical projection screen 268 dimensional data are entered as inputs into the projection mapping algorithm software. When a human subject is properly positioned in the confines of the hemispherical output screen 268, he or she will see a representation of the virtual reality scene wrapping around them instead of only seeing a small viewing window in front of him or her. Advantageously, using a software package comprising a projection mapping algorithm enables the system 200 to use previously created 3-D modeled virtual worlds and objects without directly modifying them. Rather, the projection mapping algorithm employed by the software package merely changes the manner in which these 3-D modeled virtual worlds and objects are projected into the subject's viewing area.

Those of ordinary skill in the art will also appreciate that the subject visual display device 207 may utilize other suitable projection means. For example, in an alternative exemplary embodiment, a projector with a fisheye-type lens and no mirror is utilized in the subject visual display system to project an image onto the screen 268.

In one or more embodiments, the base assembly 206 has a width $W_B$ (see e.g., FIG. 19) measured in a direction generally parallel to the coronal plane CP of the subject (see e.g., FIG. 18) and a length $L_B$ (FIG. 19) measured in a direction generally parallel to the sagittal plane SP of the subject (FIG. 18). In these one or more embodiments, a width of the output screen 268 of the at least one visual display device 207 is less than approximately 1.5 times the width $W_B$ of the base assembly 206 (or less than 1.5 times the width $W_B$ of the base assembly 206), and a depth of the output screen 268 of the at least one visual display device 207 is less than the length $L_B$ of the base assembly 206 (FIG. 19). In the illustrated embodiment, the width of the output screen 268 of the at least one visual display device 207 is greater than the width $W_B$ of the base assembly 206. In some embodiments, a width of the output screen 268 of the at least one visual display device 207 is greater than approximately 1.3 times the width $W_B$ of the base assembly 206 (or greater than 1.3 times the width $W_B$ of the base assembly 206).

As illustrated in FIG. 19, the generally hemispherical projection screen 268 can be supported from a floor surface using a screen support structure 267. In other words, the screen support structure 267 is used to elevate the projection screen 268 a predetermined distance above the floor of a room. With reference to FIG. 19, it can be seen that the illustrated screen support structure 267 comprises a lower generally U-shaped member 267a, an upper generally U-shaped member 267b, and a plurality of vertical members 267c, 267d. As best shown in FIG. 19, the two vertical members 267c, 267d are disposed on opposite sides of the screen 268. The screen support structure 267 maintains the projection screen 268 in a stationary position. As such, the position of the projection screen 268 is generally fixed relative to the base assembly 206.

Next, referring again to FIG. 18, the operator visual display device 230 of the balance perturbation system 200 will be described in more particularity. In the illustrated embodiment, the operator visual display device 230 is in the form of a flat panel monitor. Those of ordinary skill in the art will readily appreciate that various types of flat panel monitors having various types of data transmission cables 240 may be used to operatively couple the operator visual display device 230 to the data acquisition/data processing device 204. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 204. Alternatively, in other embodiments of the invention, the visual display device 230 can be operatively coupled to the data acquisition/data processing device 204 using wireless data transmission means. Electrical power is supplied to the visual display device 230 using a separate power cord that connects to a building wall receptacle.

Also, as shown in FIG. 18, the subject visual display device 207 is operatively coupled to the data acquisition/data processing device 204 by means of a data transmission cable 220. More particularly, the projector of the subject visual display device 207 is operatively connected to the data acquisition/data processing device 204 via the data transmission cable 220. Like the data transmission cable 240 described above for the operator visual display device 230, various types of data transmission cables 220 can be used to operatively connect the subject visual display device 207 to the data acquisition/data processing device 204 (e.g., the various types described above).

Those of ordinary skill in the art will appreciate that the visual display device 230 can be embodied in various forms. For example, if the visual display device 230 is in the form of flat screen monitor as illustrated in FIG. 18, it may comprise a liquid crystal display (i.e., an LCD display), a light-emitting diode display (i.e., an LED display), a plasma display, a projection-type display, or a rear projection-type display. The operator visual display device 230 may also be in the form of a touch pad display. For example, the operator visual display device 230 may comprise multi-touch technology which recognizes two or more contact points simultaneously on the surface of the screen so as to enable users of the device to use two fingers for zooming in/out, rotation, and a two finger tap.

Figure 25:
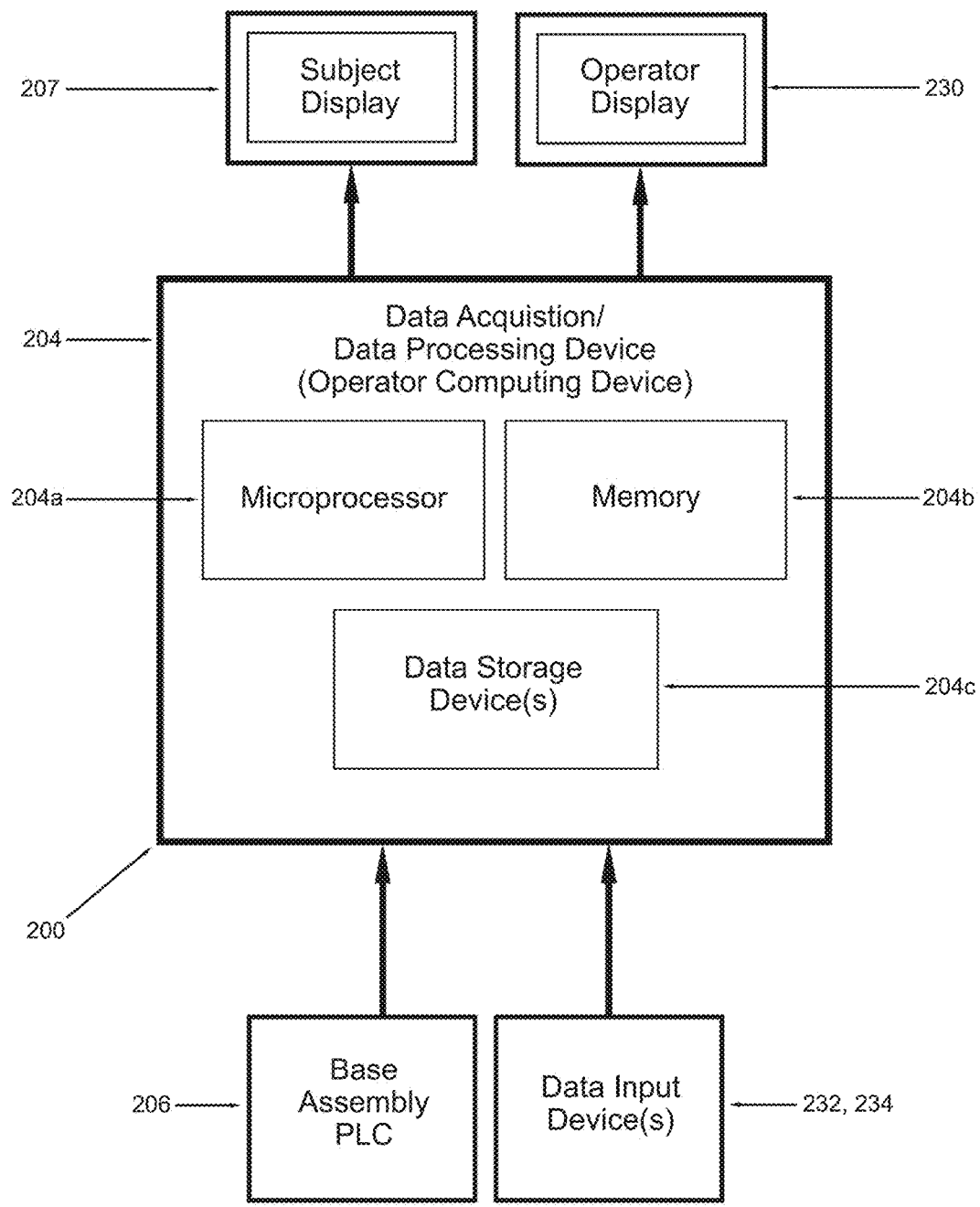
FIG. 25 is a block diagram of constituent components of the balance perturbation system having a displaceable force measurement assembly, according to the second embodiment of the invention.

Now, turning to FIG. 25, it can be seen that the illustrated data acquisition/data processing device 204 (i.e., the operator computing device) of the balance perturbation system 200 includes a microprocessor 204a for processing data, memory 204b (e.g., random access memory or RAM) for storing data during the processing thereof, and data storage device(s) 204c, such as one or more hard drives, compact disk drives, floppy disk drives, flash drives, or any combination thereof. As shown in FIG. 25, the programmable logic controller (PLC) of the base assembly 206, the subject visual display device 207, and the operator visual display device 230 are operatively coupled to the data acquisition/data processing device 204 such that data is capable of being transferred between these devices 204, 206, 207, and 230. Also, as illustrated in FIG. 25, a plurality of data input devices 232, 234 such as the keyboard 232 and mouse 234 shown in FIG. 18, are operatively coupled to the data acquisition/data processing device 204 so that a user is able to enter data into the data acquisition/data processing device 204. In some embodiments, the data acquisition/data processing device 204 can be in the form of a desktop computer, while in other embodiments, the data acquisition/data processing device 204 can be embodied as a laptop computer.

Advantageously, the programmable logic controller 272 of the base assembly 206 (see e.g., FIG. 26, which is a type of data processing device) provides real-time control of the actuator assemblies 258, 260 that displace the force measurement assembly 202 (i.e., force plate assembly 202). The real-time control provided by the programmable logic controller 272 ensures that the motion control software regulating the displacement of the force plate assembly 202 operates at the design clock rate, thereby providing fail-safe operation for subject safety. In one embodiment, the programmable logic controller 272 comprises both the motion control software and the input/output management software, which controls the functionality of the input/output (I/O) module of the programmable logic controller 272. In one embodiment, the programmable logic controller 272 utilizes EtherCAT protocol for enhanced speed capabilities and real-time control.

In one or more embodiments, the input/output (I/O) module of the programmable logic controller 272 allows various accessories to be added to the balance perturbation system 200. For example, an eye movement tracking system, such as that described by U.S. Pat. Nos. 6,113,237 and 6,152,564 could be operatively connected to the input/output (I/O) module of the programmable logic controller 272. As another example, a head movement tracking system, which is instrumented with one or more accelerometers, could be operatively connected to the input/output (I/O) module.

Figure 26:
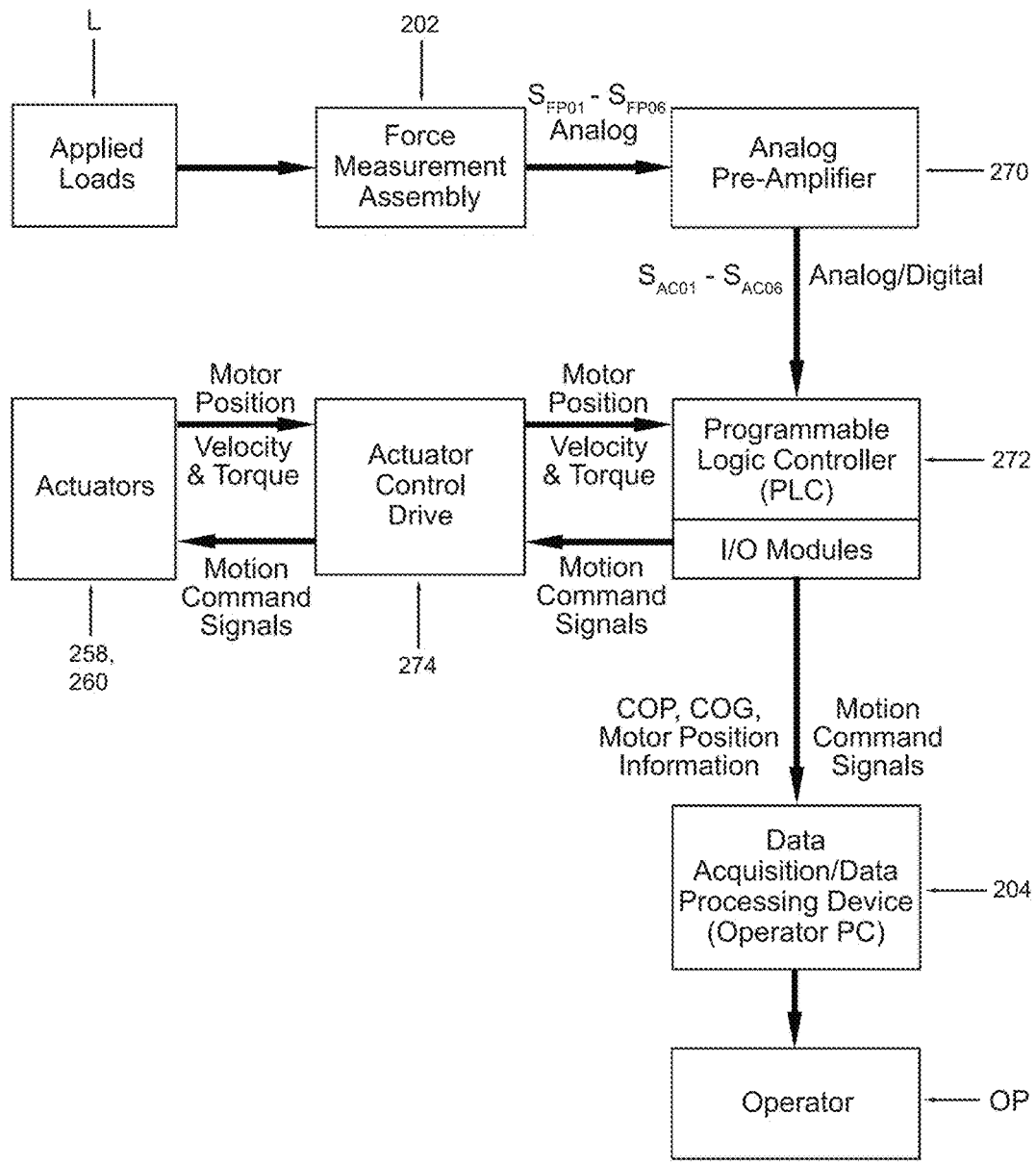
FIG. 26 is a block diagram illustrating data manipulation operations and motion control operations carried out by the balance perturbation system, according to the second embodiment of the invention.

FIG. 26 graphically illustrates the acquisition and processing of the load data and the control of the actuator assemblies 258, 260 carried out by the exemplary balance perturbation system 200. Initially, as shown in FIG. 26, a load L is applied to the force measurement assembly 202 by a subject disposed thereon. The load is transmitted from the first and second plate components 210, 212 to its respective set of pylon-type force transducers or force transducer beams. As described above, in one embodiment of the invention, each plate component 210, 212 comprises four (4) pylon-type force transducers 254 disposed thereunder. Preferably, these pylon-type force transducers 254 are disposed near respective corners of each plate component 210, 212. In a preferred embodiment of the invention, each of the pylon-type force transducers includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the first and second plate components 210, 212. For each plurality of strain gages disposed on the pylon-type force transducers, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 254 disposed under each plate component 210, 212 output a total of three (3) analog output voltages (signals). In some embodiments, the three (3) analog output voltages from each plate component 210, 212 are then transmitted to an analog preamplifier board 270 in the base assembly 206 for pre-conditioning (i.e., signals $S_{FPO1}$-$S_{FPO6}$ in FIG. 26). The preamplifier board is used to increase the magnitudes of the transducer analog output voltages. After which, the analog force plate output signals $S_{APO1}$-$S_{APO6}$ are transmitted from the analog preamplifier 270 to the programmable logic controller (PLC) 272 of the base assembly 206. In the programmable logic controller (PLC) 272, analog force plate output signals $S_{APO1}$-$S_{APO6}$ are converted into forces, moments, centers of pressure (COP), and/or a center of gravity (COG) for the subject. Then, the forces, moments, centers of pressure (COP), subject center of gravity (COG), and/or sway angle for the subject computed by the programmable logic controller 272 are transmitted to the data acquisition/data processing device 204 (operator computing device 204) so that they can be utilized in reports displayed to an operator OP. Also, in yet another embodiment, the preamplifier board 270 additionally could be used to convert the analog voltage signals into digital voltage signals (i.e., the preamplifier board 270 could be provided with an analog-to-digital converter). In this embodiment, digital voltage signals would be transmitted to the programmable logic controller (PLC) 272 rather than analog voltage signals.

Figure 24:
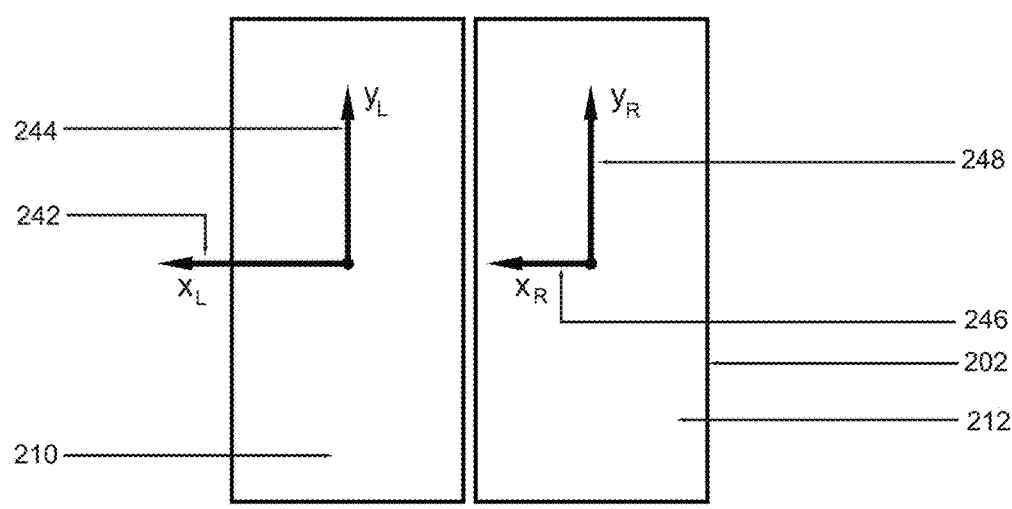
FIG. 24 is a diagrammatic top view of the force measurement assembly of FIG. 23 used in the balance perturbation system with exemplary coordinate axes superimposed thereon.

When the programmable logic controller 272 receives the voltage signals $S_{ACO1}$-$S_{ACO6}$, it initially transforms the signals into output forces and/or moments by multiplying the voltage signals $S_{ACO1}$-$S_{ACO6}$ by a calibration matrix (e.g., $F_{Lz}$, $M_{Lx}$, $M_{Ly}$, $F_{Rz}$, $M_{Rx}$, $M_{Ry}$). After which, the center of pressure for each foot of the subject (i.e., the x and y coordinates of the point of application of the force applied to the measurement surface by each foot) are determined by the programmable logic controller 272. Referring to FIG. 24, which depicts a top view of the measurement assembly 202, it can be seen that the center of pressure coordinates ($x_{P_L}$, $y_{P_L}$) for the first plate component 210 are determined in accordance with x and y coordinate axes 242, 244. Similarly, the center of pressure coordinates ($x_{P_R}$, $y_{P_R}$) for the second plate component 212 are determined in accordance with x and y coordinate axes 246, 248. If the force transducer technology described in U.S. Pat. No. 8,544,347 is employed, it is to be understood that the center of pressure coordinates ($x_{P_L}$, $y_{P_L}$, $x_{P_R}$, $x_{P_R}$) can be computed in the particular manner described in that patent.

As explained above, rather than using a measurement assembly 202 having first and second plate components 210, 212, a force measurement assembly in the form of a single force plate may be employed. As discussed hereinbefore, the single force plate comprises a single measurement surface on which both of a subject's feet are placed during testing. As such, rather than computing two sets of center of pressure coordinates (i.e., one for each foot of the subject), the embodiments employing the single force plate compute a single set of overall center of pressure coordinates ($x_P$, $y_P$) in accordance with a single set of x and y coordinate axes.

In one exemplary embodiment, the programmable logic controller 272 in the base assembly 206 determines the vertical forces $F_{Lz}$, $F_{Rz}$ exerted on the surface of the first and second force plates by the feet of the subject and the center of pressure for each foot of the subject, while in another exemplary embodiment, the output forces of the data acquisition/data processing device 204 include all three (3) orthogonal components of the resultant forces acting on the two plate components 210, 212 (i.e., $F_{Lx}$, $F_{Ly}$, $F_{Lz}$, $F_{Rx}$, $F_{Ry}$, $F_{Rz}$) and all three (3) orthogonal components of the moments acting on the two plate components 210, 212 (i.e., $M_{Lx}$, $M_{Ly}$, $M_{Lz}$, $M_{Rx}$, $M_{Ry}$, $M_{Rz}$). In yet other embodiments of the invention, the output forces and moments of the data acquisition/data processing device 204 can be in the form of other forces and moments as well.

In the illustrated embodiment, the programmable logic controller 272 converts the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the programmable logic controller 272 also computes a sway angle for the subject using a corrected center of gravity (COG') value, wherein the center of gravity (COG) value is corrected to accommodate for the offset position of the subject relative to the origin of the coordinate axes (242, 244, 246, 248) of the force plate assembly 202. For example, the programmable logic controller 272 computes the sway angle for the subject in the following manner:

$$\theta = \sin^{-1}\left(\frac{COG'}{0.55h}\right) - 2.3° \quad (11)$$

where:
θ: sway angle of the subject;
COG': corrected center of gravity of the subject; and
h: height of the center of gravity of the subject.

Now, referring again to the block diagram of FIG. 26, the manner in which the motion of the force measurement assembly 202 is controlled will be explained. Initially, an operator OP inputs one or more motion commands at the operator computing device 204 (data acquisition/data processing device 204) by utilizing one of the user input devices 232, 234. Once, the one or more motion commands are processed by the operator computing device 204, the motion command signals are transmitted to the programmable logic controller 272. Then, after further processing by the programmable logic controller 272, the motion command signals are transmitted to the actuator control drive 274. Finally, the actuator control drive 274 transmits the direct-current (DC) motion command signals to the first and second actuator assemblies 258, 260 so that the force measurement assembly 202, and the subject disposed thereon, can be displaced in the desired manner. The actuator control drive 274 controls the position, velocity, and torque of each actuator motor.

In order to accurately control the motion of the force measurement assembly 202, a closed-loop feedback control routine may be utilized by the balance perturbation system 200. As shown in FIG. 26, the actuator control drive 274 receives the position, velocity, and torque of each actuator motor from the encoders provided as part of each actuator assembly 258, 260. Then, from the actuator control drive 274, the position, velocity, and torque of each actuator motor is transmitted to the programmable logic controller 272, wherein the feedback control of the first and second actuator assemblies 258, 260 is carried out. In addition, as illustrated in FIG. 26, the position, velocity, and torque of each actuator motor is transmitted from the programmable logic controller 272 to the operator computing device 204 so that it is capable of being used to characterize the movement of the subject on the force measurement assembly 202 (e.g., the motor positional data and/or torque can be used to compute the sway of the subject). Also, the rotational and translational positional data that is received from first and second actuator assemblies 258, 260 can be transmitted to the operator computing device 204.

Referring again to FIG. 20, it can be seen that the base assembly 206 of the force measurement assembly 202 further includes an isolation transformer 276. In the illustrative embodiment, the building power supply is electrically coupled to the isolation transformer 276. In one exemplary embodiment, the isolation transformer 276 is a medical-grade isolation transformer that isolates the electrical system of the base assembly 206 from the building electrical system. The isolation transformer 276 greatly minimizes any leakage currents from the building electrical system, which could pose a potential safety hazard to a subject standing on the metallic base assembly 206. In the illustrative embodiment, the primary winding of the isolation transformer 276 is electrically coupled to the building electrical system, whereas the secondary winding of isolation transformer 276 is electrically coupled to the programmable logic controller 272.

In the illustrative embodiment, the programmable logic controller 272 may be electrically coupled to the actuator control drive 274 via the emergency stop (E-stop) switch 238 depicted in FIG. 19. As explained above, in one embodiment, the emergency stop switch 238 is in the form of a red pushbutton that can be easily pressed by a user of the force measurement system 200 (e.g., a subject on the force measurement assembly 202 or an operator) in order to quasi-instantaneously stop the displacement of the force measurement assembly 202. Because the emergency stop switch 238 is designed to fail open, the emergency stop switch 238 is a fail-safe means of aborting the operations (e.g., the software operations) performed by the programmable logic controller 272. Thus, even if the programmable logic controller 272 fails, the emergency stop switch 238 will not fail, thereby cutting the power to the actuator control drive 274 so that the force measurement assembly 202 remains stationary (i.e., the brakes on the actuator assemblies 258, 260 will engage, and thus, prevent any unintentional movement thereof). Also, in one embodiment, the emergency stop switch assembly 238 includes a reset button for re-enabling the operation of the actuator control drive 274 after it is has been shut down by the emergency stop switch.

In the illustrative embodiment, the first and second actuator assemblies 258, 260 are powered by the actuator control drive 274. Also, in the illustrative embodiment, the electrical system of the base assembly 206 may further include a power entry module that includes a circuit breaker (e.g., a 20A circuit breaker) and a filter. In addition, the electrical system of the base assembly 206 may further include an electromagnetic interference (EMI) filter that reduces electrical noise so as to meet the requirements of the Federal Communications Commission (FCC).

Now, the manner in which the programmable logic controller 272 and data acquisition/data processing device 204 of the balance perturbation system 200 are specially programmed to perturb the balance of the subject 208 disposed on the force measurement assembly 202 of the second illustrative embodiment will be described. As explained above, the data acquisition/data processing device 204 is operatively coupled to the programmable logic controller 272 of the force measurement assembly 202. In one illustrative embodiment, the programmable logic controller 272 (i.e., a data processing device) is specially programmed to generate a first perturbation signal for introducing a first type of perturbation to the force measurement assembly 202 and a second perturbation signal for introducing a second type of perturbation to the force measurement assembly 202. Also, in the illustrative embodiment, programmable logic controller 272 is specially programmed to control the angular displacement position of the force measurement assembly 202 using the first perturbation signal and the translational displacement position of the force measurement assembly 202 using the second perturbation signal such that the displaceable force measurement assembly 202 perturbs a balance of the person. In other words, the force measurement assembly 202 has two degrees of freedom for the perturbations (i.e., rotation and translation). As described in detail hereinafter, in order to create perturbations, the frequency and the amplitude of the angular and translational displacement positions can be varied. In an alternative illustrative embodiment, the data acquisition/data processing device 204, rather than the programmable logic controller 272, may be specially programmed to generate the first and second perturbation signals, to control the angular displacement position of the force measurement assembly 202 using the first perturbation signal, and to control the translational displacement position of the force measurement assembly 202 using the second perturbation signal.

Figure 27:
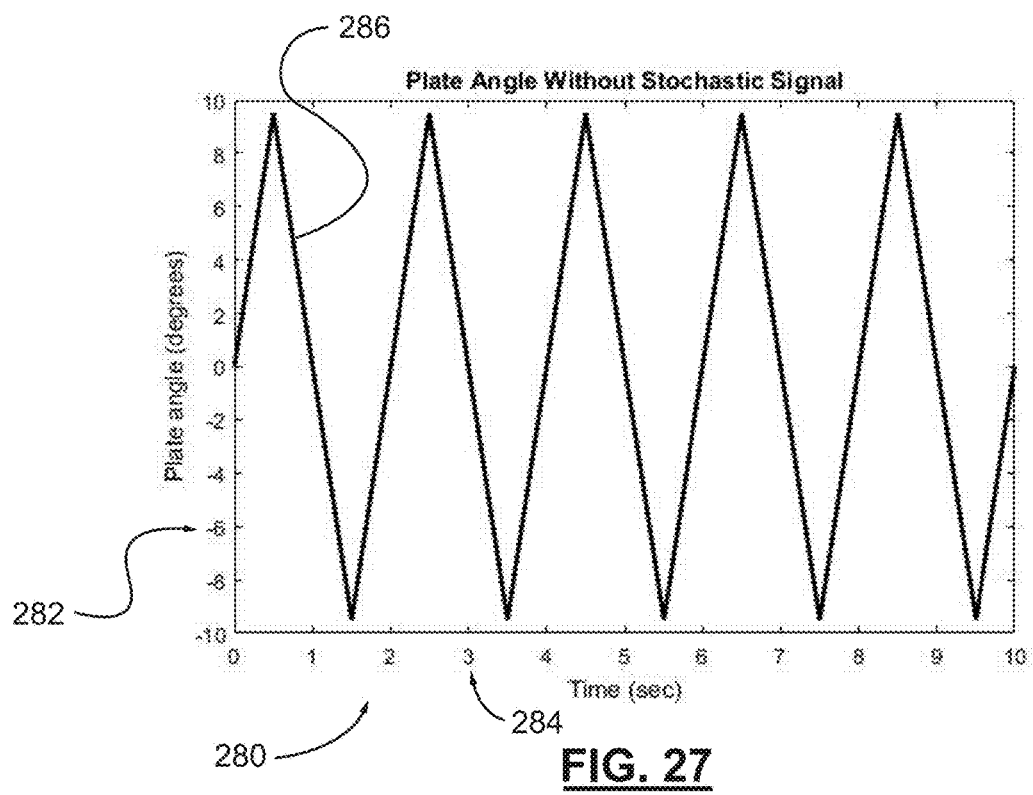
FIG. 27 is a graph illustrating a rotational displacement signal with no perturbations for controlling the angle of the displaceable force measurement assembly of the balance perturbation system in FIG. 18.

An exemplary angular position signal generated by the programmable logic controller 272 or the data acquisition/data processing device 204 for controlling the angular displacement position of the force measurement assembly 202 is illustrated in the graph 280 of FIG. 27. As shown in this figure, the y-axis 282 of the graph 280 is the force measurement assembly angle (i.e., force plate angle) in degrees, while the x-axis 284 of the graph 280 is the time in seconds (sec). In the graph 280 of FIG. 27, it can be seen that the displacement curve 286 oscillates between a minimum angular value of approximately −9.5 degrees and a maximum angular value of approximately 9.5 degrees over a time duration of approximately 10.0 seconds. In FIG. 27, no perturbations have been applied to the force measurement assembly 202 (i.e., FIG. 27 illustrates the displacement of the force plate without the stochastic perturbation having been applied). In the illustrative embodiment, the force measurement assembly 202 is capable of being rotated between −9.5 degrees and +9.5 degrees (i.e., between a clockwise rotational angle of 9.5 degrees and a counterclockwise rotational angle of 9.5 degrees).

Figure 28:
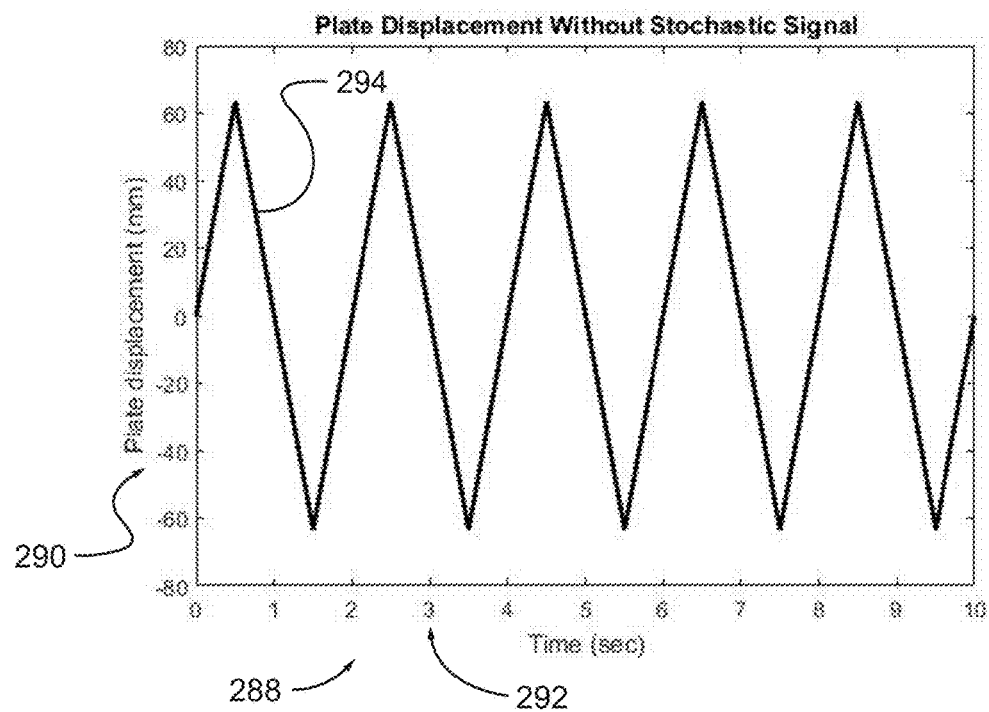
FIG. 28 is a graph illustrating a translational displacement signal with no perturbations for controlling the front-to-back displacement of the displaceable force measurement assembly of the balance perturbation system in FIG. 18.

An exemplary translational position signal generated by the programmable logic controller 272 or the data acquisition/data processing device 204 for controlling the translational displacement position of the force measurement assembly 202 is illustrated in the graph 288 of FIG. 28. As shown in this figure, the y-axis 290 of the graph 288 is the force measurement assembly translational displacement (i.e., force plate forward/rearward displacement) in millimeters (mm), while the x-axis 292 of the graph 288 is the time in seconds (sec). In the graph 288 of FIG. 28, it can be seen that the displacement curve 294 oscillates between a minimum translational displacement value of approximately −63.5 millimeters and a maximum angular value of approximately 63.5 millimeters over a time duration of approximately 10.0 seconds. In FIG. 28, no perturbations have been applied to the force measurement assembly 202 (i.e., FIG. 28 illustrates the displacement of the force plate without the stochastic perturbation having been applied). In the illustrative embodiment, the force measurement assembly 202 is capable of being translationally displaced in both forward and rearward directions by 63.5 millimeters.

In the illustrative embodiment, the first perturbation signal for introducing a first type of perturbation (i.e., angular displacement perturbation) to the force measurement assembly 202 comprises a first stochastic signal, and the second perturbation signal for introducing a second type of perturbation (i.e., translation displacement perturbation) to the force measurement assembly 202 comprises a second stochastic signal. The programmable logic controller 272 or the data acquisition/data processing device 204 is specially programmed to control the angular displacement position of the force measurement assembly 202 using the first perturbation signal and the translational displacement position of the force measurement assembly 202 using the second perturbation signal so as to make the force measurement assembly 202 oscillate in an angular manner, a translational manner, or both an angular and translational manner while the subject 208 is disposed thereon. As will be described hereinafter, the stochastic signal may be of uniform or normal distribution. The stochastic signal is capable of perturbing the subject's somatosensory system while the subject 208 is disposed on the force measurement assembly 202.

In the illustrative embodiment, the generation of the first and second perturbation signals by the programmable logic controller 272 or the data acquisition/data processing device 204 comprises a plurality of different steps. Initially, by utilizing the input devices 232, 234 of the data acquisition/data processing device 204 (e.g., the keyboard 232 and/or mouse 234), a user enters one or more perturbation levels that correspond to at least one of: (i) the stochastic signal base amplitude, and (ii) a frequency of the stochastic signal (i.e., the cut-off frequency of the stochastic signal), and the user additionally may select the type of signal for the stochastic displacement (i.e., uniform or normal). For example, in one exemplary embodiment, a user may have the following six selection options: (i) choosing any one of levels 1 to 10 for the amplitude of the translational perturbation, (ii) choosing any one of levels 1 to 10 for the frequency of the translational perturbation, (iii) selecting the type of signal for the translation perturbation, (iv) choosing any one of levels 1 to 10 for the amplitude of the rotational perturbation, (v) choosing any one of levels 1 to 10 for the frequency of the rotational perturbation, and (vi) selecting the type of signal for the rotational perturbation, In this exemplary embodiment, the first value of the amplitude for both the translational and rotational perturbation is zero (i.e., level 1 corresponds to a zero amplitude, then each of the successive levels may incrementally increase the angle by approximately 1 degree for rotation and approximately 7 millimeters for translation). As such, when level 1 is selected for either of the two amplitudes, the force measurement assembly 202 (i.e., force plate) will not be displaced in that direction. That way, the user is able to customize the displacement of the force measurement assembly 202 such that the force measurement assembly 202 only undergoes rotation, only undergoes translation, or undergoes both rotation and translation. In this exemplary embodiment, the first value of the frequency for both the translational and rotational perturbation may be 1 Hertz, and then each of the successive levels may incrementally increase the frequency by 1 Hertz, up to a maximum frequency of 10 Hertz. In other embodiments, smaller frequency increments may be used for the successive levels, such as 0.1 or 0.2 Hertz.

In the illustrative embodiment, the user may select level 1 through 10 for the amplitude of rotation. The rotational amplitude may range from 0 degrees to 9.5 degrees. The first selected level determines the maximum amplitude of the stochastic signal for the angle of rotation. The user may also select level 1 through 10 for the frequency of rotation. The second selected level determines the maximum frequency of the stochastic signal for angle of rotation. Additionally, in the illustrative embodiment, the user may select the type of signal for stochastic angular displacement (i.e. a uniform or normal stochastic signal). Further, the user may select level 1 through 10 for the amplitude of translation. The translational amplitude may range from 0 millimeters to 63.5 millimeters. The third selected level determines the maximum amplitude of the stochastic signal for the translational displacement. The user may also select level 1 through 10 for the frequency of the translation. The fourth selected level determines the maximum frequency of the stochastic signal for translational displacement. Similar to the angle of rotation, the user also may select the type of signal for stochastic translational displacement (i.e. a uniform or normal stochastic signal). The above selections enable the user to execute the rotational and translational perturbation either independently or simultaneously.

After the user utilizes the input devices 232, 234 of the data acquisition/data processing device 204 to input the perturbation levels and the signal types, the programmable logic controller 272 or the data acquisition/data processing device 204 generates the uniform or normal stochastic signals based upon the amplitude and frequency values entered by the user. The amplitude values entered by the user determines the upper and lower bounds of the stochastic signals generated by the programmable logic controller 272 or the data acquisition/data processing device 204, while the cut-off frequency values entered by the user determines the upper frequency limits of the stochastic signals generated by the programmable logic controller 272 or the data acquisition/data processing device 204. Finally, the programmable logic controller 272 controls the angular displacement and/or translational displacement of the force measurement assembly 202. Each of these steps will be described in further detail hereinafter. When the programmable logic controller 272 generates the stochastic signals, the amplitudes, the cut-off frequencies, and the signal types of the stochastic signals are transmitted from the data acquisition/data processing device 204 to the programmable logic controller 272 so that the stochastic signals are able to be generated by the programmable logic controller 272.

Also, in another mode of operation of the illustrative embodiment, the user has the option of entering a sequencing routine for the displaceable force measurement assembly 202, wherein the rotational and translational displacements are sequenced. In the illustrative embodiment, the sequencing routine allows the user to enter up to 10 signal inputs. For example, one possible sequencing routine could include the following ten displacement tasks executed in a continuous manner while the subject is disposed on the displaceable force measurement assembly 202: (1) translation displacement, amplitude 3 mm, frequency 5 Hz, and signal type: uniform; (2) translational displacement, amplitude 63.5 mm, frequency 1 Hz, and signal type: normal; (3) rotational displacement, amplitude 8 degrees, frequency 0.4 Hz, and signal type: normal; (4) translational displacement, amplitude 13.5 mm, frequency 3 Hz, and signal type: uniform, (5) rotational displacement, amplitude 5 degrees, frequency 0.5 Hz, and signal type: uniform; (6) rotational displacement, amplitude 1 degree, frequency 1 Hz, and signal type: normal; (7) translation displacement, amplitude 20 mm, frequency 4 Hz, and signal type: uniform; (8) translation displacement, amplitude 5 mm, frequency 5 Hz, and signal type: normal; (9) rotational displacement, amplitude 3 degrees, frequency 2 Hz, signal type: uniform; and (10) translation displacement, amplitude 50 mm, frequency 3 Hz, and signal type: uniform. In this mode of operation, the user would also be prompted to enter a time duration for each of the ten displacement tasks (e.g., 10 seconds for the first task, 6 seconds for the second task, etc.). This exemplary sequencing routine would create a predetermined motion profile of random perturbations for the subject. This type of sequencing routine may be used to increase the difficulty level of the balance testing for the subject.

In yet another mode of operation of the illustrative embodiment, the user may be permitted to enter a stochastic amplitude value in the range between zero and approximately 9.5 degrees, inclusive (or between zero and 9.5 degrees, inclusive) for the rotational displacement of the force measurement assembly 202, and between zero and approximately 63.5 millimeters, inclusive (or between zero and 63.5 millimeters, inclusive) for the translational displacement of the force measurement assembly 202. Similarly, in this mode of operation of the illustrative embodiment, the user may be permitted to enter a cut-off frequency value in the range between zero and approximately 10 Hertz, inclusive (or between zero and 10 Hertz, inclusive) for each of the rotational and translational displacements of the force measurement assembly 202.

In addition to entering the amplitude, cut-off frequency, and signal type of the stochastic signals for rotational and translational displacement, the user is also able to selectively regulate the beginning and end of the stochastic signals by pressing a graphical start button on the operator display 230 to initiate the stochastic signals, and then by subsequently pressing a graphical stop button on the operator display 230 to end the stochastic signals (i.e., when the display is a touchscreen).

Figure 29:
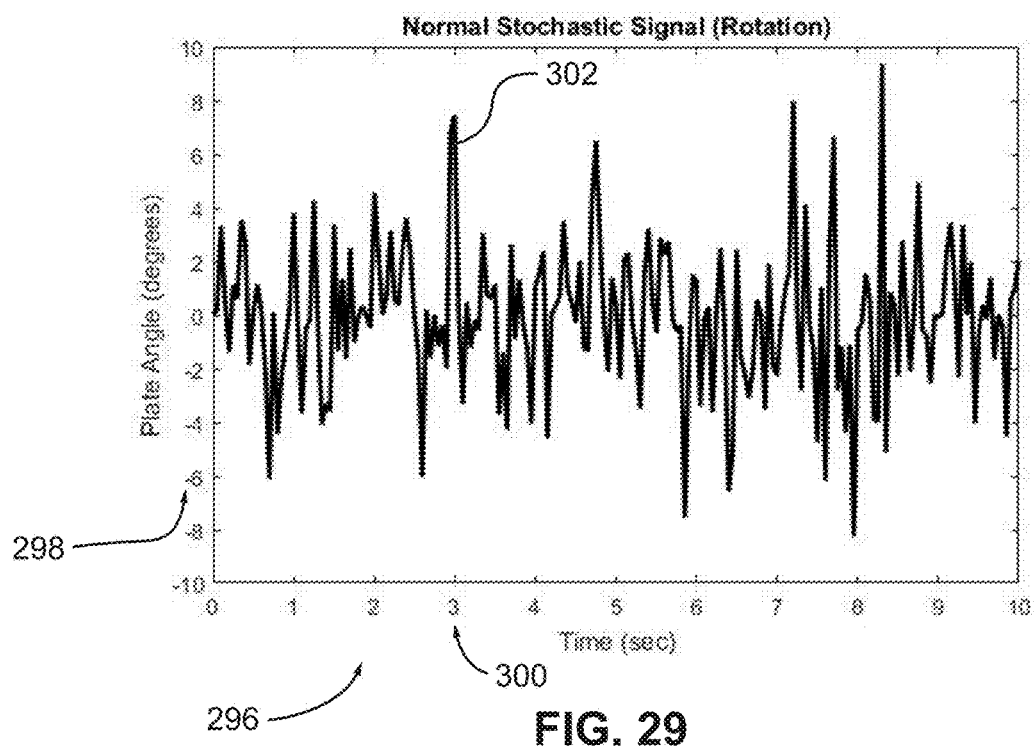
FIG. 29 is a graph illustrating a normal stochastic perturbation signal for controlling the angle of the displaceable force measurement assembly of the balance perturbation system in FIG. 18.
Figure 30:
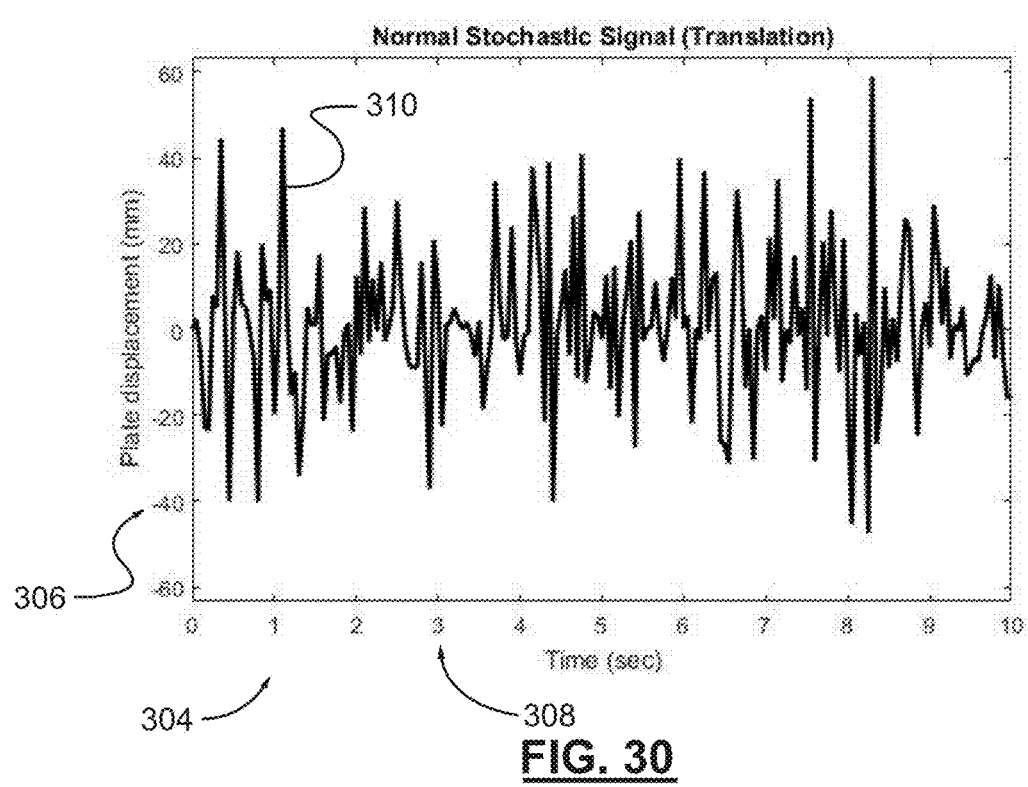
FIG. 30 is a graph illustrating a normal stochastic perturbation signal for controlling the front-to-back displacement of the displaceable force measurement assembly of the balance perturbation system in FIG. 18.

In the illustrative embodiment, the rotational and translational displacements of displaceable force measurement assembly 202 of the balance perturbation system 200 are each capable of being controlled simultaneously and independently. An exemplary normal stochastic signal for rotational displacement that is generated by the programmable logic controller 272 or the data acquisition/data processing device 204 is illustrated in the graph 296 of FIG. 29. As shown in this figure, the y-axis 298 of the graph 296 is the force measurement assembly angle (i.e., force plate angle) in degrees, while the x-axis 300 of the graph 296 is the time in seconds (sec). In the graph 296 of FIG. 29, it can be seen that the normal stochastic signal curve 302 oscillates between a minimum lower limit of approximately −8 degrees and a maximum upper limit of approximately 9.5 degrees over a time duration of approximately 10 seconds. As another example, an exemplary normal stochastic signal for translational displacement that is generated by the programmable logic controller 272 or the data acquisition/data processing device 204 is illustrated in the graph 304 of FIG. 30. As shown in this figure, the y-axis 306 of the graph 304 is the force measurement assembly translational displacement (i.e., force plate forward/rearward displacement) in millimeters, while the x-axis 308 of the graph 304 is the time in seconds (sec). In the graph 304 of FIG. 30, it can be seen that the normal stochastic signal curve 310 oscillates between a minimum lower limit of approximately −47 millimeters and a maximum upper limit of approximately 58 millimeters over a time duration of approximately 10 seconds.

Figure 31:
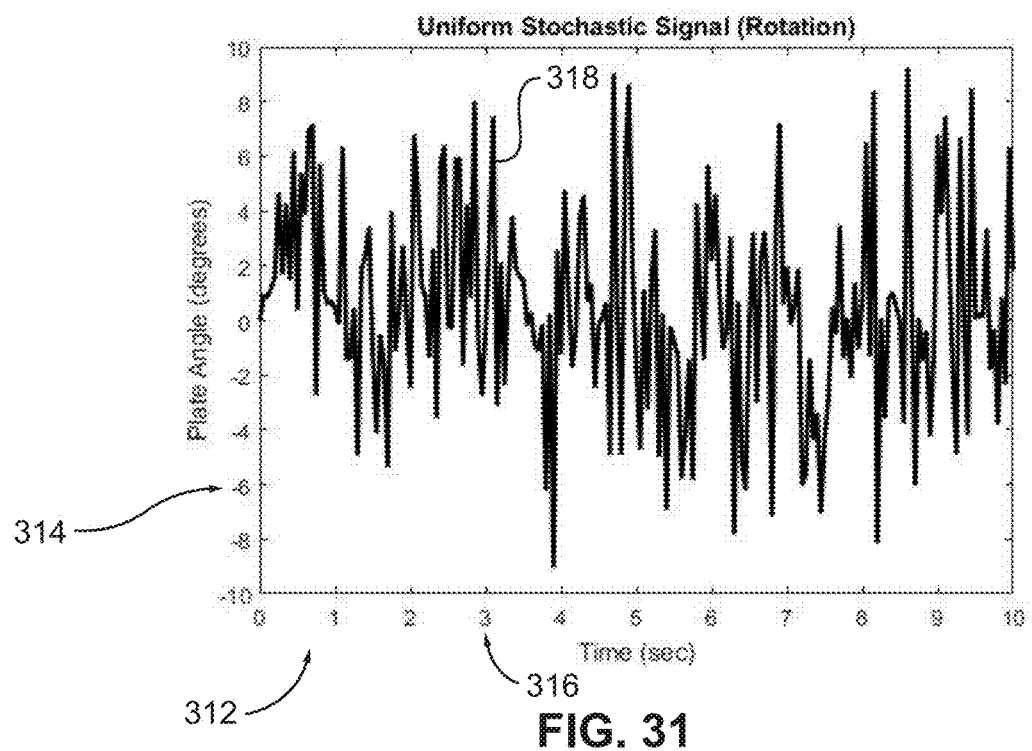
FIG. 31 is a graph illustrating a uniform stochastic perturbation signal for controlling the angle of the displaceable force measurement assembly of the balance perturbation system in FIG. 18.
Figure 32:
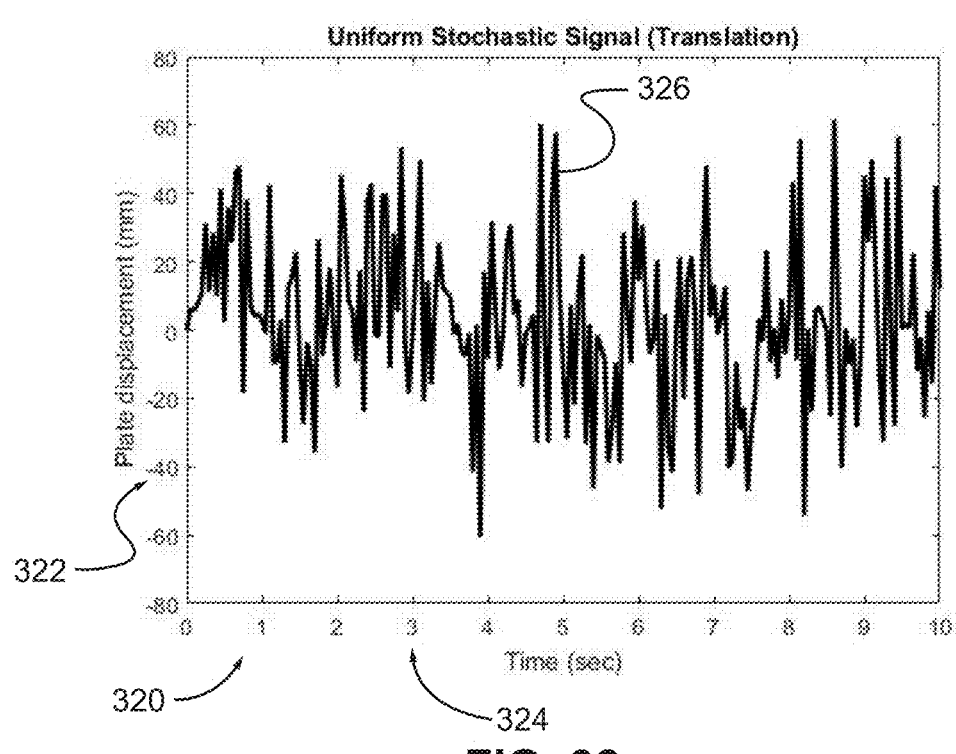
FIG. 32 is a graph illustrating a uniform stochastic perturbation signal for controlling the front-to-back displacement of the displaceable force measurement assembly of the balance perturbation system in FIG. 18.

As yet another example of a perturbation input signal, an exemplary uniform stochastic signal for rotational displacement that is generated by the programmable logic controller 272 or the data acquisition/data processing device 204 is illustrated in the graph 312 of FIG. 31. As shown in this figure, the y-axis 314 of the graph 312 is the force measurement assembly angle (i.e., force plate angle) in degrees, while the x-axis 316 of the graph 312 is the time in seconds (sec). In the graph 312 of FIG. 31, it can be seen that the uniform stochastic signal curve 318 oscillates between a minimum lower limit of approximately −9 degrees and a maximum upper limit of approximately 9.2 degrees over a time duration of approximately 10 seconds. As still another example, an exemplary uniform stochastic signal for translational displacement that is generated by the programmable logic controller 272 or the data acquisition/data processing device 204 is illustrated in the graph of FIG. 32. As shown in this figure, the y-axis 322 of the graph 320 is the force measurement assembly translational displacement (i.e., force plate forward/rearward displacement) in millimeters, while the x-axis 324 of the graph 320 is the time in seconds (sec). In the graph 320 of FIG. 32, it can be seen that the uniform stochastic signal curve 326 oscillates between a minimum lower limit of approximately −60 millimeters and a maximum upper limit of approximately 62 millimeters over a time duration of approximately 10 seconds.

In the second step of the process, where a random uniform or normal random signal is generated by the programmable logic controller 272 or the data acquisition/data processing device 204 at the selected cut-off frequency, a random number function or subroutine may be used to generate the uniform signal random numbers (e.g., the DRAND function block in a TwinCAT software package). In the illustrative embodiment, the random number function utilized by the programmable logic controller 272 or the data acquisition/data processing device 204 requires an initial value input for the specification of the random number series. The output returns a pseudo-random number in the range −1.0 to 1.0 with double accuracy. That is, the random number function generates the same sequence of random numbers each time that the same seed is utilized. As such, in an exemplary embodiment, the seed value that is used for the random number function is acquired for each trial from the low DW of the system time, which gives a sufficiently random seed for each trial. That way, the programmable logic controller 272 or the data acquisition/data processing device 204 does not generate the same random number sequence or produce any other perturbation trends from trial to trial. In one or more embodiments, the operating system time stamp is a 64-bit integer value, with a precision of 100 nanoseconds (ns), which is updated with every call of the programmable logic controller (PLC) 272. In one or more embodiments, the low DW (timeLoDW) is the low-value 4 bytes of the time stamp and it changes very rapidly at rate of 0.01 milliseconds (ms). The random signal has a varying frequency. The randomness of the stochastic signal is highly advantageous because the subjects being tested on the displaceable force measurement assembly 202 are not able to as easily learn how to overcome a particular perturbation sequence during a testing or training routine. If the perturbation employed was always the same, then eventually subjects would learn how to adapt to the perturbation, and the training would become less effective.

When the user selects a uniform-type stochastic signal, a respective uniform stochastic signal, such as that depicted in FIGS. 31 and 32, is used for controlling a respective one of the rotational and translational displacements of the force measurement assembly 202. However, if the user alternatively selects a normal-type stochastic signal, as described above, two (2) uniform signals U1 and U2 generated using the random number function are converted into normal signal N using the following Box-Muller transform equation:

$$N=\sqrt{-2\ln U1}\,\cos(2\pi U2) \qquad (12)$$

In the second illustrative embodiment, as described above for the first illustrative embodiment, the uniform or normal signal is then passed through a fourth order low pass Butterworth filter to limit the frequency component of the signal at a user specified value (i.e., at the frequency entered by the user).

In the illustrative embodiment, prior to the third step of the process, where the programmable logic controller 272 or the data acquisition/data processing device 204 regulates the angular displacement and/or translational displacement of the force measurement assembly 202, the filtered signal is multiplied by the user-specified amplitude value so as to generate the stochastic signals for controlling the angular and/or translational displacements. When the uniform-type stochastic signal is selected by the user, the uniform stochastic signal for controlling the angular and/or translational displacements are determined by the programmable logic controller 272 or the data acquisition/data processing device 204 in accordance with the following equation:

$$\text{Uniform stochastic signal}=\text{filtered uniform signal}*\text{Amplitude} \qquad (13)$$

Thus, in accordance with equation (13) above, the uniform stochastic signal is a function of the filtered, randomly-generated uniform signal and the user-specified amplitude value. More specifically, the programmable logic controller 272 or the data acquisition/data processing device 204 determines the uniform stochastic signal by computing the multiplicative product between the filtered uniform signal and the user-specified amplitude value. Alternatively, when the normal-type stochastic signal is selected by the user, the normal stochastic signal for controlling the angular and/or translational displacements is determined by the programmable logic controller 272 or the data acquisition/data processing device 204 in accordance with the following equation:

$$\text{Normal stochastic signal}=\text{filtered normal signal}*\text{Amplitude}/3 \qquad (14)$$

Thus, in accordance with equation (14) above, the normal stochastic signal is a function of the filtered, normalized randomly-generated uniform signal and the user-specified amplitude value. More specifically, the programmable logic controller 272 or the data acquisition/data processing device 204 determines the normal stochastic signal by computing the multiplicative product between the filtered normal signal and one-third of the user-specified amplitude value.

In one or more embodiments, the aforedescribed rotational and translational displacement calculations are specially programmed on an embedded computer (e.g., the programmable logic controller 272 or the data acquisition/ data processing device 204) that provides a deterministic program cycle time of 1 milliseconds (ms). In other words, the displacement update rate of 1 kilohertz (kHz) is guaranteed by either the hardware architecture of the embedded computer or a real-time operating system (e.g., firmware) that runs on it. In these one or more embodiments, the updated displacements are sent to a servo controller (i.e., actuator control drive 274), which controls the displacements with a closed-loop rate of 4 kilohertz (kHz). In these one or more embodiments, the firmware of the balance perturbation system 200 controls the force measurement assembly perturbations.

In the illustrative embodiment, the programmable logic controller 272 or the data acquisition/data processing device 204 may be specially programmed so as to enable the displaceable force measurement assembly 202 to be controlled in three different modes: (i) rotational displacement only, (ii) translational displacement only, and (iii) simultaneous rotational and translational displacement. In the simultaneous rotational and translational displacement mode, the programmable logic controller 272 or the data acquisition/data processing device 204 utilizes a first stochastic signal to control the rotational displacement of the force measurement assembly 202, and a second stochastic signal to control the translational displacement of the force measurement assembly 202. In the independent rotational displacement or translational displacement modes, the programmable logic controller 272 or the data acquisition/data processing device 204 utilizes a single stochastic signal to either control the rotational or translational displacement of the force measurement assembly 202. Similar to that described above in the first embodiment, the amplitudes of the stochastic signals used to control the rotational displacement and translational displacement of the force measurement assembly 202 are randomly changing over time (i.e., the amplitudes consistently change over time in a random manner). Similarly, the frequencies of the stochastic signals used to control the rotational displacement and translational displacement of the force measurement assembly 202 randomly change over time (i.e., the frequencies consistently changes over time in a random manner). Thus, advantageously, the programmable logic controller 272 or the data acquisition/data processing device 204 generates stochastic signals with both randomly varying amplitudes and frequencies that results in a random perturbation being delivered to the subject 208 on the force measurement assembly 202. The manner of delivery of the perturbation to the subject 208 on the force measurement assembly 202 is not just random, but rather the stochastic signal itself controlling the perturbation has both random amplitude and frequency content. Advantageously, the displacement of the force measurement assembly 202 does not have a consistent or repeating pattern that can be learned by the subject 208 over time. The stochastic signal generated by the programmable logic controller 272 or the data acquisition/data processing device 204 significantly changes the functionality of the force measurement assembly 202 by enabling the force measurement assembly 202 to simulate unexpected, real-life scenarios that could be encountered by the subject 208, such as events suddenly disrupting the subject's normal balance. As such, controlling the force measurement assembly 202 using the stochastic signal enables the force measurement assembly 202 to model real-life conditions encountered by the subject 208 so that the testing and/or training of the subject 208 using the force measurement assembly 202 may be greatly enhanced.

In one or more alternative embodiments, during a testing or training trial, three (3) stochastic signals comprising respective sets of random values are generated (i.e., one for frequency, rotational amplitude, and translational amplitude). Rotational and translational amplitude are both calculated because they use different scale factors, and this allows the force measurement assembly 202 and visual scenes described hereinafter to be displaced in different ways. In these one or more embodiments, the level setting for rate and magnitude determines the scalar each random value will be multiplied by. In these one embodiments, the stochastic signal may comprise a sinusoidal waveform with randomly generated values for the amplitude (i.e., rotational or translation amplitude) and frequency. In these one or more embodiments, the displacement and velocity of the force measurement assembly 202 are given by the following equations:

$$x = A \sin(\omega t + \varphi) \quad (15)$$

$$\dot{x} = A\omega \cos(\omega t + \varphi) \quad (16)$$

where:
A: amplitude; and
ω: angular frequency.

Then, as shown in the equations below, the amplitude values are calculated by generating random values, scaling by the selected level (i.e., ALevel, which is the amplitude level setting 1 to 9), and adding that value to a minimum desirable magnitude. The set is uniformly distributed between the minimum amplitude and the maximum for the selected level. For example, the rotational amplitude may be computed as follows:

$$\text{Amplitude(Rotation)} = 0.5 + A\text{Level} * R \text{ and } (0,1) \quad (17)$$

Similarly, the translational amplitude may be computed as follows:

$$\text{Amplitude(Translation)} = 6 + 6 * A\text{Level} * R \text{ and } (0,1) \quad (18)$$

In these one or more embodiments, the frequency values may be calculated with amplitude-frequency coupling or without amplitude-frequency coupling. When the frequency values are calculated with amplitude-frequency coupling, the process of generating the set of frequency values is very similar to the process of generating the amplitude values described above in equations (17) and (18). A random number is generated, added to an offset, and scaled by the level (i.e., wLevel, which is the angular frequency level setting 1 to 9). That value is then divided by its associated amplitude, so that sinusoids with small amplitudes tend to have high frequency components and vice versa. This calculation procedure helps prevent cases where a sinusoid can have low amplitude and frequency components and the force measurement assembly 202 moves very slowly. For example, with amplitude-frequency coupling, the angular frequency may be calculated as follows:

$$w = \frac{wLevel}{9} * (0.3 + 0.7 * Rand(0, 1)) * \frac{\text{Max Velocity}}{\text{Amplitude}} \quad (19)$$

Conversely, when the frequency values are calculated without amplitude-frequency coupling, the process of generating the set of frequency values is very similar to the process previously described. The difference is that instead of dividing by the associated amplitude component's value, each frequency value is divided by the selected amplitude level (ALevel 1 to 9). This prevents the force measurement assembly 202 from exceeding its maximum safe velocity (e.g., 48.5 degrees per second) while also maintaining increased "randomness" compared to the coupled method. For example, without amplitude-frequency coupling, the angular frequency may be calculated as follows:

$$w = \frac{wLevel}{9} * (0.3 + 0.7 * Rand(0, 1)) * \frac{\text{Max Velocity}}{0.5 + ALevel} \qquad (20)$$

In these one or more embodiments, each pair of frequency and amplitude values determines the frequency and amplitude of a half sinusoid. A sequence of these half sinusoids makes up the random signal which can be used to move the force measurement assembly 202 or visual scene described hereinafter. If the force measurement assembly 202 and displacement of the visual scene are synchronized and moving randomly, the frequency values are determined by the movement type and amplitude of the force measurement assembly 202.

Next, the manner in which the programmable logic controller 272 and data acquisition/data processing device 204 of the balance perturbation system 200 are specially programmed to further perturb the balance of the subject 208 disposed on the force measurement assembly 202 by displacing the one or more scenes on the output screen 268 of the subject visual display device 207. As explained above, the data acquisition/data processing device 204 is operatively coupled to the programmable logic controller 272 of the force measurement assembly 202. In one illustrative embodiment, the programmable logic controller 272 (i.e., a data processing device) is specially programmed to generate a first perturbation signal for introducing a first type of perturbation to the force measurement assembly 202 and a second perturbation signal for introducing a second type of perturbation to the force measurement assembly 202. As will be explained hereinafter, the first and second perturbation signals, which are used to control the angular and translational displacement positions of the force measurement assembly 202, may also be used to control the displacement of one or more scenes on the output screen 268 of the subject visual display device 207. As explained above, in an alternative illustrative embodiment, the data acquisition/data processing device 204, rather than the programmable logic controller 272, may be specially programmed to generate the first and second perturbation signals for controlling the displacement of the force measurement assembly 202 and the displacement of the one or more scenes on the output screen 268 of the subject visual display device 207. In one or more other alternative embodiments, as will be described in further detail hereinafter, the displacement of the one or more scenes on the output screen 268 of the subject visual display device 207 may be independent of the force measurement assembly 202, and the scenes may be displaced without displacing the force measurement assembly 202.

Exemplary perturbation signals generated by the programmable logic controller 272 or the data acquisition/data processing device 204 for controlling the displacement of one or more scenes on the output screen 268 of the subject visual display device 207 are illustrated in FIGS. 33-42. The exemplary perturbation signals depicted in these figures will be described in detail hereinafter.

In the illustrative embodiment, the perturbation signal for controlling the displacement of one or more scenes on the output screen 268 of the subject visual display device 207 comprises a stochastic signal. The programmable logic controller 272 or the data acquisition/data processing device 204 is specially programmed to control the displacement of one or more scenes on the output screen 268 of the subject visual display device 207 so as to make the one or more scenes rotate or translate in an oscillatory manner on the output screen 268 of the subject visual display device 207. As will be described hereinafter, the stochastic signal may be of uniform or normal distribution. The stochastic signal is capable of perturbing the subject's somatosensory system while the subject 208 is disposed on the force measurement assembly 202.

In the illustrative embodiment, the generation of the screen image perturbation signal by the programmable logic controller 272 or the data acquisition/data processing device 204 comprises a plurality of different steps. Initially, by utilizing the input devices 232, 234 of the data acquisition/data processing device 204 (e.g., the keyboard 232 and/or mouse 234), a user enters one or more perturbation levels that correspond to at least one of: (i) the stochastic signal base amplitude, and (ii) a frequency of the stochastic signal (i.e., the cut-off frequency of the stochastic signal), and the user additionally may select the type of signal for the stochastic displacement (i.e., uniform or normal). For example, in one exemplary embodiment, a user may have the following six selection options: (i) choosing any one of levels 1 to 10 for the amplitude of the translational screen image perturbation, (ii) choosing any one of levels 1 to 10 for the frequency of the translational screen image perturbation, (iii) selecting the type of signal for the translation screen image perturbation, (iv) choosing any one of levels 1 to 10 for the amplitude of the rotational screen image perturbation, (v) choosing any one of levels 1 to 10 for the frequency of the rotational screen image perturbation, and (vi) selecting the type of signal for the rotational screen image perturbation. In this exemplary embodiment, the first value of the amplitude for both the translational and rotational screen image perturbation is zero (i.e., level 1 corresponds to a zero amplitude, then each of the successive levels may incrementally increase the angle by approximately 18 degrees for rotation about the x-axis and approximately 0.20 meters for translation along the x-axis). As such, when level 1 is selected for either of the two amplitudes, the screen image will not be displaced in that direction. That way, the user is able to customize the displacement of the screen image such that the screen image only undergoes rotation, only undergoes translation, or undergoes both rotation and translation. In this exemplary embodiment, the first value of the frequency for both the translational and rotational screen image perturbation may be 5 Hertz, and then each of the successive levels may incrementally increase the frequency by approximately 6 Hertz, up to a maximum frequency of 60 Hertz. In other embodiments, smaller frequency increments may be used for the successive levels, such as 5 Hertz. In one or more embodiments, the rotational displacement of the screen image or scene comprises rotating the screen image or scene on the output screen 268 of the visual display device 207 about an imaginary horizontal rotational axis disposed transversely across a width of the visual display device 207. Also, in one or more embodiments, the translational displacement of the screen image or scene comprises translating the screen image or scene on the output screen 268 of the visual display device 207 such that the screen image or scene on the output screen 268 of the visual display device 207 moves towards the subject 208 on the force measurement assembly 202 and away from the subject 208 on the force measurement assembly 202 (i.e., as if a user is zooming in and out on the screen image).

In the illustrative embodiment, the user may select level 1 through 10 for the amplitude of the screen image rotation. The rotational amplitude of the screen image displacement about the x-axis 424, y-axis 426, or z-axis 428 may range from −90 degrees to 90 degrees (see FIG. 19). The first selected level determines the maximum amplitude of the stochastic signal for the angle of rotation. The user may also select level 1 through 10 for the frequency of screen image rotation. The second selected level determines the maximum frequency of the stochastic signal for angle of rotation. Additionally, in the illustrative embodiment, the user may select the type of signal for stochastic angular displacement of the screen image (i.e. a uniform or normal stochastic signal). Further, the user may select level 1 through 10 for the amplitude of screen image translation. The translational amplitude of the screen image displacement along the x-axis may range from −0.5 meters to 0.5 meters. The third selected level determines the maximum amplitude of the stochastic signal for the translational displacement. The user may also select level 1 through 10 for the frequency of the screen image translation. The fourth selected level determines the maximum frequency of the stochastic signal for translational displacement. Similar to the angle of rotation, the user also may select the type of signal for stochastic translational displacement of the screen image (i.e. a uniform or normal stochastic signal). The above selections enable the user to execute the rotational and translational screen image perturbation either independently or simultaneously.

After the user utilizes the input devices 232, 234 of the data acquisition/data processing device 204 to input the screen image perturbation levels and the signal types, the programmable logic controller 272 or the data acquisition/data processing device 204 generates the uniform or normal stochastic signals based upon the amplitude and frequency values entered by the user. The amplitude values entered by the user determines the upper and lower bounds of the stochastic signals generated by the programmable logic controller 272 or the data acquisition/data processing device 204, while the cut-off frequency values entered by the user determines the upper frequency limits of the stochastic signals generated by the programmable logic controller 272 or the data acquisition/data processing device 204. Finally, the data acquisition/data processing device 204 controls the angular displacement and/or translational displacement of the one or more screen images or scenes on the output screen 268 of the subject visual display device 207. Each of these steps will be described in further detail hereinafter. When the programmable logic controller 272 generates the stochastic signals, the amplitudes, the cut-off frequencies, and the signal types of the stochastic signals are transmitted from the data acquisition/data processing device 204 to the programmable logic controller 272 so that the stochastic signals are able to be generated by the programmable logic controller 272.

Also, in another mode of operation of the illustrative embodiment, the user has the option of entering a sequencing routine for the displacement of the screen images or scenes on the output screen 268 of the subject visual display device 207, wherein the rotational and translational displacements are sequenced. In the illustrative embodiment, the sequencing routine allows the user to enter up to 10 signal inputs. For example, one possible sequencing routine could include the following ten displacement tasks executed in a continuous manner while the subject is disposed on the displaceable force measurement assembly 202 and viewing a screen image on the output screen 268 of the subject visual display device 207: (1) translation displacement of the screen image along the z-axis, amplitude 1000 mm, frequency 5 Hz, and signal type: uniform; (2) translational displacement of the screen image along the z-axis, amplitude 2000 mm, frequency 60 Hz, and signal type: normal; (3) rotational displacement of the screen image about the x-axis, amplitude 45 degrees, frequency 3 Hz, and signal type: normal; (4) translational displacement of the screen image along the z-axis, amplitude 1500 mm, frequency 20 Hz, and signal type: uniform, (5) rotational displacement of the screen image about the x-axis, amplitude −80 degrees, frequency 50 Hz, and signal type: uniform; (6) rotational displacement of the of the screen image about the x-axis, amplitude 15 degrees, frequency 20 Hz, and signal type: normal; (7) translation displacement of the screen image along the z-axis, amplitude 200 mm, frequency 10 Hz, and signal type: uniform; (8) translation displacement of the screen image along the z-axis, amplitude 5000 mm, frequency 2 Hz, and signal type: normal; (9) rotational displacement of the screen image about the x-axis, amplitude −90 degrees, frequency 1 Hz, signal type: uniform; and (10) translation displacement of the screen image along z-axis, amplitude 100 mm, frequency 50 Hz, and signal type: uniform. In this mode of operation, the user would also be prompted to enter a time duration for each of the ten displacement tasks (e.g., 10 seconds for the first task, 6 seconds for the second task, etc.). This exemplary sequencing routine would create a predetermined motion profile of random perturbations for the screen image on the output screen 268 of the subject visual display device 207. This type of sequencing routine may be used to increase the difficulty level of the balance testing for the subject. While all of the screen image translational displacements of the above exemplary sequencing routine are along the z-axis, and all of the screen image rotational displacements are about the x-axis, it is to be understood that, in other alternative sequencing routines, the translational displacements may also occur along the x-axis and y-axis and the rotational displacements may also occur about the y-axis and z-axis. Also, in one or more embodiments, a user may select a translational displacement about one or a combination of the x, y, and z-axes during a sequencing routine. Similarly, the user may select a rotational displacement about one or a combination of the x, y, and z-axes during a sequencing routine.

In yet another mode of operation of the illustrative embodiment, the user may be permitted to enter a stochastic amplitude value in the range between zero and approximately 90 degrees, inclusive (or between zero and 90 degrees, inclusive) for the rotational displacement of the screen image on the output screen 268 of the subject visual display device 207 about the x-axis, y-axis, or z-axis, between zero and approximately 0.5 meters, inclusive (or between zero and 0.5 meters, inclusive) for the translational displacement of the screen image on the output screen 268 of the subject visual display device 207 along the x-axis, between zero and approximately 0.75 meters, inclusive (or between zero and 0.75 meters, inclusive) for the translational displacement of the screen image on the output screen 268 of the subject visual display device 207 along the y-axis, and between zero and approximately 1.0 meters, inclusive (or between −1.0 and 1.0 meters, inclusive) for the translational displacement of the screen image on the output screen 268 of the subject visual display device 207 along the z-axis. Similarly, in this mode of operation of the illustrative embodiment, the user may be permitted to enter a cut-off frequency value in the range between approximately 0.01 Hertz and approximately 60 Hertz, inclusive (or between 0.01 Hertz and 60 Hertz, inclusive) for each of the rotational and translational displacements of the screen image on the output screen 268 of the subject visual display device 207. Although, it is to be understood that, in other modes of operation, the translational displacements may be greater than those described above (the actual values depend on the scene/image).

In addition to entering the amplitude, cut-off frequency, and signal type of the stochastic signals for rotational and translational displacement of the screen image on the output screen 268 of the subject visual display device 207, the user is also able to selectively regulate the beginning and end of the stochastic signals by pressing a graphical start button on the operator display 230 to initiate the stochastic signals, and then by subsequently pressing a graphical stop button on the operator display 230 to end the stochastic signals (i.e., when the display is a touchscreen).

Figure 33:
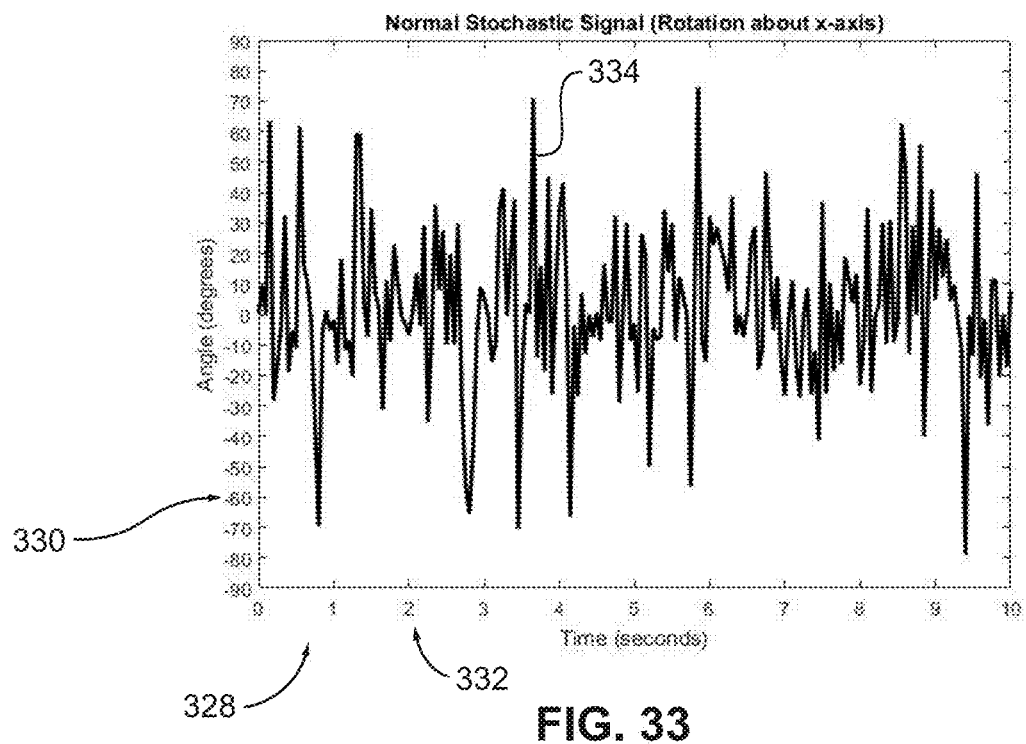
FIG. 33 is a graph illustrating a normal stochastic perturbation signal for controlling the angular displacement of a scene on the output screen of a subject visual display device about the x-axis.
Figure 34:
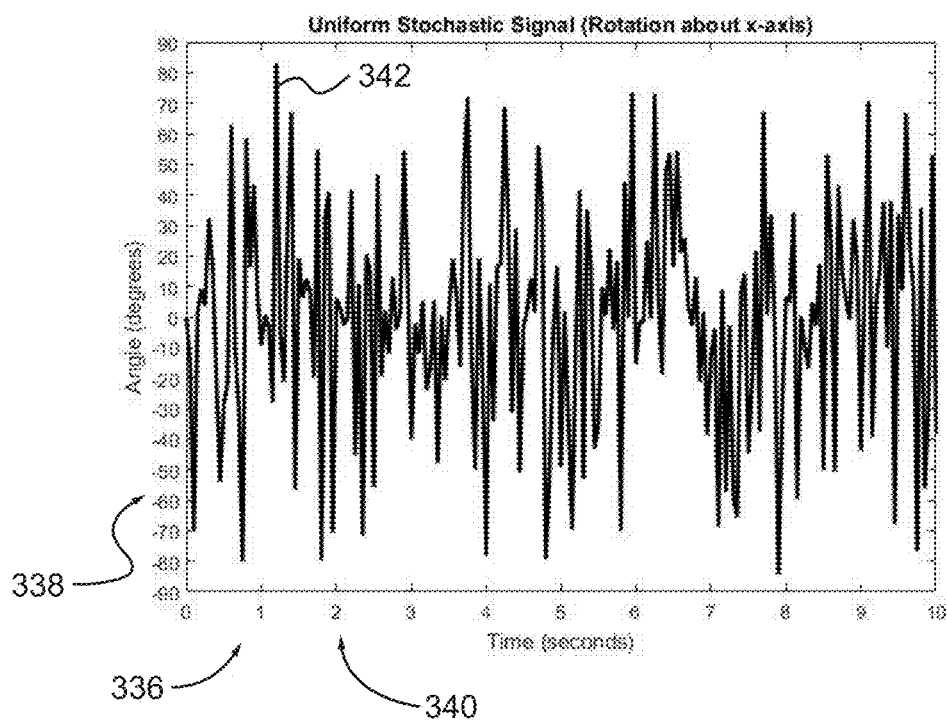
FIG. 34 is a graph illustrating a uniform stochastic perturbation signal for controlling the angular displacement of a scene on the output screen of a subject visual display device about the x-axis.

In the illustrative embodiment, the rotational and translational displacements of the screen image on the output screen 268 of the subject visual display device 207 of the balance perturbation system 200 are each capable of being controlled simultaneously and independently. An exemplary normal stochastic signal for the screen image rotational displacement that is generated by the programmable logic controller 272 or the data acquisition/data processing device 204 is illustrated in the graph 328 of FIG. 33. In FIG. 33, the screen image or scene is being rotated about an imaginary horizontal rotational axis disposed transversely across a width of the visual display device 207 (i.e., about the x-axis 424 in FIG. 19). As shown in FIG. 33, the y-axis 330 of the graph 328 is the screen image displacement angle in degrees, while the x-axis 332 of the graph 328 is the time in seconds (sec). In the graph 328 of FIG. 33, it can be seen that the normal stochastic signal curve 334 oscillates between a minimum lower limit of approximately −80 degrees and a maximum upper limit of approximately 75 degrees over a time duration of approximately 10 seconds. Similarly, an exemplary uniform stochastic signal for the screen image rotational displacement that is generated by the programmable logic controller 272 or the data acquisition/data processing device 204 is illustrated in the graph 336 of FIG. 34. In FIG. 34, the screen image or scene is being rotated about an imaginary horizontal rotational axis disposed transversely across a width of the visual display device 207 (i.e., about the x-axis 424 in FIG. 19). As shown in FIG. 34, the y-axis 338 of the graph 336 is the screen image displacement angle in degrees, while the x-axis 340 of the graph 336 is the time in seconds (sec). In the graph 336 of FIG. 34, it can be seen that the uniform stochastic signal curve 342 oscillates between a minimum lower limit of approximately −85 degrees and a maximum upper limit of approximately 85 degrees over a time duration of approximately 10 seconds.

Figure 35:
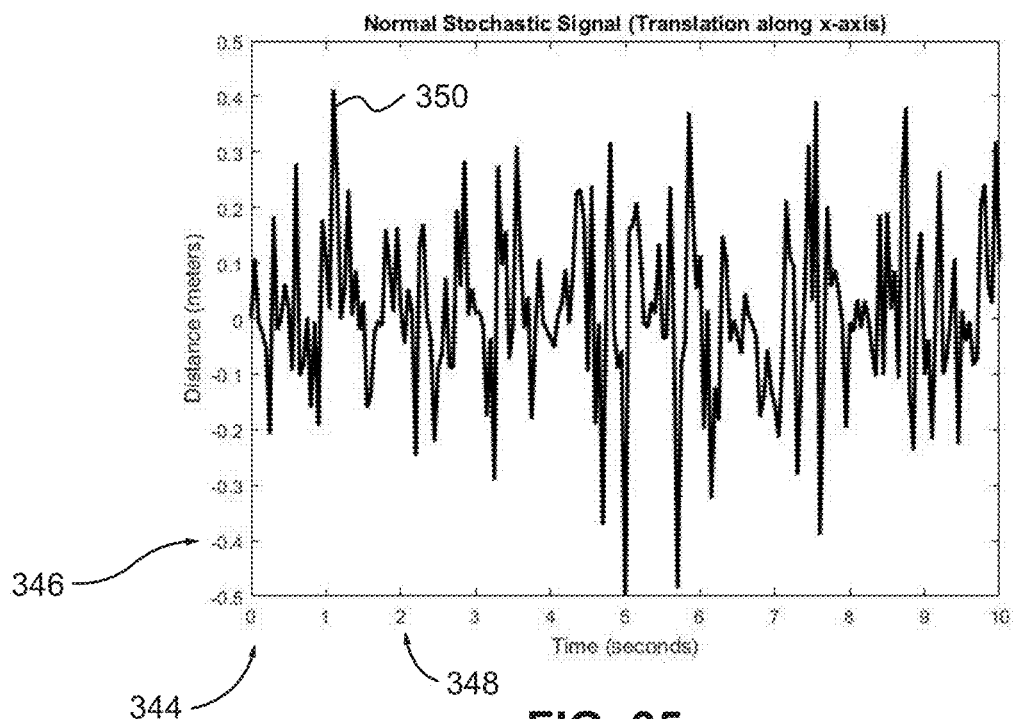
FIG. 35 is a graph illustrating a normal stochastic perturbation signal for controlling the translational displacement of a scene on the output screen of a subject visual display device along the x-axis.
Figure 36:
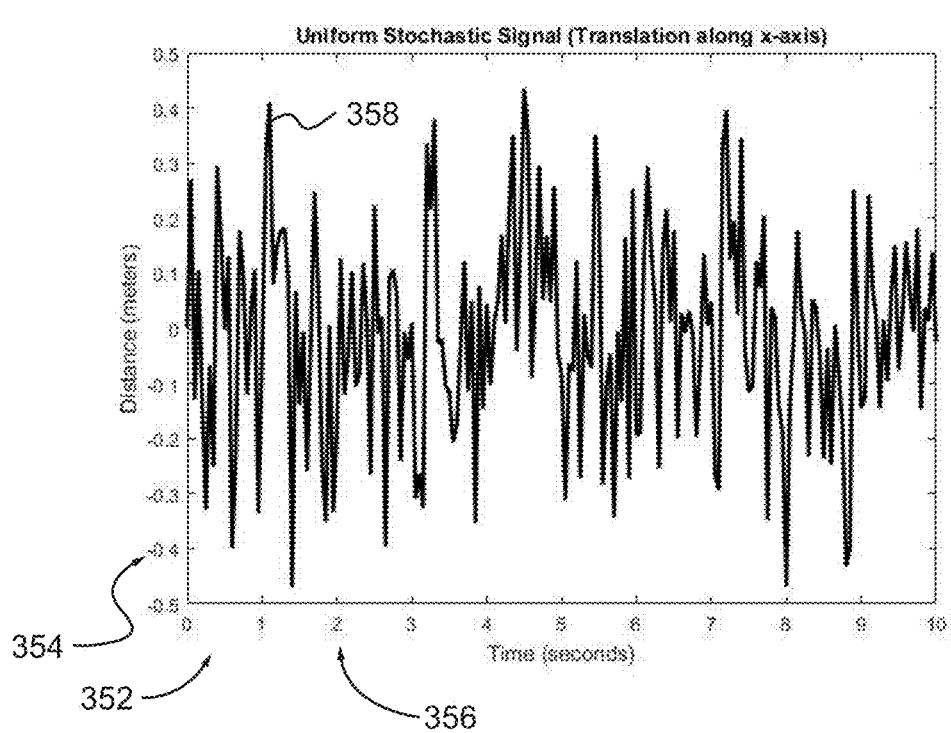
FIG. 36 is a graph illustrating a uniform stochastic perturbation signal for controlling the translational displacement of a scene on the output screen of a subject visual display device along the x-axis.

As another example, an exemplary normal stochastic signal for screen image translational displacement that is generated by the programmable logic controller 272 or the data acquisition/data processing device 204 is illustrated in the graph 344 of FIG. 35. In FIG. 35, the screen image or scene is being translated along an imaginary horizontal axis disposed transversely across a width of the visual display device 207 (i.e., along the x-axis 424 in FIG. 19). As shown in FIG. 35, the y-axis 346 of the graph 344 is the screen image translational displacement (i.e., screen image transverse displacement) in meters, while the x-axis 348 of the graph 344 is the time in seconds (sec). In the graph 344 of FIG. 35, it can be seen that the normal stochastic signal curve 350 oscillates between a minimum lower limit of approximately −0.5 meters and a maximum upper limit of approximately 0.42 meters over a time duration of approximately 10 seconds. Similarly, an exemplary uniform stochastic signal for screen image translational displacement that is generated by the programmable logic controller 272 or the data acquisition/data processing device 204 is illustrated in the graph 352 of FIG. 36. In FIG. 36, the screen image or scene is being translated along an imaginary horizontal axis disposed transversely across a width of the visual display device 207 (i.e., along the x-axis 424 in FIG. 19). As shown in FIG. 36, the y-axis 354 of the graph 352 is the screen image translational displacement (i.e., screen image transverse displacement) in meters, while the x-axis 356 of the graph 352 is the time in seconds (sec). In the graph 352 of FIG. 36, it can be seen that the uniform stochastic signal curve 358 oscillates between a minimum lower limit of approximately −0.475 meters and a maximum upper limit of approximately 0.45 meters over a time duration of approximately 10 seconds.

Figure 37:
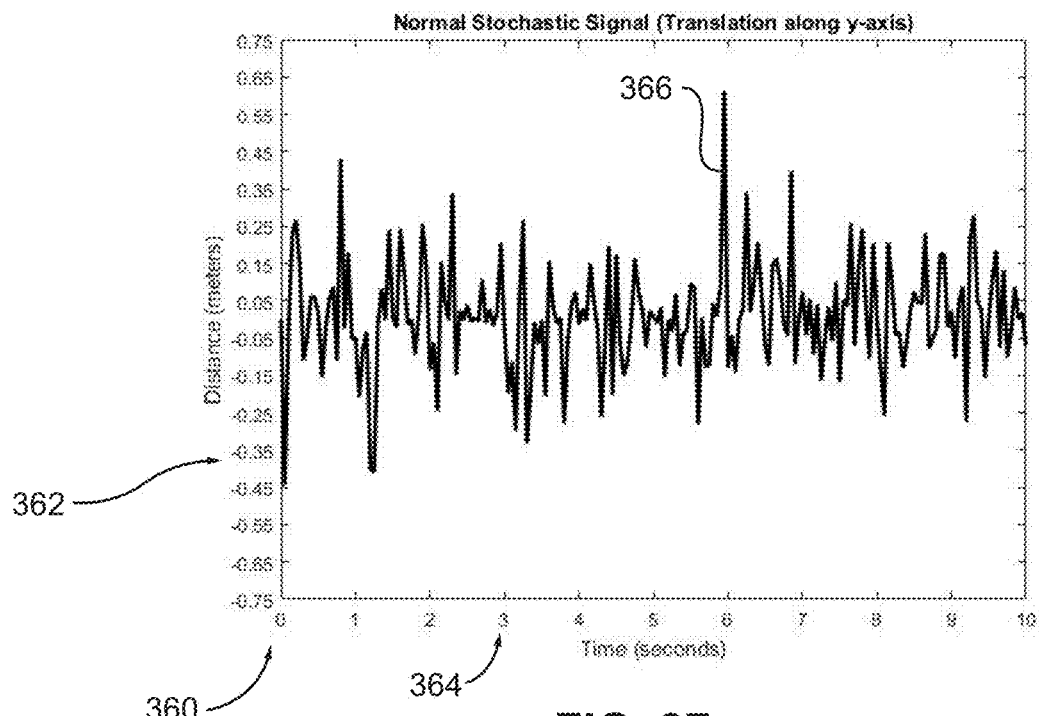
FIG. 37 is a graph illustrating a normal stochastic perturbation signal for controlling the translational displacement of a scene on the output screen of a subject visual display device along the y-axis.
Figure 38:
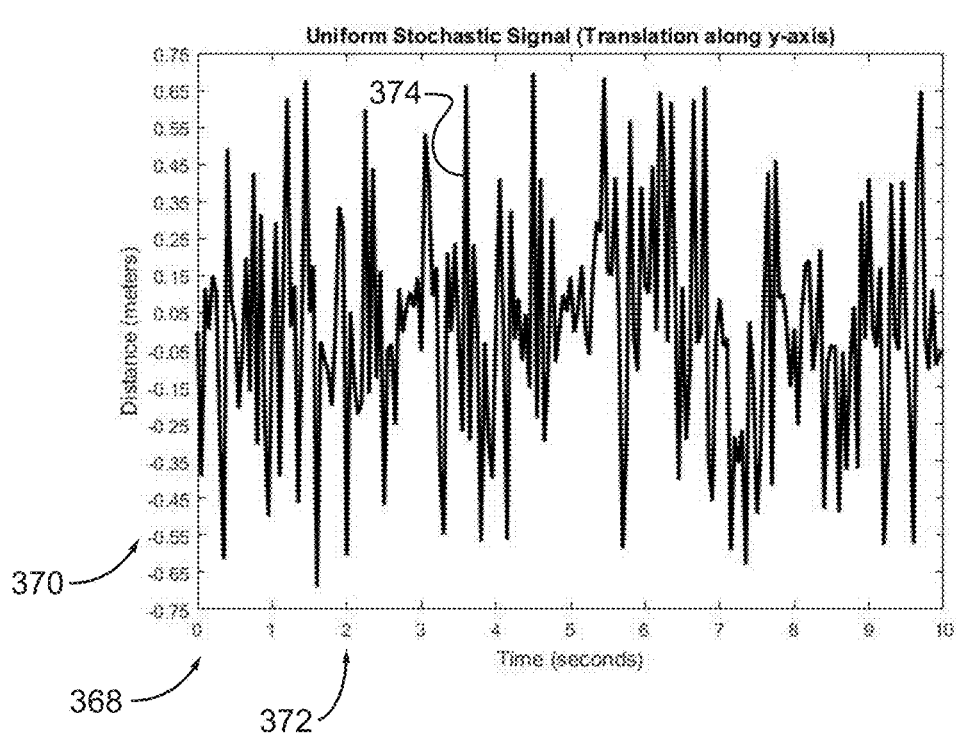
FIG. 38 is a graph illustrating a uniform stochastic perturbation signal for controlling the translational displacement of a scene on the output screen of a subject visual display device along the y-axis.

As yet another example, an exemplary normal stochastic signal for screen image translational displacement that is generated by the programmable logic controller 272 or the data acquisition/data processing device 204 is illustrated in the graph 360 of FIG. 37. In FIG. 37, the screen image or scene is being translated along an imaginary vertical axis disposed vertically relative to the visual display device 207 (i.e., along the y-axis 426 in FIG. 19). As shown in FIG. 37, the y-axis 362 of the graph 360 is the screen image translational displacement (i.e., screen image vertical displacement) in meters, while the x-axis 364 of the graph 360 is the time in seconds (sec). In the graph 360 of FIG. 37, it can be seen that the normal stochastic signal curve 366 oscillates between a minimum lower limit of approximately −0.45 meters and a maximum upper limit of approximately 0.60 meters over a time duration of approximately 10 seconds. Similarly, an exemplary uniform stochastic signal for screen image translational displacement that is generated by the programmable logic controller 272 or the data acquisition/data processing device 204 is illustrated in the graph 368 of FIG. 38. In FIG. 38, the screen image or scene is being translated along an imaginary vertical axis disposed vertically relative to the visual display device 207 (i.e., along the y-axis 426 in FIG. 19). As shown in FIG. 38, the y-axis 370 of the graph 368 is the screen image translational displacement (i.e., screen image vertical displacement) in meters, while the x-axis 372 of the graph 368 is the time in seconds (sec). In the graph 368 of FIG. 38, it can be seen that the uniform stochastic signal curve 374 oscillates between a minimum lower limit of approximately −0.70 meters and a maximum upper limit of approximately 0.70 meters over a time duration of approximately 10 seconds.

Figure 39:
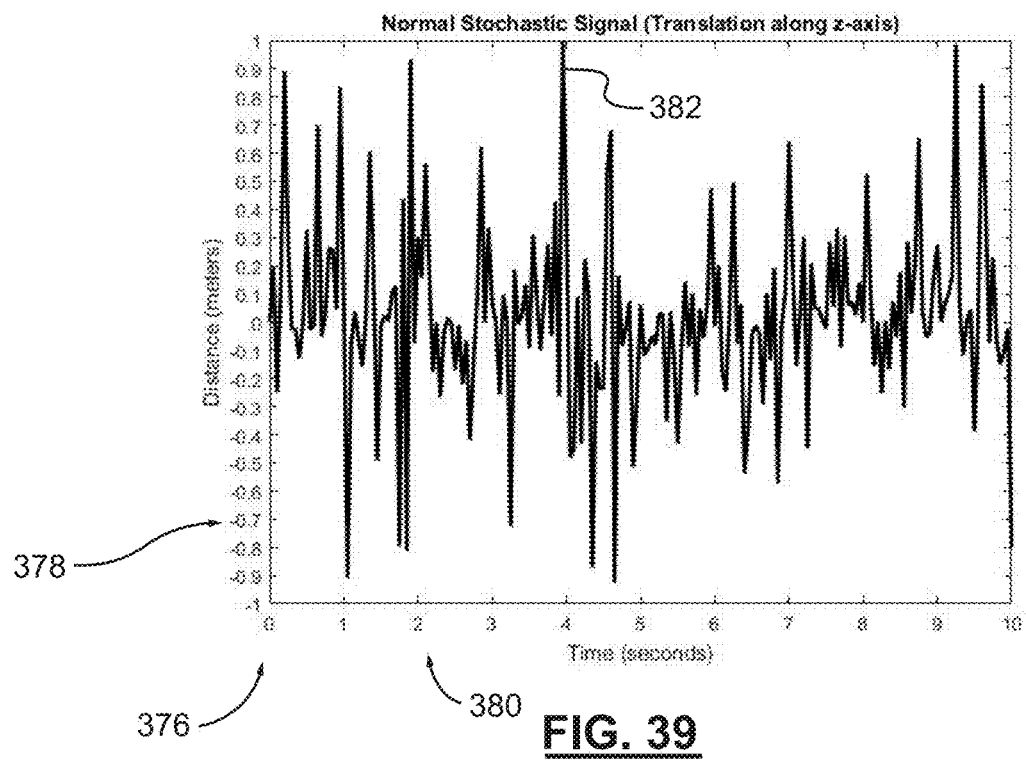
FIG. 39 is a graph illustrating a normal stochastic perturbation signal for controlling the translational displacement of a scene on the output screen of a subject visual display device along the z-axis.
Figure 40:
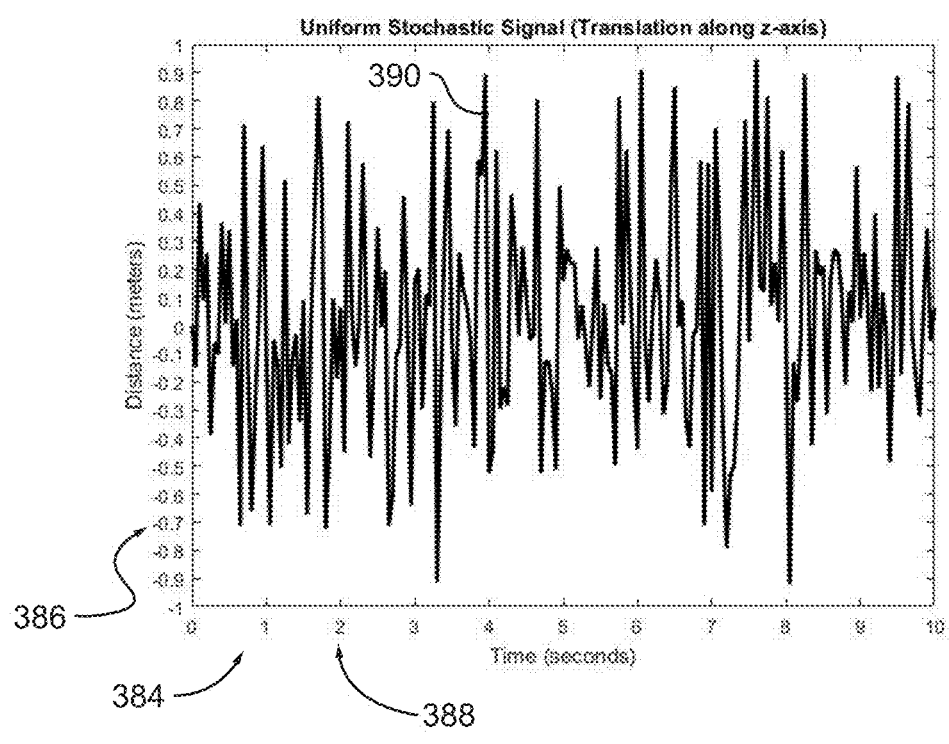
FIG. 40 is a graph illustrating a uniform stochastic perturbation signal for controlling the translational displacement of a scene on the output screen of a subject visual display device along the z-axis.

As still another example, an exemplary normal stochastic signal for screen image translational displacement that is generated by the programmable logic controller 272 or the data acquisition/data processing device 204 is illustrated in the graph 376 of FIG. 39. In FIG. 39, the screen image or scene is being translated along an imaginary horizontal axis disposed anteriorly and posteriorly relative to the visual display device 207 (i.e., along the z-axis 428 in FIG. 19). As shown in FIG. 39, the y-axis 378 of the graph 376 is the screen image translational displacement (i.e., screen image anterior/posterior displacement) in meters, while the x-axis 380 of the graph 376 is the time in seconds (sec). In the graph 376 of FIG. 39, it can be seen that the normal stochastic signal curve 382 oscillates between a minimum lower limit of approximately −0.9 meters and a maximum upper limit of approximately 1.0 meter over a time duration of approximately 10 seconds. Similarly, an exemplary uniform stochastic signal for screen image translational displacement that is generated by the programmable logic controller 272 or the data acquisition/data processing device 204 is illustrated in the graph 384 of FIG. 40. In FIG. 40, the screen image or scene is being translated along an imaginary horizontal axis disposed anteriorly and posteriorly relative to the visual display device 207 (i.e., along the z-axis 428 in FIG. 19). As shown in FIG. 40, the y-axis 386 of the graph 384 is the screen image translational displacement (i.e., screen image anterior/posterior displacement) in meters, while the x-axis 388 of the graph 384 is the time in seconds (sec). In the graph 384 of FIG. 40, it can be seen that the uniform stochastic signal curve 390 oscillates between a minimum lower limit of approximately −0.9 meters and a maximum upper limit of approximately 0.95 meters over a time duration of approximately 10 seconds.

Figure 41:
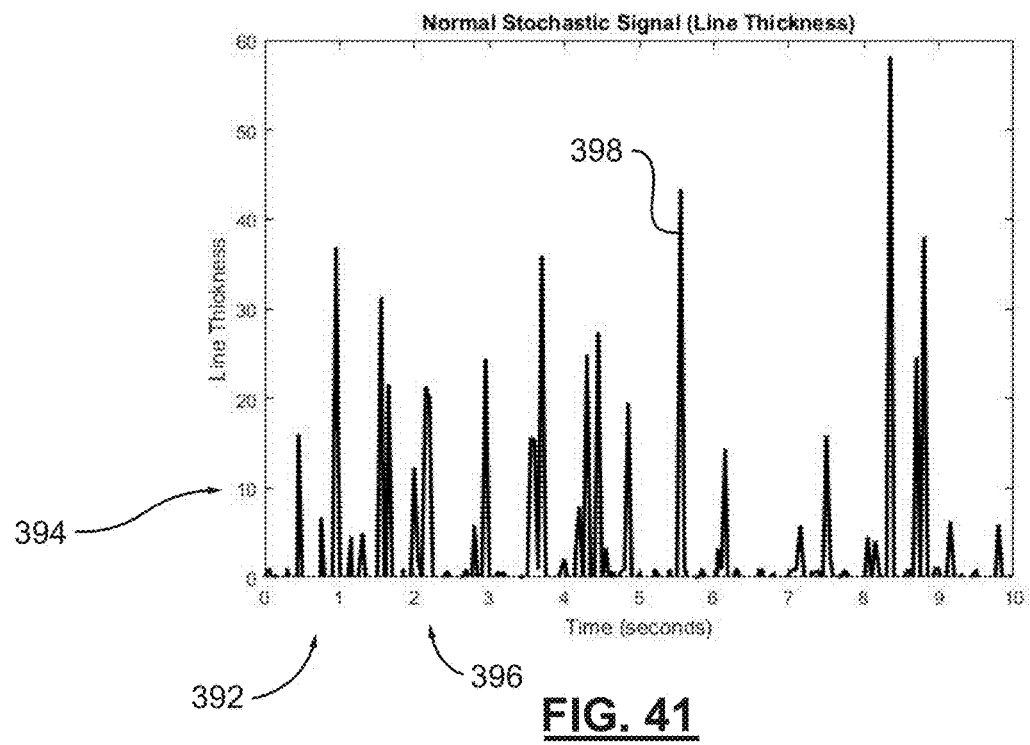
FIG. 41 is a graph illustrating a normal stochastic perturbation signal for controlling line thickness in a scene on the output screen of a subject visual display device.
Figure 42:
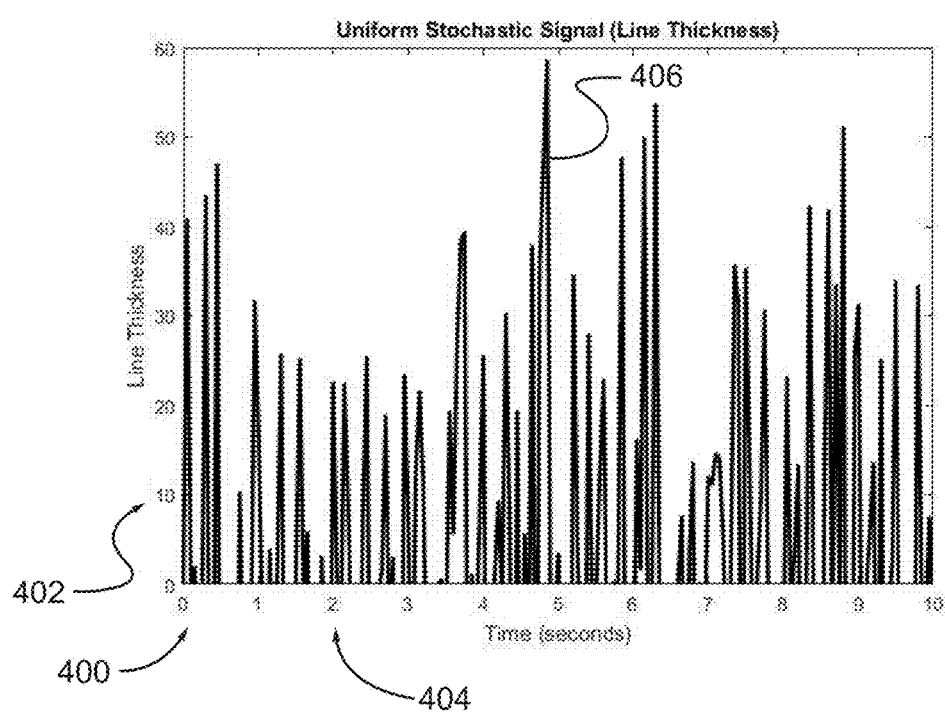
FIG. 42 is a graph illustrating a uniform stochastic perturbation signal for controlling line thickness in a scene on the output screen of a subject visual display device.

As yet another example, an exemplary normal stochastic signal for controlling the line thickness in a scene or screen image that is generated by the programmable logic controller 272 or the data acquisition/data processing device 204 is illustrated in the graph 392 of FIG. 41. In one or more embodiments, the line thickness of one or more elements in the scene or screen image may be controlled by applying the normal stochastic signal to a tile size parameter associated with the scene or screen image so as to stochastically increase and decrease the line thickness of the one or more elements in the scene or screen image (e.g., increase or decrease the thicknesses of the lines in the scenes of FIGS. 45 and 46). As shown in FIG. 41, the y-axis 394 of the graph 392 is the line thickness of one or more elements in the scene or screen image ranging from 0 to 60, while the x-axis 396 of the graph 392 is the time in seconds (sec). In the graph 392 of FIG. 41, it can be seen that the normal stochastic signal curve 398 oscillates between a minimum lower limit of zero and a maximum upper limit of approximately 58 over a time duration of approximately 10 seconds. Similarly, an exemplary uniform stochastic signal for controlling the line thickness in a scene or screen image that is generated by the programmable logic controller 272 or the data acquisition/data processing device 204 is illustrated in the graph 400 of FIG. 42. In one or more embodiments, the line thickness of one or more elements in the scene or screen image may be controlled by applying the uniform stochastic signal to a tile size parameter associated with the scene or screen image so as to stochastically increase and decrease the line thickness of the one or more elements in the scene or screen image (e.g., increase or decrease the thicknesses of the lines in the scenes of FIGS. 45 and 46). As shown in FIG. 42, the y-axis 402 of the graph 400 is the line thickness of one or more elements in the scene or screen image ranging from 0 to 60, while the x-axis 404 of the graph 400 is the time in seconds (sec). In the graph 400 of FIG. 42, it can be seen that the uniform stochastic signal curve 406 oscillates between a minimum lower limit of zero and a maximum upper limit of approximately 58 over a time duration of approximately 10 seconds.

Figure 43:
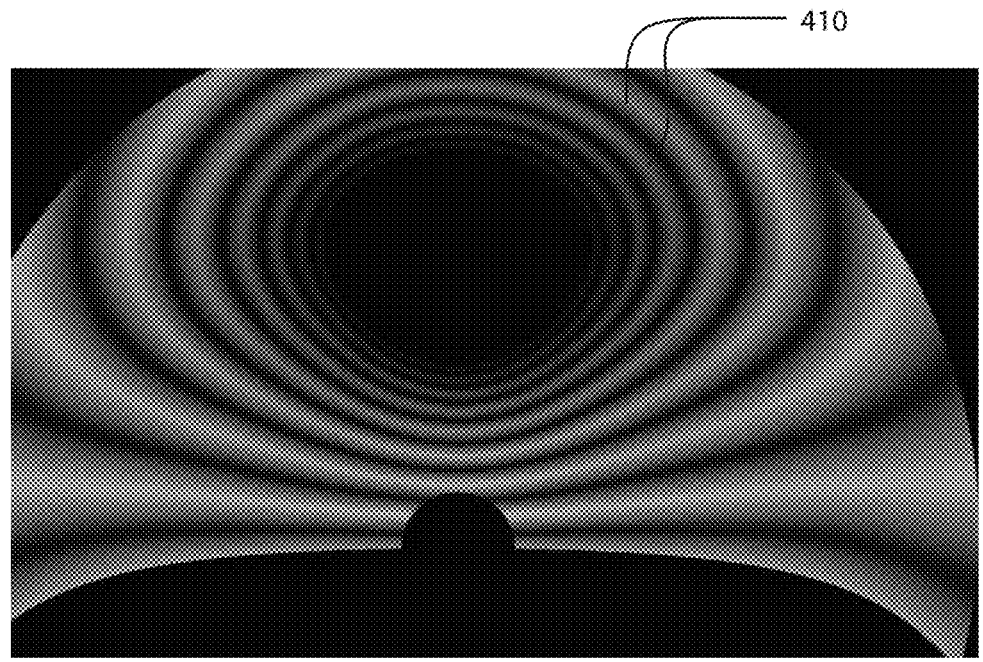
FIG. 43 is a first exemplary scene that may be displayed on the output screen of the visual display device, and may be manipulated using a perturbation signal.
Figure 44:
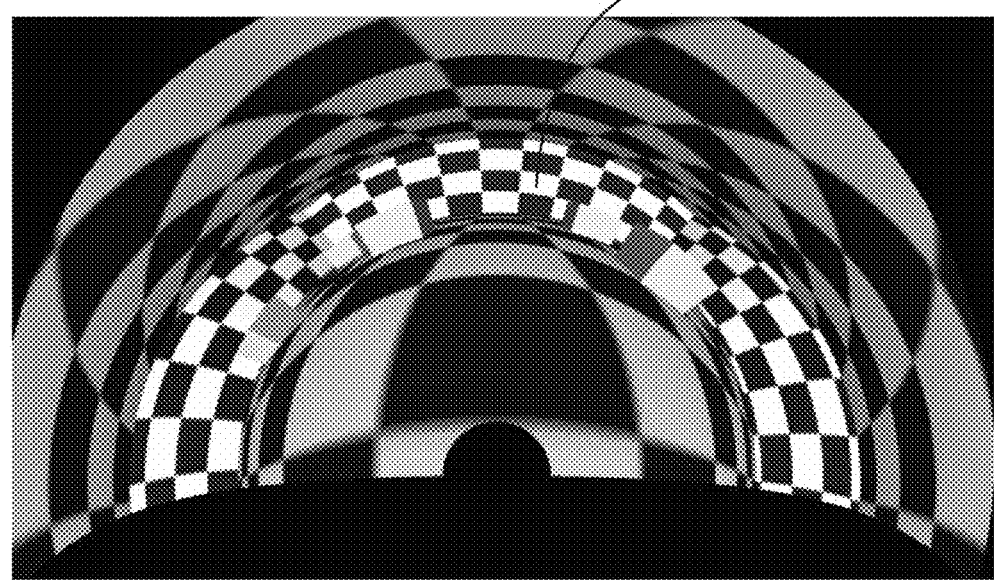
FIG. 44 is a second exemplary scene that may be displayed on the output screen of the visual display device, and may be manipulated using a perturbation signal.
Figure 45:
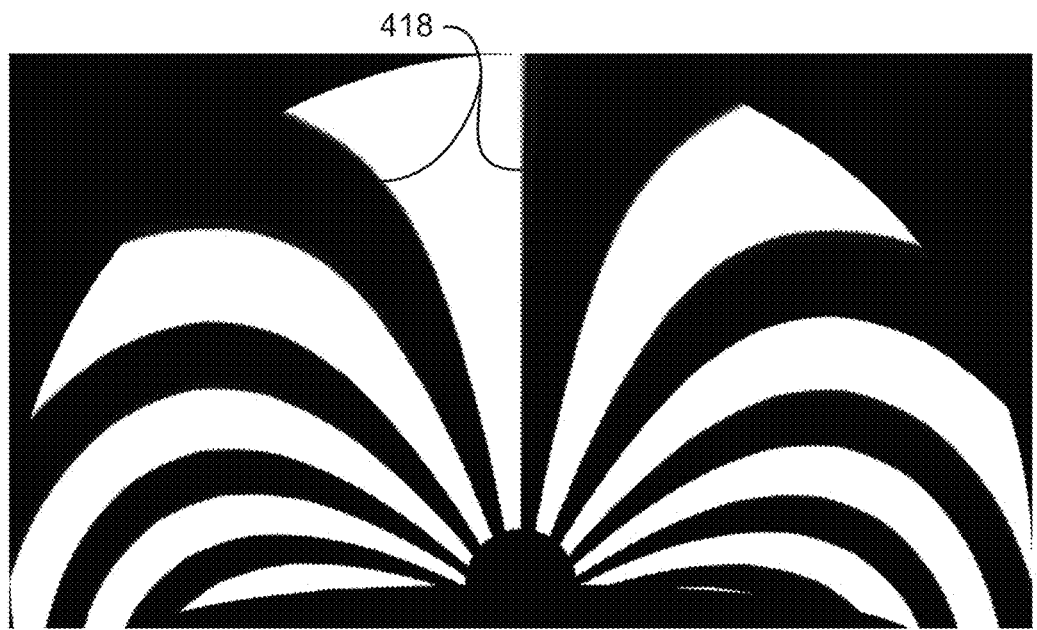
FIG. 45 is a third exemplary scene that may be displayed on the output screen of the visual display device, and may be manipulated using a perturbation signal.
Figure 46:
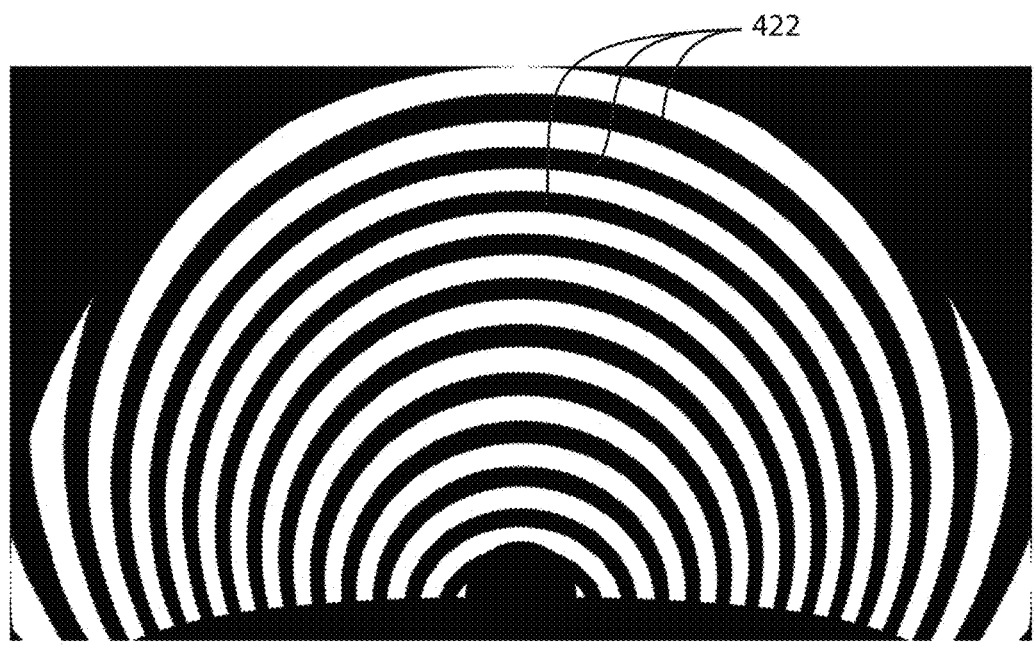
FIG. 46 is a fourth exemplary scene that may be displayed on the output screen of the visual display device, and may be manipulated using a perturbation signal.

Exemplary scenes that may be displaced on the output screen 268 of the subject visual display device 207 using the stochastic signal are illustrated in FIGS. 43-46. In FIG. 43, a scene 408 comprising a plurality of oval-shaped rings 410 is illustrated, while, in FIG. 44, a scene 412 comprising a checkerboard room 414 is illustrated. Either of these two scenes may be rotationally and/or translationally displaced on the output screen 268 of the subject visual display device 207 using the stochastic signal. In FIG. 45, a scene 416 comprising a plurality of vertical lines 418 is illustrated, while, in FIG. 46, a scene 420 comprising a plurality of horizontal lines 422 is illustrated. The thicknesses of the lines 418, 422 depicted in FIGS. 45 and 46 may be manipulated in accordance with the perturbation signals described above in accordance with FIGS. 41 and 42.

In the second step of the process, where a random uniform or normal random signal is generated by the programmable logic controller 272 or the data acquisition/data processing device 204 at the selected cut-off frequency, a random number function or subroutine may be used to generate the uniform signal random numbers (e.g., the DRAND function block in a TwinCAT software package). In the illustrative embodiment, the random number function utilized by the programmable logic controller 272 or the data acquisition/data processing device 204 requires an initial value input for the specification of the random number series. The output returns a pseudo-random number in the range −1.0 to 1.0 with double accuracy. That is, the random number function generates the same sequence of random numbers each time that the same seed is utilized. As such, in an exemplary embodiment, the seed value that is used for the random number function is acquired for each trial from the low DW of the system time, which gives a sufficiently random seed for each trial. That way, the programmable logic controller 272 or the data acquisition/data processing device 204 does not generate the same random number sequence or produce any other perturbation trends from trial to trial. In one or more embodiments, the operating system time stamp is a 64-bit integer value, with a precision of 100 nanoseconds (ns), which is updated with every call of the programmable logic controller (PLC) 272. In one or more embodiments, the low DW (timeLoDW) is the low-value 4 bytes of the time stamp and it changes very rapidly at rate of 0.01 milliseconds (ms). The random signal has a varying frequency. The randomness of the stochastic signal is highly advantageous because the subjects being tested using the balance perturbation system 200 are not able to as easily learn how to overcome a particular perturbation sequence during a testing or training routine. If the perturbation employed was always the same, then eventually subjects would learn how to adapt to the perturbation, and the training would become less effective.

When the user selects a uniform-type stochastic signal, a respective uniform stochastic signal, such as that depicted in FIGS. 34, 36, 38, 40, and 42, is used for controlling a respective one of the rotational and translational displacements of the screen image on the output screen 268 of the subject visual display device 207. However, if the user alternatively selects a normal-type stochastic signal, as described above, two (2) uniform signals U1 and U2 generated using the random number function are converted into normal signal N using the following Box-Muller transform equation:

$$N = \sqrt{-2\ln U1} \cos(2\pi U2) \tag{21}$$

In this illustrative embodiment, as described above for the other illustrative embodiments, the uniform or normal signal is then passed through a fourth order low pass Butterworth filter to limit the frequency component of the signal at a user specified value (i.e., at the frequency entered by the user).

In the illustrative embodiment, prior to the third step of the process, where the programmable logic controller 272 or the data acquisition/data processing device 204 regulates the angular displacement and/or translational displacement of the screen image on the output screen 268 of the subject visual display device 207, the filtered signal is multiplied by the user-specified amplitude value so as to generate the stochastic signals for controlling the angular and/or translational screen image displacements. When the uniform-type stochastic signal is selected by the user, the uniform stochastic signal for controlling the angular and/or translational screen image displacements are determined by the programmable logic controller 272 or the data acquisition/data processing device 204 in accordance with the following equation:

$$\text{Uniform stochastic signal} = \text{filtered uniform signal} * \text{Amplitude} \quad (22)$$

Thus, in accordance with equation (22) above, the uniform stochastic signal is a function of the filtered, randomly-generated uniform signal and the user-specified amplitude value. More specifically, the programmable logic controller 272 or the data acquisition/data processing device 204 determines the uniform stochastic signal by computing the multiplicative product between the filtered uniform signal and the user-specified amplitude value. Alternatively, when the normal-type stochastic signal is selected by the user, the normal stochastic signal for controlling the angular and/or translational screen image displacements is determined by the programmable logic controller 272 or the data acquisition/data processing device 204 in accordance with the following equation:

$$\text{Normal stochastic signal} = \text{filtered normal signal} * \text{Amplitude}/3 \quad (23)$$

Thus, in accordance with equation (23) above, the normal stochastic signal is a function of the filtered, normalized randomly-generated uniform signal and the user-specified amplitude value. More specifically, the programmable logic controller 272 or the data acquisition/data processing device 204 determines the normal stochastic signal by computing the multiplicative product between the filtered normal signal and one-third of the user-specified amplitude value.

In one or more embodiments, the aforedescribed rotational and translational displacement calculations are specially programmed on an embedded computer (e.g., the programmable logic controller 272 or the data acquisition/data processing device 204) that provides a deterministic program cycle time of 1 milliseconds (ms). In other words, the displacement update rate of 1 kilohertz (kHz) is guaranteed by either the hardware architecture of the embedded computer or a real-time operating system (e.g., firmware) that runs on it. In these one or more embodiments, the updated displacements are sent to the data acquisition/data processing device 204, which executes the screen image displacements with a closed-loop rate of 4 kilohertz (kHz). In these one or more embodiments, the firmware of the balance perturbation system 200 controls the screen image perturbations.

In the illustrative embodiment, the programmable logic controller 272 or the data acquisition/data processing device 204 may be specially programmed so as to enable the displacement of the screen image on the output screen 268 of the subject visual display device 207 to be controlled in three different modes: (i) rotational displacement only, (ii) translational displacement only, and (iii) simultaneous rotational and translational displacement. In the simultaneous rotational and translational displacement mode, the programmable logic controller 272 or the data acquisition/data processing device 204 utilizes a first stochastic signal to control the rotational displacement of the screen image on the output screen 268 of the subject visual display device 207, and a second stochastic signal to control the translational displacement of the screen image on the output screen 268 of the subject visual display device 207. In the independent rotational displacement or translational displacement modes, the programmable logic controller 272 or the data acquisition/data processing device 204 utilizes a single stochastic signal to either control the rotational or translational displacement of the screen image on the output screen 268 of the subject visual display device 207. Similar to that described above for the displacement of the force measurement assembly 202, the amplitudes of the stochastic signals used to control the rotational displacement and translational displacement of the screen image on the output screen 268 of the subject visual display device 207 are randomly changing over time (i.e., the amplitudes consistently change over time in a random manner). Similarly, the frequencies of the stochastic signals used to control the rotational displacement and translational displacement of the screen image on the output screen 268 of the subject visual display device 207 randomly change over time (i.e., the frequencies consistently changes over time in a random manner). Thus, advantageously, the programmable logic controller 272 or the data acquisition/data processing device 204 generates stochastic signals with both randomly varying amplitudes and frequencies that results in a random perturbation of the screen image on the output screen 268 of the subject visual display device 207 that is viewable by the subject. The manner of delivery of the visual perturbation to the subject 208 disposed on the force measurement assembly 202 is not just random, but rather the stochastic signal itself controlling the perturbation has both random amplitude and frequency content. Advantageously, the displacement of the screen image on the output screen 268 of the subject visual display device 207 does not have a consistent or repeating pattern that can be learned by the subject 208 over time. The stochastic signal generated by the programmable logic controller 272 or the data acquisition/data processing device 204 significantly changes the functionality of the force measurement system 200 by enabling the system 200 to simulate unexpected, real-life scenarios that could be encountered by the subject 208, such as events suddenly disrupting the subject's normal balance. As such, controlling the screen image on the output screen 268 of the subject visual display device 207 using the stochastic signal enables the force measurement system 200 to model real-life conditions encountered by the subject 208 so that the testing and/or training of the subject 208 using the force measurement assembly 202 may be greatly enhanced.

In one or more alternative embodiments, during a testing or training trial, the screen image on the output screen 268 of the subject visual display device 207 may be displaced as determined by a randomly generated sinusoidal signal as explained above. The value of the sinusoid at any point in time relates to the relative position of the scene image, with home at y=0. So, for each half sinusoid, the amplitude determines how far the screen image is displaced, the frequency determines the time it takes for the scene image to be displaced to the destination and back, and the slope corresponds to the velocity of the movement. If rotation is the movement type, the scene image rotates based on a commanded angle about an imaginary horizontal rotational axis disposed transversely across a width of the visual display device 207. If translation is the movement type, the scene image moves forwards and backwards (i.e., zooms in or out) as the sinusoid swings positive or negative. For example, as described above, the scene 408 in FIG. 43 comprising a plurality of oval-shaped rings 410 or the scene 412 comprising a checkerboard room 414 in FIG. 44 may be rotated or translated in this manner.

In one or more embodiments, the programmable logic controller 272 or the data acquisition/data processing device 204 is configured to control the displacement position of the force measurement assembly 202 using the stochastic signal such that the displacement of the force measurement assembly 202 is synchronized with the displacement of the screen image or scene on the output screen 268 of the visual display device. In these one or more embodiments, when the displacement of the force measurement assembly 202 is synchronized with the displacement of the screen image or scene on the output screen 268 of the visual display device, the amplitude for each uses the same random seed and each signal uses the same frequency values. For example, the force plate angle, when perturbed randomly, is set as an input to the visual scene rotation angle or visual scene translation displacement. As another example, the belt speed of the instrumented treadmill, when perturbed randomly, is set as an input to the optic flow of the scene on the output screen 268 of the visual display device. Also, in addition to, or as an alternative to the displacement, the hardware can control one of the other display parameters described hereinafter in the graphics software platform to perturb the visual scene based on the hardware.

In one or more other embodiments, the programmable logic controller 272 or the data acquisition/data processing device 204 is configured to control the speed set point of the treadmill belts 14, 16 using the stochastic signal such that the displacement of the treadmill belts 14, 16 are synchronized with the displacement of the screen image or scene on the output screen 268 of the visual display device. In these one or more embodiments, when the displacement of the treadmill belts 14, 16 are synchronized with the displacement of the screen image or scene on the output screen 268 of the visual display device, the amplitude for each uses the same random seed and each signal uses the same frequency values.

In one or more alternative embodiments, the screen image or scene on the output screen 268 of the visual display device may be displaced independently from the force measurement assembly 202 or the treadmill belts 14, 16 (i.e., the screen image or scene is not displaced in synchrony with the force measurement assembly 202 or the treadmill belts 14, 16). In these one or more alternative embodiments, when the screen image or scene on the output screen 268 of the visual display device is displaced independently from the force measurement assembly 202 or the treadmill belts 14, 16, the visual perturbation and force measurement assembly perturbation use different sets of amplitude and frequency values. In these one or more embodiments, the stochastic signal can be generated by the programmable logic controller 272 and streamed to the graphics software platform in real-time, or the stochastic signal can be generated using the graphics software platform itself by the data acquisition/data processing device 204. Also, in addition to, or as an alternative to the displacement, the programmable logic controller 272 or the data acquisition/data processing device 204 can control one of the other display parameters described hereinafter to perturb the visual scene.

For example, the programmable logic controller 272 or the data acquisition/data processing device 204 may vary depth of field display parameters in the graphics software platform, such as a focal distance parameter, a smoothness parameter, a focal size parameter, and/or a blur spread parameter. The focal distance parameter sets a value within a range that is limited to the near and far clipping plane of the camera, which essentially sets a distance (up to the maximum far clip plane) where the focus will settle (e.g., a range from 0 to 1000). The smoothness parameter sets a value within a range from zero to the far clip plane, which specifies how smooth the transition is from focus to out of focus (e.g., a range from 0 to 1000). The focal size parameter sets a value within a range from zero to the far clip plane, which specifies the size of the in-focus area (e.g., range from 0 to 1000). The blur spread parameter sets a value within a range from zero to infinity, which specifies the spread of the blur.

As another example, the programmable logic controller 272 or the data acquisition/data processing device 204 may vary camera motion blur display parameters in the graphics software platform, such as a velocity scale blur parameter, a minimum velocity blur parameter, a maximum velocity blur parameter, a velocity downsample parameter, and/or a jitter strength parameter. The velocity scale blur parameter sets a value within a range from zero to infinity that specifies the velocity at which objects will blur, wherein higher is more likely to blur. The minimum velocity blur parameter sets a value within a range from 0 to 10 as a percentage of velocity scale, which specifies the minimum pixel distance at which blur is removed. The maximum velocity blur parameter sets a value within a range from 0 to 10 as a percentage of velocity scale, which specifies the minimum pixel distance at which blur is applied. The velocity downsample parameter sets a value within a range from one to infinity, which affects blur quality with many moving objects, wherein the lower number reduces quality for performance. The jitter strength parameter sets a value within a range from 0 to 10, which helps to prevent ghosting and over-blur, where the value is number of samples to take when calculating blur.

As yet another example, the programmable logic controller 272 or the data acquisition/data processing device 204 may vary noise and grain parameters in the graphics software platform, such as a grain intensity multiplier parameter, a color noise parameter, a low light noise parameter, a high light noise parameter, a mid-grey level parameter, a color weight parameter, and a noise softness parameter. The grain intensity multiplier parameter sets a value within a range from 0 to 10 as a global modifier for intensity of all grain effects. The color noise parameter sets a value within a range from 0 to 1 to add noise for all colors evenly. The low light noise parameter or black boost parameter sets a value within a range from 0 to 1 to add noise for low light/color levels. The high light noise parameter or white boost parameter sets a value within a range from 0 to 1 to add noise for high light/color levels. The mid-grey level parameter sets a value within a range from 0 to 1 so as to establish a division point for black/white boost levels. The color weight parameters set values within a range from 0 to 255 so as to establish levels for red, green, blue, and alpha to tint the noise to a given color. The noise softness parameter sets a value within a range from 0 to 0.99 so as to determine how soft/crisp the noise appears.

In addition to the examples given above, the programmable logic controller 272 or the data acquisition/data processing device 204 may also vary a texture offset parameter or a texture tiling parameter in the graphics software platform using the stochastic signal. Any of the parameters described above may be set as the amplitude of the stochastic signal at an update rate of 0 to 60 Hertz.

It is readily apparent from the above detailed description that the gait perturbation system 100 and balance perturbation system 200 significantly advance the field of human balance assessment and human gait analysis. For example, the gait perturbation system 100 is capable of simulating real-life conditions by subjecting the person being tested to dynamic instability by controlling the treadmill belt speed based upon the stochastic signal generated by the programmable logic controller 25 or the data acquisition/data processing device 28. Similarly, the balance perturbation system 200 is capable of simulating real-life conditions by subjecting the person being tested to random instability by controlling the displacement of the force measurement assembly 202 and/or the screen image on the output screen 268 of the subject visual display device 207 based upon the stochastic signal generated by the programmable logic controller 272 or the data acquisition/data processing device 204. As another example, the aforedescribed gait perturbation system 100 and balance perturbation system 200 are capable of generating random stimuli (e.g., randomly regulating the treadmill belt speed or the force plate displacement) in order to emulate real-life conditions encountered by the person undergoing testing. As yet another example, the gait perturbation system 100 and balance perturbation system 200 described above are capable of more effectively training a person with a gait disorder by delivering random stimuli (e.g., randomly regulating the treadmill belt speed or the force plate displacement) to the person so that he or she is able to more effectively react to unpredictable disturbances that are encountered in real-life scenarios.

In one or more embodiments, the gait perturbation system 100 and balance perturbation system 200 may be used to provide a more intense training protocol geared towards athletes or more physically capable patients. For example, the stochastic perturbations generated by these systems 100, 200 may be used to provide a constantly and randomly changing surface and/or visual environment, which can give patients better practice for the dynamic assessments, such as the Sensory Organization Test (SOT), the Motor Control Test (MCT), the Adaptation Test (ADT), and the Head Shake Sensory Organization Test (HS-SOT).

Any of the features or attributes of the above described embodiments and variations can be used in combination with any of the other features and attributes of the above described embodiments and variations as desired. Also, the compound conjunction "and/or" is used throughout this disclosure to mean one or the other, or both.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A balance and/or gait perturbation system, comprising:
a balance and/or gait perturbation device configured to receive a person thereon, the balance and/or gait perturbation device including:
a surface for receiving at least one portion of the body of the person; and
at least one force transducer, the at least one force transducer configured to sense one or more measured quantities and output one or more measurement signals that are representative of forces and/or moments being applied to the surface of the balance and/or gait perturbation device;
at least one visual display device having an output screen, the at least one visual display device configured to display one or more scenes on the output screen so that the scenes are viewable by the person; and
one or more data processing devices operatively coupled to the balance and/or gait perturbation device and the at least one visual display device, the one or more data processing devices configured to receive the one or more measurement signals that are representative of the forces and/or moments being applied to the surface of the balance and/or gait perturbation device by the person, and to convert the one or more measurement signals into output forces and/or moments, the one or more data processing devices further configured to generate a stochastic signal for controlling a display parameter of the one or more scenes on the output screen of the at least one visual display device, and the one or more data processing devices additionally configured to display the one or more scenes on the output screen of the at least one visual display device using the stochastic signal such that the one or more scenes perturb a balance and/or gait of the person;
wherein the display parameter of the one or more scenes on the output screen of the at least one visual display device affects the overall display of the one or more scenes on the output screen, rather than simply affecting one or more elements within the one or more scenes.

2. The balance and/or gait perturbation system according to claim 1, wherein the balance and/or gait perturbation device comprises a displaceable force measurement assembly, the displaceable force measurement assembly including a displaceable force plate subassembly and one or more actuators coupled to the displaceable force plate subassembly, the one or more actuators configured to adjust a displacement position of the displaceable force plate subassembly; and wherein the one or more data processing devices are further configured to control the displacement position of the displaceable force plate subassembly using the stochastic signal.

3. The balance and/or gait perturbation system according to claim 2, wherein the display parameter of the one or more scenes on the output screen of the at least one visual display device comprises a displacement of the one or more scenes on the output screen of the at least one visual display device; and
wherein the one or more data processing devices are further configured to displace the one or more scenes on the output screen of the at least one visual display device in synchrony with the displacement of the displaceable force plate subassembly.

4. The balance and/or gait perturbation system according to claim 1, wherein the balance and/or gait perturbation device comprises a treadmill, the treadmill including one or more treadmill displaceable elements and one or more speed adjustment mechanisms coupled to the one or more treadmill displaceable elements, the one or more speed adjustment mechanisms configured to adjust the speed set point at which the one or more treadmill displaceable elements are displaced; and
wherein the one or more data processing devices are further configured to control the speed set point of the one or more treadmill displaceable elements using the stochastic signal.

5. The balance and/or gait perturbation system according to claim 4, wherein the display parameter of the one or more scenes on the output screen of the at least one visual display device comprises a displacement of the one or more scenes on the output screen of the at least one visual display device; and wherein the one or more data processing devices are further configured to displace the one or more scenes on the output screen of the at least one visual display device in synchrony with the displacement of the one or more treadmill displaceable elements.

6. The balance and/or gait perturbation system according to claim 1, wherein the display parameter of the one or more scenes on the output screen of the at least one visual display device comprises a displacement of the one or more scenes on the output screen of the at least one visual display device; and wherein the one or more data processing devices are configured to displace the one or more scenes on the output screen of the at least one visual display device using the stochastic signal by rotating and/or translating the one or more scenes on the output screen of the at least one visual display device.

7. The balance and/or gait perturbation system according to claim 1, wherein the display parameter of the one or more scenes on the output screen of the at least one visual display device is selected from the group consisting of a focal distance parameter, a smoothness parameter, a focal size parameter, a blur spread parameter, a velocity scale blur parameter, a minimum velocity blur parameter, a maximum velocity blur parameter, a velocity downsample parameter, a jitter strength parameter, a grain intensity multiplier parameter, a color noise parameter, a low light noise parameter, a high light noise parameter, a mid-grey level parameter, a color weight parameter, a noise softness parameter, a texture offset parameter, a texture tiling parameter, an image rotational displacement, an image rotational velocity, an image translational displacement, and an image translational velocity.

8. The balance and/or gait perturbation system according to claim 1, further comprising at least one input device, the at least one input device configured to enable a user to input a perturbation level corresponding to at least of: (i) an amplitude of the stochastic signal, and (ii) a frequency of the stochastic signal; and wherein the one or more data processing devices are configured to generate the stochastic signal based upon at least one of: (i) the amplitude of the stochastic signal, and (ii) the frequency of the stochastic signal.

9. The balance and/or gait perturbation system according to claim 8, wherein the stochastic signal comprises a uniform stochastic signal, the one or more data processing devices configured to compute the uniform stochastic signal as a function of a randomly generated uniform signal and the perturbation level input by the user.

10. The balance and/or gait perturbation system according to claim 8, wherein the stochastic signal comprises a normal stochastic signal, the one or more data processing devices configured to compute the normal stochastic signal as a function of a normalized randomly generated uniform signal and the perturbation level input by the user.

11. The balance and/or gait perturbation system according to claim 1, further comprising at least one input device, the at least one input device configured to enable a user to manually input at least one of: (i) an amplitude of the stochastic signal, (ii) a frequency of the stochastic signal, and (iii) a signal type of the stochastic signal, the signal type of the stochastic signal being selected from the group consisting of a uniform signal and a random signal.

12. A balance and/or gait perturbation system, comprising:

a balance and/or gait perturbation device configured to receive a person thereon, the balance and/or gait perturbation device including:

one or more displaceable components configured to be displaced to a plurality of different positions, the one or more displaceable components having one or more surfaces for receiving one or more respective limbs of the person; and one or more first actuators coupled to the one or more displaceable components, the one or more first actuators configured to adjust the displacement position of the one or more displaceable components, the one or more first actuators being primary means for displacing the one or more displaceable components;

at least one visual display device having an output screen, the at least one visual display device configured to display one or more scenes on the output screen so that the scenes are viewable by the person; and a data processing device operatively coupled to the one or more first actuators and the at least one visual display device, the data processing device configured to generate a stochastic signal for controlling a display parameter of the one or more scenes on the output screen of the at least one visual display device, and the data processing device additionally configured to display the one or more scenes on the output screen of the at least one visual display device using the stochastic signal such that the one or more scenes perturb a balance and/or gait of the person;

wherein the display parameter of the one or more scenes on the output screen of the at least one visual display device is selected from the group consisting of a focal distance parameter, a smoothness parameter, a focal size parameter, a blur spread parameter, a velocity scale blur parameter, a minimum velocity blur parameter, a maximum velocity blur parameter, a velocity downsample parameter, a jitter strength parameter, a grain intensity multiplier parameter, a color noise parameter, a low light noise parameter, a high light noise parameter, a mid-grey level parameter, a color weight parameter, a noise softness parameter, a texture offset parameter, a texture tiling parameter, an image rotational displacement, an image rotational velocity, an image translational displacement, and an image translational velocity.

13. The balance and/or gait perturbation system according to claim 12, wherein the balance and/or gait perturbation device comprises a force measurement assembly, and the one or more displaceable components comprise a displaceable force plate subassembly of the force measurement assembly; and wherein the one or more first actuators are configured to adjust the displacement position of the displaceable force plate subassembly.

14. The balance and/or gait perturbation system according to claim 13, wherein the displaceable force plate subassembly includes at least one force transducer, the at least one force transducer configured to sense one or more measured quantities and output one or more measurement signals that are representative of one or more loads being applied to the one or more surfaces of the displaceable force plate subassembly by the person.

15. The balance and/or gait perturbation system according to claim 13, wherein the balance and/or gait perturbation device further comprises a base assembly having a stationary portion and a displaceable portion, the displaceable force plate subassembly forming a part of the displaceable portion of the base assembly.

16. The balance and/or gait perturbation system according to claim 15, wherein the display parameter of the one or more scenes on the output screen of the at least one visual display device comprises the image rotational displacement of the one or more scenes on the output screen of the at least one visual display device about an imaginary horizontal rotational axis disposed transversely across a width of the at least one visual display device; and
wherein the one or more first actuators are configured to rotate the displaceable force plate subassembly relative to the stationary portion of the base assembly using the stochastic signal such that the rotation of the displaceable force plate subassembly is synchronized with the image rotational displacement of the one or more scenes on the output screen of the at least one visual display device.

17. The balance and/or gait perturbation system according to claim 15, wherein the display parameter of the one or more scenes on the output screen of the at least one visual display device comprises the image translational displacement of the one or more scenes on the output screen of the at least one visual display device towards the person on the force plate subassembly and away from the person on the force plate subassembly; and
wherein the balance and/or gait perturbation device further comprises one or more second actuators coupled to the displaceable force plate subassembly, the one or more second actuators configured to translate the displaceable force plate subassembly relative to the stationary portion of the base assembly using the stochastic signal such that the translation of the displaceable force plate subassembly is synchronized with the image translational displacement of the one or more scenes on the output screen of the at least one visual display device.

18. A method for testing and/or training a person using a balance and/or gait perturbation system, the method comprising the steps of:
providing a balance and/or gait perturbation device configured to receive a person thereon, the balance and/or gait perturbation device including:
a surface for receiving at least one portion of the body of the person; and
at least one force transducer, the at least one force transducer configured to sense one or more measured quantities and output one or more measurement signals that are representative of forces and/or moments being applied to the surface of the balance and/or gait perturbation device;
providing at least one visual display device having an output screen, the at least one visual display device configured to display one or more scenes on the output screen so that the scenes are viewable by the person; and
providing one or more data processing devices operatively coupled to the balance and/or gait perturbation device and the at least one visual display device, the one or more data processing devices configured to receive the one or more measurement signals that are representative of the forces and/or moments being applied to the surface of the balance and/or gait perturbation device by the person, and to convert the one or more measurement signals into output forces and/or moments, the one or more data processing devices further configured to generate a stochastic signal for controlling a display parameter of the one or more scenes on the output screen of the at least one visual display device, and the one or more data processing devices additionally configured to display the one or more scenes on the output screen of the at least one visual display device using the stochastic signal such that the one or more scenes perturb a balance and/or gait of the person;
providing at least one input device operatively coupled to the one or more data processing devices, the at least one input device configured to enable a user to input a perturbation level corresponding to at least of: (i) an amplitude of the stochastic signal, and (ii) a frequency of the stochastic signal;
positioning the person on the surface of the balance and/or gait perturbation device;
sensing, by utilizing the at least one force transducer, one or more measured quantities that are representative of forces and/or moments being applied to the surface of the balance and/or gait perturbation device by the person and outputting one or more measurement signals representative thereof;
converting, by using the one or more data processing devices, the one or more measurement signals that are representative of the forces and/or moments being applied to the surface of the balance and/or gait perturbation device by the person into output forces and/or moments;
generating, by using the one or more data processing devices, a stochastic signal for controlling a display parameter of the one or more scenes on the output screen of the at least one visual display device,
generating, by using the one or more data processing devices, the stochastic signal based upon at least one of: (i) the amplitude of the stochastic signal, and (ii) the frequency of the stochastic signal; and
displaying, by using the one or more data processing devices, the one or more scenes on the output screen of the at least one visual display device using the stochastic signal such that the one or more scenes perturb a balance and/or gait of the person.

19. The method according to claim 18, wherein the stochastic signal comprises one of: (i) a uniform stochastic signal and (ii) a normal stochastic signal.

* * * * *